(12) United States Patent
Conradie et al.

(10) Patent No.: US 10,377,899 B2
(45) Date of Patent: Aug. 13, 2019

(54) METHODS AND MATERIALS FOR THE PRODUCTION OF MONOMERS FOR NYLON-4/POLYESTER PRODUCTION

(71) Applicant: INVISTA North America S.á r.l., Wilmington, DE (US)

(72) Inventors: Alex Van Eck Conradie, Eaglescliffe (GB); Adriana Leonora Botes, Rosedale East (GB)

(73) Assignee: INVISTA NORTH AMERICA S.A R.L., Wilmington, DE (US)

( * ) Notice: Subject to any disclaimer, the term of this patent is extended or adjusted under 35 U.S.C. 154(b) by 0 days.

(21) Appl. No.: 16/100,119

(22) Filed: Aug. 9, 2018

(65) Prior Publication Data

US 2019/0062555 A1    Feb. 28, 2019

Related U.S. Application Data

(62) Division of application No. 14/976,966, filed on Dec. 21, 2015, now Pat. No. 10,072,150.

(60) Provisional application No. 62/095,556, filed on Dec. 22, 2014.

(51) Int. Cl.
| | |
|---|---|
| *C08L 77/12* | (2006.01) |
| *C08G 69/26* | (2006.01) |
| *C07C 227/32* | (2006.01) |
| *C08G 69/08* | (2006.01) |
| *C07C 227/18* | (2006.01) |
| *C07C 221/00* | (2006.01) |
| *C07C 213/02* | (2006.01) |
| *C07C 209/68* | (2006.01) |
| *C12N 9/04* | (2006.01) |
| *C12P 7/42* | (2006.01) |
| *C12N 9/88* | (2006.01) |
| *C12P 7/18* | (2006.01) |
| *C12N 9/10* | (2006.01) |
| *C12N 9/02* | (2006.01) |
| *C12N 15/52* | (2006.01) |
| *C12P 13/00* | (2006.01) |

(52) U.S. Cl.
CPC ........... *C08L 77/12* (2013.01); *C07C 209/68* (2013.01); *C07C 213/02* (2013.01); *C07C 221/00* (2013.01); *C07C 227/18* (2013.01); *C07C 227/32* (2013.01); *C08G 69/08* (2013.01); *C08G 69/26* (2013.01); *C12N 9/0006* (2013.01); *C12N 9/0008* (2013.01); *C12N 9/1096* (2013.01); *C12N 9/88* (2013.01); *C12N 15/52* (2013.01); *C12P 7/18* (2013.01); *C12P 7/42* (2013.01); *C12P 13/001* (2013.01); *C07B 2200/07* (2013.01); *C12Y 101/01061* (2013.01); *C12Y 102/99006* (2013.01); *C12Y 206/01018* (2013.01); *C12Y 401/01015* (2013.01); *C12Y 401/01071* (2013.01)

(58) Field of Classification Search
None
See application file for complete search history.

(56) References Cited

U.S. PATENT DOCUMENTS

| | | |
|---|---|---|
| 8,377,666 B2 | 2/2013 | Haselbeck et al. |
| 2011/0014669 A1 | 1/2011 | Madden et al. |
| 2014/0186904 A1 | 7/2014 | Botes et al. |
| 2016/0222420 A1 | 8/2016 | Botes et al. |

FOREIGN PATENT DOCUMENTS

| | | |
|---|---|---|
| WO | 2014/105794 A2 | 7/2014 |
| WO | 2017/111904 A2 | 6/2017 |
| WO | 2017/111904 A3 | 11/2017 |

OTHER PUBLICATIONS

GENBANK Accession No. AAA23834, May 27, 2008, 1 page.
GENBANK Accession No. ABK71854.1, Jan. 31, 2014, 2 pages.
GENBANK Accession No. ABK74238.1, Jan. 31, 2014 2 pages.
GENBANK Accession No. ACC40567.1, Jan. 31, 2014, 2 pages.
GENBANK Accession No. ADA65057.1, Jan. 30, 2014 2 pages.
GENBANK Accession No. ADG98140.1, Jan. 28, 2014, 2 pages.
GENBANK Accession No. AEA39183.1, Apr. 4, 2011, 1 page.
GENBANK Accession No. AHX78209.1, Apr. 23, 2014, 2 pages.
GENBANK Accession No. CAA44858.1, Apr. 28, 1992, 1 pages.
GENBANK Accession No. CAA81612.1, Apr. 18, 2005, 2 pages.
GENBANK Accession No. EIV11143.1, Dec. 19, 2014, 2 pages.
GENBANK Accession No. AAA23833.1, May 27, 2008, 1 page.
GENBANK Accession No. AAA57874.1, Nov. 21, 2011, 2 pages.
GENBANK Accession No. AAA69178.1, Jul. 1, 1995, 1 page.
GENBANK Accession No. AAG08191.1, Jan. 31, 2014, 2 pages.
GENBANK Accession No. AAQ59697.1, Jan. 31, 2014, 2 pages.
GENBANK Accession No. AAY39893.1, Jan. 31, 2014, 2 pages.
GENBANK Accession No. ABA81135.1, Jul. 20, 2015, 2 pages.
GENBANK Accession No. ABI83656.1, Jan. 3, 2007, 1 pages.
GENBANK Accession No. ABK75684.1, Jan. 31, 2014, 2 pages.
GENBANK Accession No. EFV11917.1, Sep. 9, 2013, 3 pages.
Yonaha et al., "4-Aminobutyrate : 2-Oxoglutarate Aminotransferase of Streptomyces Griseus : Purification and Properties", European Journal of Biochemistry, vol. 146, Jan. 1985, pp. 101-106.
Yang et al., "Value-added Uses for Crude Glycerol—a Byproduct of Biodiesel Production", Biotechnology for Biofuels, vol. 5, No. 13, 2012, pp. 1-10.
Woolridge et al., "Efflux of the Natural Polyamine Spermidine Facilitated by the Bacillus Subtilis Multidrug Transporter Blt", The Journal of Biological Chemistry, vol. 272, No. 14, Apr. 4, 1997, pp, 8864-8866.

(Continued)

*Primary Examiner* — Suzanne M Noakes
*Assistant Examiner* — Jae W Lee
(74) *Attorney, Agent, or Firm* — Robert Furr; Thomas H. Jenkins

(57) ABSTRACT

This document describes biochemical pathways for producing 4-hydroxybutyrate, 4-aminobutyrate, putrescine or 1,4-butanediol by forming one or two terminal functional groups, comprised of amine or hydroxyl group, in a C5 backbone substrate such as 2-oxoglutarate or L-glutamate.

2 Claims, 15 Drawing Sheets

Specification includes a Sequence Listing.

(56) References Cited

OTHER PUBLICATIONS

Becker et al., "Metabolic Flux Engineering of I-lysine Production in Corynebacterium Glutamicum—Over Expression and Modification of G6P Dehydrogenase", Journal of Biotechnology, 2007, vol. 132, pp. 99-109.
Bellman et al., "Expression Control and Specificity of the Basic Amino Acid Exporter LysE of Corynebacterium Glutamicum", Microbiology, vol. 147; Jul. 1, 2001, pp. 1765-1774.
Brigham et al., "Engineering Ralstonia Eutropha for Production of Isobutanol from CO2, H2, and O2", Advanced Biofuels and Bioproducts, Chapter 39, 2013, pp. 1065-1090.
Bugg et al., "The Emerging Role for Bacteria in Lignin Degradation and Bio-product Formation", Current Opinion in Biotechnology, vol. 22, 2011, pp. 394-400.
Demain et al., "Manual of Industrial Microbiology and Biotechnology", 2nd Edition, Scale-Up of Microbial Processes, ASM Press, 1999, 5 pages.
Elkins et al., "Substrate Specificity of the RND-Type Multidrug Efflux Pumps AcrB and AcrD of *Escherichia coli* is Determined Predominately by Two Large Periplasmic Loops", Journal of Bacteriology, vol. 184, No. 23, 2002, pp. 6490-6498.
Hermann, Thomas, "Industrial Production of Amino Acids by Coryneform Bacteria", Journal of Biotechnology, vol. 104, 2003, pp. 155-172.
Iwaki et al., "Cloning and Characterization of a Gene Cluster Involved in Cyclopentanol Metabolism in Comamonas sp. Strain NCIMB 9872 and Biotransformations Effected by *Escherichia coli*-Expressed Cyclopentanone 1,2-Monooxygenase", Applied and Environmental Microbiology, vol. 68, No. 11, 2002, pp. 5671-5684.
Jarboe, "YqhD: A Broad-Substrate Range Aldehyde Reductase with Various Applications in Production of Biorenewable Fuels and Chemicals", Appl. Microbiol. Biotechnol., vol. 89, No. 2, 2011, pp. 249-257.
Jaremko et al., "The Initial Metabolic Conversion of Levulinic Acid in Cupriavidus Necator", Journal of Biotechnology, vol. 155, 2011, pp. 293-298.
Kaulmann et al., "Substrate Spectrum of ω-transaminase from Chromobacterium Violaceum DSM30191 and its Potential for Biocatalysis", Enzyme and Microbial Technology, vol. 41, 2007, pp. 626-637.
Kim et al., "Purification and Properties of a Diamine α-Ketoglutarate Transaminase from *Escherichia coli*", The Journal of Biological Chemistry, vol. 239, No. 3, Mar. 1, 1964, pp. 783-786.
Kopke et al., "2,3-Butanediol Production by Acetogenic Bacteria, an Alternative Route to Chemical Synthesis, Using Industrial Waste Gas", Applied and Environmental Microbiology, vol. 77, No. 15, 2011, pp. 5467-5475.
Larroy et al., "Characterization of the *Saccharomyces cerevisiae* YMR318C (ADH6) gene product as a broad specificity NADPH-dependent alcohol dehydrogenase: relevance in aldehyde reduction", Biochem Journal, vol. 361, No. 1, Jan. 1, 2002, pp. 163-172.
Lee et al., "Metabolic Engineering of Pentose Phosphate Pathway in Ralstonia Eutropha for Enhanced Biosynthesis of Poly-β-Hydroxybutyrate", Biotechnology Progress, vol. 19, Issue 5, 2003, pp. 1444-1449.
Lee et al., "Synthesis of Pure meso-2,3-Butanediol from Crude Glycerol Using an Engineered Metabolic Pathway in *Escherichia coli*", Applied Biochemistry arid Biotechnology, vol. 166, No. 7, 2012, pp. 1801-1813.
Li et al., "Cupriavidus Necator JMP134 Rapidly Reduces Furfural with a Zn-Dependent Alcohol Dehydrogenase", Biodegradation, vol. 22, No. 6, 2011, pp. 1215-1225.
Lim et al., "Amplification of the NADPH-Related Genes zwf and gnd for the Oddball Biosynthesis of PHB in an *E. coli* Transformant Harboring a Cloned phbCAB Operon", Journal of Bioscience and Bioengineering, vol. 93, No. 6, 2002, pp. 543-549.

Liu et al., "Two Novel Metal-Independent Long-Chain Alkyl Alcohol Dehydrogenases From Geobacillus Thermodenitrificans NG80-2", Microbiology, vol. 155, No. 6, Mar. 3, 2009, pp. 2078-2085.
Lutke-Eversloh et al., "Biochemical and Molecular Characterization of a Succinate Semialdehyde Dehydrogenase Involved in the Catabolism of 4-Hydroxybutyric Acid in Ralstonia Eutropha", FEMS Microbiology Letters, vol. 181, No. 1, Dec. 1, 1999, pp. 63-71.
Martin et al., "High-Titer Production of Monomeric Hydroxyvalerates from Levulinic Acid in Pseudomonas Putida", Journal of Biotechnology, vol. 139, No. 1, 2009, pp. 61-67.
Meijnen et al., "Improved p-Hydroxybenzoate Production by Engineered Pseudomonas Putida S12 by Using a Mixed-substrate Feeding Strategy", Applied Microbiology and Biotechnology, vol. 90, No. 3, 2011, pp. 865-893.
Neyfakh, Alexander, The Multidrug Efflux Transporter of Bacillus Subtilis is a Structural and Functional Homolog of the *Staphylococcus* NorA Protein, Antimicrobial Agents Chemotherapy, vol. 36, No. 2, 1992, pp, 484-485.
Ng et al., "Quinolone Resistance Mediated by norA: Physiologic Characterization and Relationship to flqB, a Quinolone Resistance Locus on the *Staphylococcus aureus* Chromosome", Antimicrobial Agents and Chemotherapy, vol. 38, No. 6, 1994, pp. 1345-1355.
Ohashi et al., "Continuous Production of Lactic Acid from Molasses by Perfusion Culture of Lactococcus Lactis Using a Stirred Ceramic Membrane Reactor", Journal of Bioscience and Bioengineering, vol. 87, No. 5, 1999, pp. 647-654.
Papanikolaou et al., "Citric Acid Production by Yarrowia Lipolytica Cultivated on Olive-Mill Wastewater-Based Media", Bioresource Technology, vol. 99, No. 7, 2008, pp, 2419-2428.
Perez-Pantoja et al., "Metabolic Reconstruction of Aromatic Compounds Degradation from the Genome of the Amazing Pollutant-Degrading Bacterium Cupriavidus Necator JMP134", FEMS Microbiology Reviews, vol. 32, Aug. 7, 2008, pp. 736-794.
Przybylski et al., "Third-Generation Feed Stocks for the Clean and Sustainable Biotechnological Production of Bulk Chemicals: Synthesis of 2-Hydroxyisobutyric Acid", Energy, Sustainability and Society, vol. 2, No. 11, 2012, 9 pages.
Ramsay et al., "Use of a Nylon Manufacturing Waste as an Industrial Fermentation Substrate", Applied and Environmental Microbiology, vol. 52, No. 1, Jul. 1986, pp. 152-156.
Samsonova et al., "Molecular Cloning and Characterization of *Escherichia coli* K12 ygjG gene", BMC Microbiology, vol. 3, No. 2, Jan. 31, 2003, pp. 1-10.
Satoh et al., "Enzyme-catalyzed poly(3-hydroxybutyrate) synthesis from acetate with CoA recycling and NADPH regeneration in Vitro", Journal of Bioscience and Bioengineering, vol. 95, No. 4, 2003, pp. 335-341.
Seedorf et al., "The Genome of Clostridium Kluyveri, A Strict Anaerobe with Unique Metabolic Features", PNAS USA, vol. 105, No. 6, Feb. 12, 2008, pp, 2128-2133.
Shen et al., "Driving Forces Enable High-Titer Anaerobic 1-Butanol Synthesis in *Escherichia coli*", Applied and Environmental Microbiology, vol. 77, No. 9, May 2011, pp. 2905-2915.
Suzuki et al., "GriC arid GriD Constitute a Carboxylic Acid Reductase Involved in Grixazone Biosynthesis in Streptomyces Griseus", Journal of Antibiotics, vol. 60, No. 6, 2007, pp. 380-387.
Venkitasubramanian et al., "Aldehyde Oxidoreductase as a Biocatalyst: Reductions of Vanillic Acid", Enzyme and Microbial Technology, vol. 42, No. 2, Jan. 2008, pp. 130- 137.
Wee et al., "Biotechnological Production of Lactic Acid and Its Recent Applications", Food Technology and Biotechnology, vol. 44, No. 2, 2006, pp. 163-172.
Liu et al., "Autonomous Production of 1,4-Butanediol via a de novo Biosynthesis Pathway in Engineered *Escherichia coli*", Metabolic Engineering, 2015, pp, 135-141.
Nielsen et al., "Metabolic Engineering: From Retrofitting to Green Field", Nature Chemical Biology, vol. 7, 2011, pp. 408-409.
Takahashi et al., "Metabolic Pathways for Cytotoxic End Product Formation from Glutamate- and Aspartate-Containing Peptides byPorphyromonas gingivalis", Journal of Bacteriology, 2000, pp. 4704-4710.

(56) References Cited

OTHER PUBLICATIONS

International Search Report and Written Opinion received for PCT Application No. PCT/US2015/067090, dated Oct. 2, 2017, 25 Pages.
International Preliminary Report on Patentability received for PCT Application No. PCT/US2015/067090, dated Nov. 2, 2017, 18 pages.

FIGURE 5

| SEQ ID NO | Organism | GENBANK reference | Amino acid sequence |
|---|---|---|---|
| 1 | Mycobacterium marinum | ACC40567.1 | MSPITREERLERRIQDLYANDPQFAAAKPATAITAAIERPGLPLPQIIETVMTGYADRPA LAQRSVEFVTDAGTGHTTLRLLPHFETISYGELWDRISALADVLSTEQTVKPGDRVCLLG FNSVDYATIDMTLARLGAVAVPLQTSAAITQLQPIVAETQPTMIAASVDALADATELALS GQTATRVLVFDHHRQVDAHRAAVESARERLAGSAVVETLAEAIARGDVPRGASAGSAPGT DVSDDSLALLIYTSGSTGAPKGAMYPRRNVATFWRKRTWFEGGYEPSITLNFMPMSHVMG RQILYGTLCNGGTAYFVAKSDLSTLFEDLALVRPTELTFVPRVWDMVFDEFQSEVDRRLV DGADRVALEAQVKAEIRNDVLGGRYTSALTGSAPISDEMKAWVEELLDMHLVEGYGSTEA GMILIDGAIRRPAVLDYKLVDVPDLGYFLTDRPHPRGELLVKTDSLFPGYYQRAEVTADV FDADGFYRTGDIMAEVGPEQFVYLDRRNNVLKLSQGEFVTVSKLEAVFGDSPLVRQIYIY GNSARAYLLAVIVPTQEALDAVPVEELKARLGDSLQEVAKAAGLQSYEIPRDFIIETTPW TLENGLLTGIRKLARPQLKKHYGELLEQIYTDLAHGQADELRSLRQSGADAPVLVTVCRA AAALLGGSASDVQPDAHFTDLGGDSLSALSFTNLLHEIFDIEVPVGVIVSPANDLQALAD YVEAARKPGSSRPTFASVHGASNGQVTEVHAGDLSLDKFIDAATLAEAPRLPAANTQVRT VLLTGATGFLGRYLALEWLERMDLVDGKLICLVRAKSDTEARARLDKTFDSGDPELLAHY RALAGDHLEVLAGDKGEADIGLDRQTWQRLADTVDLIVDPAALVNHVLPYSQLFGPNALG TAELLRLALTSKIKPYSYTSTIGVADQIPPSAFTEDADIRVISATRAVDDSYANGYSNSK WAGEVLLREAHDLCGLPVAVFRCDMILADTTWAGQLNVPDMFTRMILSLAATGIAPGSFY ELAADGARQRAHYDGLPVEFIAEAISTLGAQSQDGFHTYHVMNPYDDGIGLDEFVDWLNE SGCPIQRIADYGDWLQRFETALRALPDRQRHSSLLPLLHNYRQPERPVRGSIAPTDRFRA AVQEAKIGPDKDIPHVGAPIIVKYVSDLRLLGLL |

FIGURE 5 (Continued)

| SEQ ID NO | Organism | GENBANK reference | Amino acid sequence |
|---|---|---|---|
| 2 | Mycobacterium smegmatis | ABK71854.1 | MTSDVHDATDGVTETALDDEQSTRRIAELYATDPEFAAAAPLPAVVDAAHKPGLRLAEIL QTLFTGYGDRPALGYRARELATDEGGRTVTRLLPRFDTLTYAQVWSRVQAVAAALRHNFA QPIYPGDAVATIGFASPDYLTLDLVCAYLGLVSVPLQHNAPVSRLAPILAEVEPRILTVS AEYLDLAVESVRDVNSVSQLVVFDHHPEVDDHRDALARAREQLAGKGIAVTTLDAIADEG AGLPAEPIYTADHDQRLAMILYTSGSTGAPKGAMYTEAMVARLWTMSFITGDPTPVINVN FMPLNHLGGRIPISTAVQNGGTSYFVPESDMSTLFEDLALVRPTELGLVPRVADMLYQHH LATVDRLVTQGADELTAEKQAGAELREQVLGGRVITGFVSTAPLAAEMRAFLDITLGAHI VDGYGLTETGAVTRDGVIVRPPVIDYKLIDVPELGYFSTDKPYPRGELLVRSQTLTPGYY KRPEVTASVFDRDGYYHTGDVMAETAPDHLVYVDRRNNVLKLAQGEFVAVANLEAVFSGA ALVRQIFVYGNSERSFLLAVVVPTPEALEQYDPAALKAALADSLQRTARDAELQSYEVPA DFIVETEPFSAANGLLSGVGKLLRPNLKDRYGQRLEQMYADIAATQANQLRELRRAAATQ PVIDTLTQAAATILGTGSEVASDAHFTDLGGDSLSALTLSNLLSDFFGFEVPVGTIVNPA TNLAQLAQHIEAQRTAGDRRPSFTTVHGADATEIRASELTLDKFIDAETLRAAPGLPKVT TEPRTVLLSGANGWLGRFLTLQWLERLAPVGGTLITIVRGRDDAAARARLTQAYDTDPEL SRRFAELADRHLRVVAGDIGDPNLGLTPEIWHRLAAEVDLVVHPAALVNHVLPYRQLFGP NVVGTAEVIKLALTERIKPVTYLSTVSVAMGIPDFEEDGDIRTVSPVRPLDGGYANGYGN SKWAGEVLLREAHDLCGLPVATFRSDMILAHPRYRGQVNVPDMFTRILLSLLITGVAPRS FYIGDGERPRAHYPGLITVDFVAEAVTTLGAQQREGVVSYDVMNPHDDGISLDVFVDWLIR AGHPIDRVDDYDYDWVRRFETALTALPEKRRAQTVLPLLHAFRAPQAPLRGAPEPTEVFHA AVRTAKVGPGDIPHLDEALIDKYIRDLREFGLI |

FIGURE 5 (Continued)

| SEQ ID NO | Organism | GENBANK reference | Amino acid sequence |
|---|---|---|---|
| 3 | Segniliparus rugosus | EFV11917.1 | MGDGEERAKRFFQRIGELSATDPQFAAAAPDPAVVEAVSDPSLSFTRYLDTLMRGYAERP ALAHRVGAGYETISYGELWARVGAIAAAWQADGLAPGDFVATVGFTSPDYVAVDLAAARS GLVSVPLQAGASLAQLVGILEETEPKVLAASASSLEGAVACALAAPSVQRLVVFDLRGPD ASESAADERRGALADAEEQLARAGRAVVVETLADLAARGEALPEAPLFEPAEGEDPLALL IYTSGSTGAPKGAMYSQRLVSQLWGRTPVVPGMPNISLHYMPLSHSYGRAVLAGALSAGG TAHFTANSDLSTLFEDIALARPTFLALVPRVCEMLFQESQRGQDVAELRERVLGGRLLVA VCGSAPLSPEMRAFMEEVLGFPLLDGYGSTEALGVMRNGHQRPPVIDYKLVDVPELGYR TTDKPYPRGELCIRSTSLISGYYKRPEITAEVFDAQGYYKTGDVMAEIAPDHLVVDRSK NVLKLSQGEFVAVAKLEAAYGTSPVKQIFVYGNSERSFLLAVVVPNAEVLGARDQEEAK PLIAASLQKIAKEAGLQSYEVPRDFLIETEPFTTQNGLLSEVGKLLRPKLKARYGEALEA RYDEIAHGQADELRALRDGAGQRPVVETVVRAAVAISGSEGAEVGPEANFADLGGDSLSA LSLANLLHDVFEVEVPVRIIIGPTASLAGIAKHIEAERAGASAPTAASVHGAGATRIRAS ELTLEKFLPEDLLAAAKGLPAADQVRTVLLTGANGWLGRFLALEQLERLARSGQDGGKLI CLVRGKDAAAARRIEETLGTDPALAARFAELAEGRLEVVPGDVGEPKFGLDDAAWDRLA EEVDVIVHPAALVNHVLPYHQLFGPNVVGTAEIIRLAITAKRKPVTYLSTVAVAAGVEPS SFEEGDDIRAVVPERPLGDGYANGYGNSKWAGEVLLREAHELVGLPVAVFRSDMILAHTR YTGQLNVPDQFTRLVLSLLATGIAPKSFYQQGAAGERQRAHYDGIPVDFTAEAITTLGAE PSWFDGGAGFRSFDVFNPHHDGVGLDEFVDWLIEAGHPISRIDDHKEWFARFETAVRGLP EAQRQHSILPLLRAYSFPHPPVDGSVYPTGKFQGAVKAAQVGSDHDVPHLGKALIVKYAD DLKALGLL |

FIGURE 5 (Continued)

| SEQ ID NO | Organism | GENBANK reference | Amino acid sequence |
|---|---|---|---|
| 4 | Mycobacterium massiliense | EIV11143.1 | MTNETNPQQEQLSRRIESLRESDPQFRAAQPDPAVAEQVLRPGLHLSEAIAALMTGYAER PALGERARELVIDQDGRTTLRLLPRFDTTTYGELWSRTTSVAAAWHHDATHPVKAGDLVA TLGFTSIDYTVLDLAIMILGGVAVPLQTSAPASQWTTILAEAEPNTLAVSIELIGAAMES VRATPSIKQVVFDYTPEVDQREAFEAASTQLAGTGIALETLDAVIARGAALPAAPLYA PSAGDDPLALLIYTSGSTGAPKGAMHSENIVRRWWIREDVMAGTENLPMIGLNFMPMSHI MGRGTLTSTLSTGGTGYFAASSDMSTLFEDMELIRPTALALVPRVCDMVFQRFQTEVDRR LASGDTASAEAVAAEVKADIRDNLFGGRVSAVMVGSAPLSEEIGEFIESCFELNLTDGYG STEAGMVFRDGIVQRPPVIDYKLVDVPELGYFSTDKPHPRGELLLKTDGMFLGYYKRPEV TASVFDADGFYMTGDIVAELAHDNIEHDRRNNVLKLSQGEFVAVATLEAEYANSPVVHQ IYVYGSSERSYLLAVVPTPEAVAAAKGDAAALKTIADSLQDIAKEIQLQSYEVPRDFI IEPQPFTQGNGLLTGIAKLARPNLIKAHYGPRLEQMYAEIAEFQQAAELRALHGVDPDKPAL ETVLKAAQALLGVSSAELAADAHFTDLGGDSLSALSFSDLLRDIFAVEVPVGVIVSAAND LGGVAKFVDEQRHSGGTRPTAETVHGAGHTEIRAADLTLDKFIDEATLHAAPSLPKAAGI PHTVLLTGSNGYLGHYLALEWLERLDKTDGKLIVIVRGKNAEAAYGRLEEAFDTGDTELL AHFRSLADKHLEVLAGDIGDPNLGLDADTWQRLADTVDVIVHPAALVNHVLPYNQLFGPN VVGTAEIIKLAITTKIKPVTYLSTVAVAAYVDPTTFDEESDIRLISAVRPIDDGYANGYG NAKWAGEVLLREAHDLCGLPVAVFRSDMILAHSRYTGQLNVPDQFTRLILSLIATGIAPG SFYQAQTTGERPLAHYDGLPGDFTAEAITTLGTQVPEGSEGFVTYDCVNPHADGISLDNF VDWLIEAGYPIARIDNYTEWFTRFDTAIRGLSEKQKQHSLLPLLHAFEQPSAAENHGVVP AKRFQHAVQAAGIGPVGQDGTTDIPHLSRRLIVKYAKDLEQLGLL |

FIGURE 5 (Continued)

| SEQ ID NO | Organism | GENBANK reference | Amino acid sequence |
|---|---|---|---|
| 5 | Segniliparus rotundus | ADG98140.1 | MTQSHTQGPQASAAHSRLARRAAELLATDPQAAATLPDPEVVRQATRPGLRLAERVDAIL SGYADRPALGQRSFQTVKDPITGRSSVELLPTFQTITYRELRERATAIASDLAHHPQAPA KPGDFLASIGFISVDYVAIDIAGVFAGLTAVPLQTGATLATLIAITAETAPTLFAASIEH LPTAVDAVLATPSVRRLLVFDYRAGSDEDREAVEAAKRKIADAGSSVLVDVLDEVIARGK SAPKAPLPPATDAGDDSLLIYTSGSTGTPKGAMYPERNVAHFWGGVWAAAFDEDAAPP VPAINTFLPLSHVASRLSLMPTLARGGLMHFVAKSDLSTLFEDLKLARPTNLFLVPRVV EMLYQHYQSELDRRGVQDGTREAEAVKDLRTGLLGGRILTAGFGSAPLSAELAGFIESL LQIHLVDGYGSTEAGPVWRDGYLVKPPVTDYKLIDVPELGYFSTDSPHPRGELAIKTQTI LPGYYKRPETTAEVFDEDGFYLTGDVVAQIGPEQFAYVDRRKNVLKLSQGEFVTLAKLEA AYSSPLVRQLFVYGSSERSYILAVIVPTPDALKKFGVGEAAKAALGESLQKIARDEGLQ SYEVPRDFHIETDPFTVENGLLSDARKSLRPKLKEHYGERLEAMYKELADGQANELRDIR RGVQQRPTLETVRRAAAAMLGASAAEIKPDAHFTDLGGDSLSALTFSNFLHDLFEVDVPV GVIVSAANTLGSVAEHIDAQLAGGRARPTFATVHGKGSTTIKASDLTLDKFIDEQTLEAA KHLPKPADPPRTVLLTGANGWLGRFLALEWLERLAPAGGKLITIVRGKDAAQAKARLDAA YESGDPKLAGHYQDLAATTLEVLAGDFSEPRLGLDEATWNRLADEVDFISHPGALVNHVL PYNQLFGPNVAGVAEIIKLAITTRIKPVTYLSTVAVAAGVEPSALDEDGDIRTVSAERSV DEGYANGYGNSKWGGEVLLREAHDRTGLPVRVFRSDMILAHQKYTGQVNATDQFTRLVQS LLATGLAPKSFYELDAQGNRQRAHYDGIPVDFTAESITTLGGDGLEGYRSYNVFNPHRDG VGLDEFVDWLIEAGHPITRIDDYDQWLSRFETSLRGLPESKRQASVLPLLHAFARPGPAV DGSPFRNTVFRTDVQKAKIGAEHDIPHLGKALVLKYADDIKQLGLL |
| 6 | Chromobacterium violaceum | AAQ59697.1 | MQKQRTTSQWRELDAAHHLHPFTDTASLNQAGARVMTRGEGVYLWDSEGNKIIDGMAGLW CVNVGYGRKDFAEAARRQMEELPFYNTFFKTTHPAVVELSSLLAEVTPAGFDRVFYTNSG SESVDTMIRMVRRYWDVQGKPEKKTLIGRWNGYHGSTIGGASLGGMKYMHEQGDLPIPGM AHIEQPWWYKHGKDMTPDEFGVVAARWLEEKILEIGADKVAAFVGEPIQGAGGVIVPPAT YWPEIERICRKYDVLLVADEVICGFGRTGEWFGHQHFGFQPDLFTAAKGLSSGYLPIGAV FVGKRVAEGLIAGGDFNHGFTYSGHPVCAAVAHANVAALRDEGIVQRVKDDIGPYMQKRW RETFSRFEHVDDVRGVGMVQAFTLVKNKAKRELFPDFGEIGTLCRDIFFRNNLIMRACGD HIVSAPPLVMTRAEVDEMLAVAERCLEEFEQTLKARGLA |

FIGURE 5 (Continued)

| SEQ ID NO | Organism | GENBANK reference | Amino acid sequence |
|---|---|---|---|
| 7 | Pseudomonas aeruginosa | AAG08191.1 | MNARLHATSPLGDADLVRADQAHYMHGYHVFDDHRVNGSLNIAAGDGAYYDTAGNRYLD AVGGMWCTNIGLGREEMARTVAEQTRLLAYSNPFCDMANPRAIELCRKLAELAPGDLDHV FLTTGGSTAVDTAIRLMHYYQNCRGKRAKKHVITRINAYHGSTFLGMSLGGKSADRPAEF DFLDERIHHLACPYYYRAPEGLGEAEFLDGLVDEFERKILELGADRVGAFISEPVFGSGG VIVPPAGYHRRMWELCQRYDVLYISDEVVTSFGRLGHFFASQAVFGVQPDIILTAKGLTS GYQPLGACIFSRRIWEVIAEPDKGRCFSHGFTYSGHPVACAAALKNIEIEREGLLAHAD EVGRYFEERLQSLRDLPIVGDVRGMRFMACVEFVADKASKALFPESLNIGEWVHLRAQKR GLLVRPIVHLNVMSPPLILTREQVDTVVRVLRESIEETVEDLVRAGHR |
| 8 | Pseudomonas syringae | AAY39893.1 | MSANNPQTLEWQALSSEHHLAPFSDYKQLKEKGPRIITRAEGVYLWDSEGNKILDGMSGL WCVAIGYGREELADAASKQMRELPYYNLFFQTAHPPVLELAKAISDIAPEGMNHVFFTGS GSEGNDTMLRMVRHYWALKGQPNKKTIISRVNGYHGSTVAGASLGGMTYMHEQGDLPIPG VVHIPQPYWFGEGGDMTPDEFGIWAAEQLEKKILELGVENVGAFIAEPIQGAGGVIVPPD SYWPKIKEILSRYDILFAADEVICGFGRTSEWFGSDFYGLRPDMMTIAKGLTSGYVPMGG LIVRDEIVAVLNEGGDFNHGFTYSGHPVAAAVALENIRILREEKIVERVRSETAPYLQKR LRELSDHPLVGEVRGVGLLGAIELVKDKTTRERYTDKGAGMICRTFCFDNGLIMRAVGDT MIIAPPLVISFAQIDELVEKARTCLDLTLAVLQG |
| 9 | Rhodobacter sphaeroides | ABA81135.1 | MTRNDATNAAGAVGAAMRDHILLPAQEMAKLGKSAQPVLTHAEGIYVHTEDGRRLIDGPA GMWCAQVGYGRREIVDAMAHQAMVLPYASPWVMATSPAARLAEKIATLTPGDLNRIFFTT GGSTAVDSALRFSEFYNNVLGRPQKKRIIVRDYGYHGSTALTAACTGRTGNWPNFDIAQD RISFLSSPNPRHAGNRSQEAFLDDLVQEFEDRIESLGPDTIAAFLAEPILASGGVIIPPA GYHARFKAICEKHDILYISDEVVTGFGRCGEWFASEKVFGVVPDIITFAKGVTSGYVPLG GLAISEAVLARISGENAKGSWFTNGYTYSNQPVACAAALAMIELMEREGIVDQAREMADY FAAALASLRDLPGVAETRSVGLVGCVQCLLDPTRADGTAEDKAFTLKIDERCFELGLIVR PLGDLCVISPPLIISRAQIDEMVAIMRQAITEVSAAHGLTAKEPAAV |
| 10 | Escherichia coli | AAA57874.1 | MNRLPSSASALACSAHALNLIEKRTLDHEEMKALNREVIEYFKEHVNPGFLEYRKSVTAG GDYGAVEWQAGSLNTLVDTQGQEFIDCLGGGIFNVGHRNPVVVSAVQNQLAKQPLHSQE LLDPLRAMLAKTLAALTPGKLKYSFFCNSGTESVEAALKLAKAYQSPRGKFTFIATSGAF HGKSLGALSATAKSTFRKPFMPLLPGFRHVPFGNIEAMRTALNECKKTGDDVAAVILEPI QGEGGVILPPPGYLTAVRKLCDEFGALMILDEVQTGMGRTGKMFACEHENVQPDILCLAK ALGGGVMPIGATIATEEVFSVLFDNPFLHTTTFGGNPLACAAALATINVLLEQNLPAQAE QKGDMLLDGFRQLAREYPDLVQEARGKGMLMAIEFVDNEIGYNFASEMFRQRVLVAGTLN NAKTIRIEPPLTLTIEQCELVIKAARKALAAMRVSVEEA |

FIGURE 5 (Continued)

| SEQ ID NO | Organism | GENBANK reference | Amino acid sequence |
|---|---|---|---|
| 11 | Vibrio fluvialis | AEA39183.1 | MNKPQSWEARAETYSLYGFTDMPSLHQRGTVVTHGEGPYIVDVNGRRYLDANSGLWNMV AGFDHKGLIDAAKAQYERFPGYHAFFGRMSDQTVMLSEKLVEVSPFDSGRVFYTNSGSEA NDTMVKMLWFLHAAEGKPQKRKILTRWNAYHGVTAVSASMTGKPYNSVFGLPLPGFVHLT CPHYWRYGEEGETEEQFVARLARELEETIQREGADTIAGFFAEPVMGAGGVIPPAKGYFQ AILPILRKYDIPVISDEVICGFGRTGNTWGCVTYDFTPDAIISSKNLTAGFFPMGAVILG PELSKRLETAIEAIEEFPHGFTASGHPVGCAIALKAIDVVMNEGLAENVRRLAPREFERL KHIAERPNIGEYRGIGFMWALEAVKDKASKTPFDGNLSVSERIANTCTDLGLICRPLGQS VVLCPPFILTEAQMDEMFDKLEKALDKVFAEVA |
| 12 | Bacillus subtilis | CAA44858.1 | MKIYGIYMDRPLSQEENERFMSFISPEKREKCRRFYHKEDAHRTLLGDVLVRSVISRQYQ LDKSDIRFSTQEYGKPCIPDLPDAHFNISHSGRWVICAFDSQPIGIDIEKTKPISLEIAK RFFSKTEYSDLLAKDKDEQTDYFYHLWSMKESFIKQEGKGLSLPLDSFSVRLHQDGQVSI ELPDSHSPCYIKTYEVDPGYKMAVCAAHPDFPEDITMVSYEELL |
| 13 | Nocardia sp. NRRL 5646 | ABI83556.1 | MIETILPAGVESAELLEYPEDLKAHPAEEHLIAKSVEKRRDFIGARHCARLALAELGEP PVAIGKGERGAPIWPRGVVGSLTHCDGYRAAAVAHKMRFRSIGIDAEPHATLPEGVLDSV SLPPEREWLKTTDSAILHLDRLLFCAKEATYKAWWPLTARWLGFEEAHITFELEDGSADSG NGTFHSELLVPGQTNDGGTPLLSFDGRWLIADGFILTAIAYA |
| 14 | Escherichia coli | AAA23833.1 | MDQKLLTDFRSELLDSRFGAKAISTIAESKRFPLHEMRDDVAFQIINDELYLDGNARQNL ATFCQTWDDENVHKLMDLSINKNWIDKEEYPQSAAIDLRCVNMVADLWHAPAPKNGQAVG TNTIGSSEACMLGGMAMKWRWRKRMEAAGKPTDKPNLVCGPVQICWHKFARYWDVELREI PMRPGQLFMDPKRMIEACDENTIGVVPTFGVTYTGNYEFPQPLHDALDKFQADTGIDIDM HIDAASGGFLAPFVAPDIVWDFRLPRVKSISASGHKFGLAPLGCGWVIWRDEEALPQELV FNVDYLGGQIGTFAINFSRPAGQVIAQYYEFLRLGREGYTKVQNASYQVAAYLADEIAKL GPYEFICTGRPDEGIPAVCFKLKDGEDPGYTLYDLSERLRLRGWQVPAFTLGGEATDIVV MRIMCRRGFEMDFAELLLEDYKASLKYLSDHPKLQGIAQQNSFKHT |
| 19 | Escherichia coli | AAA23834.1 | MDKKQVTDLRSELLDSRFGAKISTIAESKRFPLHEMRDDVAFQIINDELYLDGNARQNL ATFCQTWDDENVHKLMDLSINKNWIDKEEYPQSAAIDLRCVNMVADLWHAPAPKNGQAVG TNTIGSSEACMLGGMAMKWRWRKRMEAAGKPTDKPNLVCGPVQICWHKFARYWDVELREI PMRPGQLFMDPKRMIEACDENTIGVVPTFGVTYTGNYEFPQPLHDALDKFQADTGIDIDM HIDAASGGFLAPFVAPDIVWDFRLPRVKSISASGHKFGLAPLGCGWVIWRDEEALPQELV FNVDYLGGQIGTFAINFSRPAGQVIAQYYEFLRLGREGYTKVQNASYQVAAYLADEIAKL GPYEFICTGRPDEGIPAVCFKLKDGEDPGYTLYDLSERLRLRGWQVPAFTLGGEATDIVV MRIMCRRGFEMDFAELLLEDYKASLKYLSDHPKLQGIAQQNSFKHT (SEQ ID NO: 19) |

FIGURE 5 (Continued)

| SEQ ID NO | Organism | GENBANK reference | Amino acid sequence |
|---|---|---|---|
| 15 | Lactococcus lactis | ADA65057.1 | MYTVGDYILLDRLHELGIEEIFGVPGDYNLQFLDQIISRKDMKWVGNANELNASYMADGYA RTKKAAAFLTTFGVGELSAVNGLAGSYAENLPVVEIVGSPTSKVQNEGKFVHHTLADGDF KHFMKMHEPVTAARTLLTAENATVEIDRVLSALLKERKPVYINLPVDVAAAKAEKPSLPL KKENPTSNTSDQEILNKIQESLKNAKKPIVITGHEIISFGLENTVTQFISKTKLPITTLN FGKSSVDETLPSFLGIYNGKLSEPNLKEFVESADFILMLGVKLTDSSTGAFTHHLNENKM ISLNIDEGKIFNESIQNFDFESLISSLLDLSGIEYKGKYIDKKQEDFVPSNALLSQDRLW QAVENLTQSNETIVAEQGTSFFGASSIFLKPKSHFIGQPLWGSIGYTFPAALGSQIADKE SRHLLFIGDGSLQLTVQELGLAIREKINPICFIINNDGYTVEREIHGPNQSYNDIPMWNY SKLPESFGATEERVVSKIVRTENEFVSMKEAQADPNRMYWIELVLAKEDAPKVLKKMGK LFAEQNKS |
| 16 | Mycobacterium smegmatis | ABK74238.1 | MSSSPSPFGQNEWLVEEMYRKFRDDPSSVDPSWHEFLVDYSPEPTTDSASNGRTTTAAPV TPPTPAPAPAPEPKAAPKPAAKTEAKPAKPAKSATPAKGDESQILRGAAAAVVKNMNASL EVPTATSVRAIPAKLMIDNRVVINNHLKRTRGGKISFTHLLGYAIVQAVKKFPNMNRHFA VVDGKPTAITPAHTNLGLAIDLQGKDGNRSLVVAAIKRCETMRFGQFIAAYEDIVRRARD GKLTAEDFSGVTISLTNPGTLGTVHSVPRLMQGQGAIIGAGAMEYPAEFQGASEERIADL GIGKLITLTSTYDHRIIQGAESGDFLRTHQLLLDDDFFDEIFRELGIPYEPVRWRTDNP DSIEDKNARVIELIAAYRNRGHLMADIDPLRLDNTRFRSHPDLDVNSHGLTLWDLDREFK VDGFAGVQRKKLRDILSVLRDAYCRHVGVEYTHILEPEQQRWIQERVETKHDKPTVAEQK YILSKLNAAEAFETFLQTKYVGQKRFSLEGAETVIPMMDAVIDQCAEHGLDEVVIAMPHR GRLNVLANIVGKPYSQIFSEFEGNLNPSQAHGSGDVKYHLGATGTYIQMFGDNDIEVSLT ANPSHLEAVDPVLEGLVRAKQDLLDTGEEGSDNRFSVVPLMLHGDAAFAGQGVVAETLNL ALLRGYRTGGTIHIVVNNQIGFTTAPTDSRSSEYCTDVAKMIGAPIFHVNGDDPEACAWV ARLAVDFRQAFKKDVVIDMLCYRRGHNEGDDPSMTQPYMYDVIDTKRGSRKAYTEALIG RGDISMKEAEDALRDYQGQLERVFNEVRELEKHEIEPSESVEADQQIPSKLATAVDKAML QRIGDAHLALPEGFTVHPRVRPVLEKRREMAYEGRIDWAFAELALGSLIAEGKLVRLSG QDTQRGFTFQRHAVIVDRKTGEEFTPLQLLATNPDGTPTGGKFLVYNSALSEFAAVGFEY GYSVGNPDAMVLWEAQFGDFVNGAQSIIDEFISSGEAKWGQLSDVVLLPHGHEGQGPDH TSGRIERFLQLWAEGSMTIAMPSTPANYFHLLRRHGKDGIQRPLIVFTPKSMLRNKAAVS DIRDFTESKFRSVLEEPMYTDGEGDRNKVTRLLLTSGKIYYELAARKAKENREDVAIVRI EQLAPLPRRRLAETLDRYPNVKEKFWVQEEPANCQGAWPSFGLTLPEILPDHFTGLKRISR RAMSAPSSGSSKVHAVEQQEILDTAFG |

FIGURE 5 (Continued)

| SEQ ID NO | Organism | GENBANK reference | Amino acid sequence |
|---|---|---|---|
| 17 | Salmonella typhimurium | AHX78209.1 | MQNPYTVADYLLDRLAGCGIGHLFGVPGDYNLQFLDHVIDHPTLRWVGCANELNAAYAAD GYARMSGAGALLTTFGVGELSAINGIAGSYAEYVPVLHVGAPCSAAQQRGELMHHTLGD GDFRHFYRMSQAISAASAILDEQNACFEIDRVLGEMLAARRPGYIMLPADVAKKTAIPPT QALALPVHEAQSGVETAFRYHARQCLMNSRRIALLADFLAGRFGLRPLLQRWMAETPIAH ATLLMGKGLFDEQHPNFVGTYSAGASSKEVRQAIEDADRVICVGTRFVDTLTAGFTQQLP AERTLEIQPYASRIGETWFNLPMAQAVSTLRELCLECAFAPPPTRSAGQPVRIDKGELTQ ESFWQTLQQYLKPGDIILVDQGTAAFGAAAALSLPDGAEVVLQPLWGSIGYSLPAAFGAQT ACPDRRVILIGDGAAQLTIQEMGSMLRDGQAPVILLLNNDGYTVERAIHGAAQRYNDIA SWNWTQIPPALNAAQQAECWRVTQAIQLAEVLERLARPQRLSFIEVMLPKADLPELLRTV TRALEARNGG |
| 18 | Mycobacterium smegmatis | ABK75684.1 | MTIETREDRFNRRIDHLFETDPQFAAARPDEAISAAAADPELRLPAAVKQILAGYADRPA LGKRAVEFVTDEEGRTTAKLLPRFDTITYRQLAGRIQAVTNAWHNHPVNAGDRVAILGFT SVDYTTIDIALLELGAVSVPLQTSAPVAQLQPIVAETEPKVIASSVDFLADAVALVESGP APSRLVVFDYSHEVDDQREAFEAAKGKLAGTGVVVETITDALDRGRSLADAPLYVPDEAD PLTLLIYTSGSTGTPKGAMYPESKTATMWQAGSKARWDETLGVMPSITLNFMPMSHVMGR GILCSTLASGGTAYFAARSDLSTFLEDLALVRPTQLNFVPRIWDMLFQEYQSRLDNRRAE GSEDRAEAAVLEEVRTQLLGGRFVSALTGSAPISAEMKSWVEDLLDMHLLEGYGSTEAGA VFIDGQIQRPPVIDYKLVDVPDLGYFATDRPYPRGELLVKSEQMFPGYYKRPEITAEMFD EDGYYRTGDIVAELGPDHLEYLDRRNNVLKLSQGEFVTVSKLEAVFGDSPLVRQIYVYGN SARSYLLAVVVPTEEALSRWDGDELKSRISDSLQDAARAAGLOSYEIPRDFLVETTPFTL ENGLLTGIRKLARPKLKAHYGERLEQLYTDLAEGQANELRELRRNGADRPVVETVSRAAV ALLGASVTDLRSDAHFTDLGGDSLSALSFNLLHEIFDVDPVPGVIVSPATDLAGVAAYI EGELRGSKRPTVASVHGRDATEVRARDLALGKFIDAKTLSAAPGLPRSGTEIRTVLLTGA TGFLGRYLALEWLERMDLVDGKVICLVRARSDDEARARLDATFDTGDATLLEHYRALAAD HLEVIAGDKGEADLGLDHDTWQRLADTVDLIVDPAALVNHVLPYSQMFGPNALGTAELIR IALTTTIKPYVYVSTIGVGQGISPEAFVEDADIREISATRRVDDSYANGYGNSKWAGEVL LREAHDWCGLPVSVFRCDMILADTTYSGQLNLPDMFTRLMLSLVATGIAPGSFYELDADG NRQRAHYDGLPVEFIAEAISTIGSQVTDGFETFHVMNPYDDGIGLDEYVDWLIEAGYPVH RVDDYATWLSRFETALRALPERQRQASLLPLLHNYQQPSPPVCGAMIAPTDRFRAAVQDAK IGPDKDIPHVTADVIVKYISNLQMLGLL |

METHODS AND MATERIALS FOR THE PRODUCTION OF MONOMERS FOR NYLON-4/POLYESTER PRODUCTION

CROSS-REFERENCE TO RELATED APPLICATIONS

This application is a division of U.S. application Ser. No. 14/976,966, filed Dec. 21, 2015, which claims the benefit of U.S. Provisional Application No. 62/095,556, filed Dec. 22, 2014, each of which is incorporated by reference herein in its entirety.

REFERENCE TO SEQUENCE LISTING SUBMITTED ELECTRONICALLY

An official copy of the sequence listing is submitted electronically via EFS-Web as an ASCII formatted sequence listing with a file named "SequenceListing.txt," submitted Dec. 21, 2015, in parent U.S. application Ser. No. 14/976,966, and having a size of 112,269 bytes. The sequence listing contained in this ASCII formatted document is part of the specification and is herein incorporated by reference in its entirety.

TECHNICAL FIELD

This invention relates to methods and materials for biosynthesizing one or more C4 building blocks. This invention relates to methods and materials for biosynthesizing one or more C4 building blocks such as 4-hydroxybutyrate, 4-aminobutyrate, putrescine, and 1,4-butanediol using one or more polypeptides having decarboxylase, dehydrogenase, synthase, reductase, or ω-transaminase activity, and recombinant hosts that produce such C4 building blocks.

BACKGROUND

Four carbon compounds such as 1,4-butanediol (also known as butane-1,4-diol or tetramethylene glycol), putrescine, 4-hydroxybutyrate, and gamma 4-aminobutyrate (GABA) are used, for example, for producing plastics and polymers. 1,4-butanediol is used, for example, as a solvent and for producing plastics, Spandex fibers, and polymers such as polyurethane. 1,4-butanediol can be produced from malic anhydride by the Davy process, from acetylene using Reppe chemistry, or from propylene oxide in a multi-step process. Putrescine is used to produce Nylon-4,6 by reacting with adipic acid. Putrescine typically is produced by hydrogenating succinonitrile. However, the methods to produce such compounds typically are energy intensive and/or produce large amounts of by-products.

SUMMARY

There is a need for sustainable and efficient methods for producing 1,4-butanediol, putrescine, 4-hydroxybutyrate, and 4-aminobutyrate This document is based at least in part on the discovery that it is possible to construct biochemical pathways for producing a four carbon chain backbone precursor via decarboxylation of 2-oxoglutarate or L-glutamate, and forming one or two functional groups, i.e., amine or hydroxyl, in the four carbon chain backbone precursor, leading to the synthesis of one or more of 4-hydroxybutyrate, 4-aminobutyrate, putrescine (also known as tetramethylenediamine), and 1,4-butanediol (hereafter collectively referred to as "C4 building blocks" and each of the compounds being a "C4 building block"). Succinate semialdehyde (also known as 4-oxobutanoic acid) can be produced as an intermediate to other products. 4-hydroxybutyrate and 4-hydroxybutyric acid, 4-oxobutanoic acid and 4-oxobutanoate, and 4-aminobutyrate and 4-aminobutanoic acid are used interchangeably herein to refer to the compound in any of its neutral or ionized forms, including any salt forms thereof. It is understood by those skilled in the art that the specific form will depend on pH.

In one aspect, this document features a method of producing 1,4-butanediol. The method includes enzymatically converting 4-hydroxybutyrate to 1,4 butanediol using a carboxylate reductase and an alcohol dehydrogenase. The 4-hydroxybutyrate can be enzymatically synthesized from L-glutamate or 2-oxoglutarate. For example, 4-hydroxybutyrate can be enzymatically synthesized from L-glutamate by enzymatically converting L-glutamate to 4-aminobutyrate, enzymatically converting 4-aminobutyrate to succinate semialdehyde, and enzymatically converting succinate semialdehyde to 4-hydroxybutyrate. For example, L-glutamate can be enzymatically converted to 4-hydroxybutyrate using (i) a glutamate decarboxylase; (ii) a ω-transaminase; and (iii) a dehydrogenase selected from the group consisting of a 4-hydroxybutyrate dehydrogenase and a 5-hydroxyvalerate dehydrogenase. For example, 4-hydroxybutyrate can be enzymatically synthesized from 2-oxoglutarate by, for example, enzymatically converting 2-oxoglutarate to succinate semialdehyde and enzymatically converting succinate semialdehyde to 4-hydroxybutyrate. For example, 2-oxoglutarate can be enzymatically converted to succinate semialdehyde using a 2-oxoglutarate decarboxylase and/or succinate semialdehyde can be enzymatically converted to 4-hydroxybutyrate using a 4-hydroxybutyrate dehydrogenase or a 5-hydroxyvalerate dehydrogenase. 2-oxoglutarate also can be enzymatically converted to L-glutamate, L-glutamate can be enzymatically converted to 4-aminobutyrate, 4-aminobutyrate can be enzymatically converted to succinate semialdehyde, and succinate semialdehyde can be enzymatically converted to 4-hydroxybutyrate.

This document also features a method of producing 4-hydroxybutyrate. The method includes enzymatically synthesizing 4-hydroxybutyrate from L-glutamate. L-glutamate can be enzymatically converted to 4-aminobutyrate, 4-aminobutyrate can be enzymatically converted to succinate semialdehyde, and succinate semialdehyde can be enzymatically converted to 4-hydroxybutyrate.

This document also features a method of producing putrescine, said method comprising a) enzymatically converting 4-hydroxybutyrate to putrescine using a carboxylate reductase, an alcohol dehydrogenase, and at least one ω-transaminase, or b) enzymatically converting 4-aminobutyrate to putrescine using a carboxylate reductase and a ω-transaminase.

This document also features a method of producing putrescine. The method includes enzymatically converting 1,4 butanediol to putrescine using at least one alcohol dehydrogenase and at least one ω-transaminase.

In any of the methods, L-glutamate can be enzymatically converted to 4-aminobutyrate using a glutamate decarboxylase having at least 70% sequence identity to the amino acid sequence set forth in SEQ ID NO:14 or SEQ ID NO: 19.

In any of the methods, the carboxylate reductase can have at least 70% sequence identity to the amino acid sequence set forth in SEQ ID NO: 1, SEQ ID NO:2, SEQ ID NO:3, SEQ ID NO:4, or SEQ ID NO:5.

In any of the methods, the alcohol dehydrogenase can be classified under EC 1.1.1.1, EC 1.1.1.2, EC 1.1.1.21, or EC 1.1.1.184.

In any of the methods, the ω-transaminase can be classified under EC 2.6.1.18, EC 2.6.1.19, EC 2.6.1.29, 2.6.1.48, EC 2.6.1.76, EC 2.6.1.82, or EC 2.6.1.96. For example, the ω-transaminase can have at least 70% sequence identity to an amino acid sequence set forth in SEQ ID NO: 6, SEQ ID NO: 7, SEQ ID NO: 8, SEQ ID NO: 9, SEQ ID NO: 10, or SEQ ID NO: 11.

This document also features a recombinant host that includes at least one exogenous nucleic acid encoding (i) a glutamate decarboxylase, (ii) a dehydrogenase selected from the group consisting of a 4-hydroxybutyrate dehydrogenase and a 5-hydroxyvalerate dehydrogenase, and (iii) a first exogenous ω-transaminase, the host producing 4-hydroxybutyrate.

The host further can include an exogenous carboxylate reductase, a second optional and a third optional exogenous ω-transaminase, and an exogenous alcohol dehydrogenase, the host further producing putrescine.

The host further can include an exogenous carboxylate reductase and an exogenous alcohol dehydrogenase, the host further producing 1,4-butanediol.

This document also features a recombinant host that includes at least one exogenous nucleic acid encoding (i) a 2-oxoglutarate decarboxylase, (ii) a dehydrogenase, (iii) a carboxylate reductase, and (iv) an alcohol dehydrogenase, the host producing 1,4-butanediol. The dehydrogenase can be selected from the group consisting of a 5-hydroxyvalerate dehydrogenase and a 4-hydroxybutyrate dehydrogenase.

This document also features a recombinant host that includes at least one exogenous nucleic acid encoding a carboxylate reductase and at least one ω-transaminase, the host producing putrescine. In some cases, the host includes two exogenous ω-transaminases. In some cases, the host further includes at least one exogenous alcohol dehydrogenase (e.g., two exogenous alcohol dehydrogenases).

A host further can include an exogenous 2-oxoglutarate decarboxylase and an exogenous dehydrogenase.

A host further can include an exogenous glutamate synthase, an exogenous glutamate decarboxylase, a second exogenous ω-transaminase, and a dehydrogenase.

In any of the recombinant hosts, the at least one exogenous ω-transaminase can have at least 70% sequence identity to an amino acid sequence set forth in SEQ ID NO: 6, SEQ ID NO: 7, SEQ ID NO: 8, SEQ ID NO: 9, SEQ ID NO:10, or SEQ ID NO: 11.

In any of the recombinant hosts, the carboxylate reductase can have at least 70% sequence identity to the amino acid sequence set forth in SEQ ID NO:1, SEQ ID NO:2, SEQ ID NO:3, SEQ ID NO:5, or SEQ ID NO:6.

In any of the methods, all or part of the method can be performed in a recombinant host by fermentation. The host can be subjected to a cultivation strategy under aerobic, anaerobic or, micro-aerobic cultivation conditions. The host can be cultured under conditions of nutrient limitation. The host can be retained using a ceramic hollow fiber membrane to maintain a high cell density during fermentation. The principal carbon source fed to the fermentation can derive from a biological feedstock. For example, the biological feedstock can be, or can derive from, monosaccharides, disaccharides, lignocellulose, hemicellulose, cellulose, lignin, levulinic acid, formic acid, triglycerides, glycerol, fatty acids, agricultural waste, condensed distillers' solubles, or municipal waste. The principal carbon source fed to the fermentation can derive from a non-biological feedstock.

For example, the non-biological feedstock can be, or can derive from, natural gas, syngas, $CO_2/H_2$, methanol, ethanol, benzoate, non-volatile residue (NVR) caustic wash waste stream from cyclohexane oxidation processes, or terephthalic acid/isophthalic acid mixture waste streams.

Any of the recombinant hosts or any of the recombinant hosts used in any of the methods can be a prokaryote. The prokaryote can be from the genus *Escherichia* such as *Escherichia coli*; from the genus *Clostridia* such as *Clostridium ljungdahlii, Clostridium autoethanogemim* or *Clostridium khlyveri*; from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens, Pseudomonas putida* or *Pseudomonas oleavorans*; from the genus *Delftia acidovorans*, from the genus *Bacillus* such as *Bacillus subtillis*; from the genes *Lactobacillus* such as *Lactobacillus delbrueckii*; from the genus *Lactococcus* such as *Lactococcus lactis* or from the genus *Rhodococcus* such as *Rhodococcus equi*.

Any of the recombinant hosts or any of the recombinant hosts used in any of the methods can be a eukaryote. The eukaryote can be from the genus *Aspergillus* such as *Aspergillus niger*; from the genus *Saccharomyces* such as *Saccharomyces cerevisiae*; from the genus *Pichia* such as *Pichia pastoris*; from the genus *Yarrowia* such as *Yarrowia lipolytica*, from the genus *Issatchenkia* such as *Issathenkia orientalis*, from the genus *Debaryomyces* such as *Debaryomyces hansenii*, from the genus *Arxula* such as *Arxula adenoinivorans*, or from the genus *Kluyveromyces* such as *Kluyveromyces lactis*.

The recombinant host or recombinant host used in any of the methods can include one or more of the following attenuated enzymes: a polyhydroxyalkanoate synthase; a triose phosphate isomerase; a glucose-6-phosphate isomerase; a transhydrogenase; an NADH-specific glutamate dehydrogenase; or a NADH/NADPH-utilizing glutamate dehydrogenase.

Any of the recombinant hosts or any of the recombinant hosts used in any of the methods can overexpress one or more genes encoding: a phosphoenolpyruvate carboxylase; a pyruvate carboxylase; a 6-phosphogluconate dehydrogenase; a transketolase; a puridine nucleotide transhydrogenase; a formate dehydrogenase; a glyceraldehyde-3P-dehydrogenase; a malic enzyme; a glucose dehydrogenase; a glucose-6-phosphate dehydrogenase; a fructose 1,6 diphosphatase; a L-alanine dehydrogenase; a L-glutamate dehydrogenase; a L-glutamine synthetase; a lysine transporter; a dicarboxylate transporter; and/or a multidrug transporter.

In one aspect, this document features a biochemical network comprising a carboxylate reductase and an alcohol dehydrogenase. 4-hydroxybutyrate, and 1,4 butanediol, wherein the carboxylate reductase and the alcohol dehydrogenase enzymatically convert 4-hydroxybutyrate to 1,4-butanediol. The biochemical network further can include a glutamate decarboxylase; a ω-transaminase; and a dehydrogenase selected from the group consisting of a 4-hydroxybutyrate dehydrogenase and a 5-hydroxyvalerate dehydrogenase, wherein the glutamate decarboxylase, the ω-transaminase, and the dehydrogenase enzymatically convert L-glutamate to 4-hydroxybutyrate.

This document also features a means for producing 1,4 butanediol, wherein the means enzymatically converts 4-hydroxybutyrate to 1,4 butanediol. The means can include a carboxylate reductase and an alcohol dehydrogenase.

This document also features a means for producing putrescine, wherein the means enzymatically converts 4-hydroxybutyrate to putrescine. The means can include a carboxylate reductase, an alcohol dehydrogenase, and at least one ω-transaminase.

In another aspect, this document features a step for obtaining 1,4-butanediol using a carboxylate reductase and an alcohol dehydrogenase.

This document also features a composition comprising 4-hydroxybutyrate, bio 1,4 butanediol, and a carboxylate reductase and an alcohol dehydrogenase. The composition can be cellular or acellular.

This document also features a composition comprising 4-hydroxybutyrate, bio putrescine, and a carboxylate reductase, an alcohol dehydrogenase, and at least one ω-transaminase. The composition can be cellular or acellular.

In another aspect, this document features a bio 1,4 butanediol produced by the method of enzymatically converting 4-hydroxybutyrate to 1,4 butanediol using a carboxylate reductase and an alcohol dehydrogenase.

This document also features a bio putrescine produced by the method of enzymatically converting 4-hydroxybutyrate to putrescine using a carboxylate reductase, an alcohol dehydrogenase, and at least one ω-transaminase.

The reactions of the pathways described herein can be performed in one or more cell (e.g., host cell) strains (a) naturally expressing one or more relevant enzymes, (b) genetically engineered to express one or more relevant enzymes, or (c) naturally expressing one or more relevant enzymes and genetically engineered to express one or more relevant enzymes. Alternatively, relevant enzymes can be extracted from any of the above types of host cells and used in a purified or semi-purified form. Extracted enzymes optionally can be immobilized to the floors and/or walls of appropriate reaction vessels. Moreover, such extracts include lysates (e.g. cell lysates), and partially purified lysates, that can be used as sources of relevant enzymes. In the methods provided by the document, all the steps can be performed in cells (e.g., host cells), all the steps can be performed using extracted enzymes, or some of the steps can be performed in cells and others can be performed using extracted enzymes. In any of the methods, the reaction may be a single step conversion in which one compound is directly converted to a different compound of interest (e.g., L-glutamate to 4-aminobutyrate), or the conversion may include two or more steps to convert one compound to a different compound.

Many of the enzymes described herein catalyze reversible reactions, and the reaction of interest may be the reverse of the described reaction. The schematic pathways shown in FIGS. 1 to 4 illustrate the reaction of interest for each of the intermediates.

In one aspect, this document features a method for producing a bioderived four carbon compound. The method for producing a bioderived four carbon compound can include culturing or growing a recombinant host as described herein under conditions and for a sufficient period of time to produce the bioderived four carbon compound, wherein, optionally, the bioderived four carbon compound is selected from the group consisting of 4-hydroxybutyrate, 4-aminobutyrate, putrescine, and 1,4-butanediol, and combinations thereof.

In one aspect, this document features composition comprising a bioderived four carbon compound as described herein and a compound other than the bioderived four carbon compound, wherein the bioderived four carbon compound is selected from the group consisting of 4-hydroxybutyrate, 4-aminobutyrate, putrescine, and 1,4-butanediol, and combinations thereof. For example, the bioderived four carbon compound is a cellular portion of a host cell or an organism.

This document also features a biobased polymer comprising the b4-hydroxybutyrate, 4-aminobutyrate, putrescine, and 1,4-butanediol, and combinations thereof.

This document also features a biobased resin comprising the 4-hydroxybutyrate, 4-aminobutyrate, putrescine, and 1,4-butanediol, and combinations thereof, as well as a molded product obtained by molding a biobased resin.

In another aspect, this document features a process for producing a biobased polymer that includes chemically reacting the bioderived 4-hydroxybutyrate, 4-aminobutyrate, putrescine, and 1,4-butanediol, with itself or another compound in a polymer producing reaction.

In another aspect, this document features a process for producing a biobased resin that includes chemically reacting the bioderived 4-hydroxybutyrate, 4-aminobutyrate, putrescine, and 1,4-butanediol, with itself or another compound in a resin producing reaction.

One of skill in the art understands that compounds containing carboxylic acid groups (including, but not limited to, organic monoacids, hydroxyacids, aminoacids, and dicarboxylic acids) are formed or converted to their ionic salt form when an acidic proton present in the parent compound either is replaced by a metal ion, e.g., an alkali metal ion, an alkaline earth ion, or an aluminum ion; or coordinates with an organic base. Acceptable organic bases include, but are not limited to, ethanolamine, diethanolamine, triethanolamine, tromethamine, N-methylglucamine, and the like. Acceptable inorganic bases include, but are not limited to, aluminum hydroxide, calcium hydroxide, potassium hydroxide, sodium carbonate, sodium hydroxide, and the like. A salt of the present invention is isolated as a salt or converted to the free acid by reducing the pH to below the pKa, through addition of acid or treatment with an acidic ion exchange resin.

In a another aspect, the disclosure provides a non-naturally occurring organism comprising at least one exogenous nucleic acid encoding at least one polypeptide having the activity of at least one enzyme depicted in any one of FIGS. 1 to 5.

In a another aspect, the disclosure provides a nucleic acid construct or expression vector comprising (a) a polynucleotide encoding a polypeptide having the activity of a glutamate decarboxylase, wherein the polynucleotide is operably linked to one or more heterologous control sequences that direct production of the polypeptide and wherein the polypeptide having the activity of a glutamate decarboxylase is selected from the group consisting of a polypeptide having at least 70% sequence identity to the polypeptide of SEQ ID NO: 14 or SEQ ID NO: 19; or (b) a polynucleotide encoding a polypeptide having the activity of a carboxylate reductase, wherein the polynucleotide is operably linked to one or more heterologous control sequences that direct production of the polypeptide and wherein the polypeptide having the activity of a carboxylate reductase is selected from the group consisting of a polypeptide having at least 70% sequence identity to the polypeptide of SEQ ID NO:1, SEQ ID NO:2, SEQ ID NO:3, SEQ ID NO:4, SEQ ID NO:5 or SEQ ID NO: 18; or (c) a polynucleotide encoding a polypeptide having the activity of ω-transaminase, wherein the polynucleotide is operably linked to one or more heterologous control sequences that direct production of the polypeptide and wherein the polypeptide having the activity of ω-transaminase is selected from the group consisting of a polypeptide having at least 70% sequence identity to the polypeptide of SEQ ID NO: 6, SEQ ID NO: 7, SEQ ID NO: 8, SEQ ID NO: 9, SEQ ID NO: 10, or SEQ ID NO: 11; or (d) a polynucleotide encoding a polypeptide having the activity of a phosphopantetheinyl transferase, wherein the polynucleotide is operably linked to one or more heterologous control sequences that direct production of the polypeptide and wherein the polypeptide having phosphopantetheinyl transferase is selected from the group consisting of a polypeptide having at least 70% sequence identity to the polypeptide of SEQ ID NO: 12 or 13; or (e) a polynucleotide encoding a polypeptide having the activity of a decarboxylase, wherein the polynucleotide is operably linked to one or more heterologous control sequences that direct production of the polypeptide and wherein the polypeptide having the activity of a decarboxylase is selected from the group consisting of a polypeptide having at least 70% sequence identity to the polypeptide of SEQ ID NO: 15, 16 or 17. The disclosure further provides a composition comprising the nucleic acid construct or expression vector as recited above.

One of skill in the art understands that compounds containing amine groups (including, but not limited to, organic amines, aminoacids, and diamines) are formed or converted to their ionic salt form, for example, by addition of an acidic proton to the amine to form the ammonium salt, formed with inorganic acids such as hydrochloric acid, hydrobromic acid, sulfuric acid, nitric acid, phosphoric acid, and the like; or formed with organic acids including, but not limited to, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. Acceptable inorganic bases include, but are not limited to, aluminum hydroxide, calcium hydroxide, potassium hydroxide, sodium carbonate, sodium hydroxide, and the like. A salt of the present invention is isolated as a salt or converted to the free amine by raising the pH to above the pKb through addition of base or treatment with a basic ion exchange resin.

One of skill in the art understands that compounds containing both amine groups and carboxylic acid groups (including, but not limited to, aminoacids) are formed or converted to their ionic salt form by either 1) acid addition salts, formed with inorganic acids including, but not limited to, hydrochloric acid, hydrobromic acid, sulfuric acid, nitric acid, phosphoric acid, and the like; or formed with organic acids including, but not limited to, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. Acceptable inorganic bases include, but are not limited to, aluminum hydroxide, calcium hydroxide, potassium hydroxide, sodium carbonate, sodium hydroxide, and the like, or 2) when an acidic proton present in the parent compound either is replaced by a metal ion, e.g., an alkali metal ion, an alkaline earth ion, or an aluminum ion; or coordinates with an organic base. Acceptable organic bases include, but are not limited to, ethanolamine, diethanolamine, triethanolamine, tromethamine, N-methylglucamine, and the like. Acceptable inorganic bases include, but are not limited to, aluminum hydroxide, calcium hydroxide, potassium hydroxide, sodium carbonate, sodium hydroxide, and the like. A salt can of the present invention is isolated as a salt or converted to the free acid by reducing the pH to below the pKa through addition of acid or treatment with an acidic ion exchange resin.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and the drawings, and from the claims. The word "comprising" in the claims may be replaced by "consisting essentially of" or with "consisting of," according to standard practice in patent law.

DESCRIPTION OF DRAWINGS

FIG. 5 contains the amino acid sequences of a *Mycobacterium marinum* carboxylate reductase (see Genbank Accession No. ACC40567.1, SEQ ID NO: 1), a *Mycobacterium smegmatis* carboxylate reductase (see Genbank Accession No. ABK71854.1, SEQ ID NO: 2), a *Segniliparus rugosus* carboxylate reductase (see Genbank Accession No. EFV11917.1, SEQ ID NO: 3), a *Mycobacterium massiliense* carboxylate reductase (see Genbank Accession No. EIV11143.1, SEQ ID NO: 4), a *Segniliparus rotundus* carboxylate reductase (see Genbank Accession No. ADG98140.1, SEQ ID NO: 5), a *Chromobacterium violaceum* ω-transaminase (see Genbank Accession No. AAQ59697.1, SEQ ID NO: 6), a *Pseudomonas aeruginosa* ω-transaminase (see Genbank Accession No. AAG08191.1, SEQ ID NO: 7), a *Pseudomonas syringae* ω-transaminase (see Genbank Accession No. AAY39893.1, SEQ ID NO: 8), a *Rhodobacter sphaeroides* ω-transaminase (see Genbank Accession No. ABA81135.1, SEQ ID NO: 9), an *Escherichia coli* ω-transaminase (see Genbank Accession No. AAA57874.1, SEQ ID NO: 10), a *Vibrio fluvialis* ω-transaminase (See Genbank Accession No. AEA39183.1, SEQ ID NO: 11), a *Bacillus subtilis* phosphopantetheinyl transferase (see Genbank Accession No. CAA44858.1, SEQ ID NO: 12), a *Nocardia* sp. NRRL 5646 phosphopantetheinyl transferase (see Genbank Accession No. AB183656.1, SEQ ID NO: 13), an *Escherichia coli* L-glulamate decarboxylase (see Genbank Accession No. AAA23833.1 (SEQ ID NO: 14) & AAA23834.1 (SEQ ID NO: 19)), a *Lactococcus lactis* α-ketoisovalerate decarboxylase (see Genbank Accession No. ADA65057.1, SEQ ID NO: 15), a *Mycobacterium smegmalis* 2-oxoglutarale decarboxylase (see Genbank Accession No. ABK74238.1, SEQ ID NO:16), a *Salmonella typhimurium* indolepyruvate decarboxylase (see Genbank Accession No. AHX78209.1, SEQ ID NO: 17) or a *Mycobacterium smegmatis* carboxylate reductase (see Genbank Accession No. ABK75684.1, SEQ ID NO:18).

DETAILED DESCRIPTION

Figure 1:
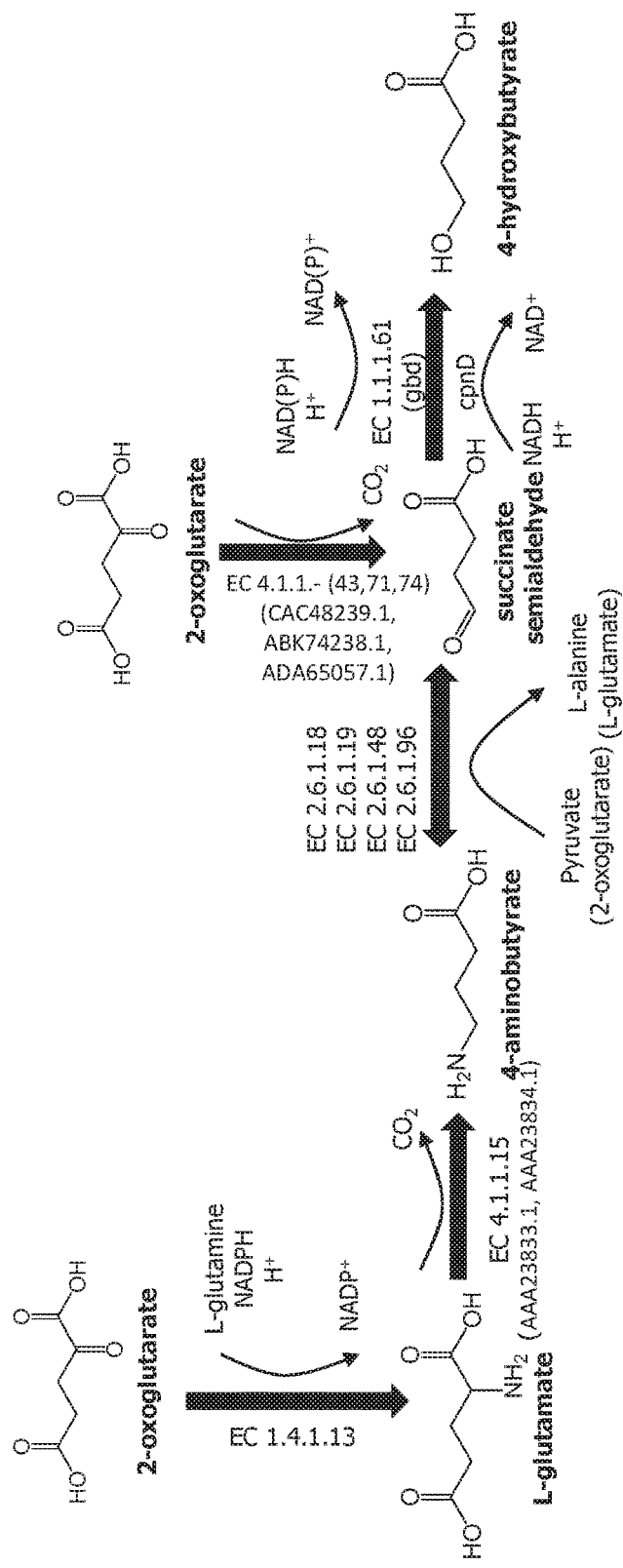
FIG. 1 is a schematic of exemplary biochemical pathways leading to 4-hydroxybutyrate using 2-oxoglutarate acid as a central metabolite.

This document provides enzymes, non-natural pathways, cultivation strategies, feedstocks, host microorganisms and attenuations to the host's biochemical network, which generates a four carbon chain backbone via decarboxylation of central metabolites such as 2-oxoglutarate or L-glutamate and in which one or two terminal functional groups may be formed leading to the synthesis of one or more of 4-hydroxybutyrate, 4-aminobutyrate, putrescine (also known as tetramethylenediamine), and 1,4-butanediol. Succinate semialdehyde can be produced as an intermediate to other products. As used herein, the term "central precursor" is used to denote any metabolite in any metabolic pathway shown herein leading to the synthesis of a C4 building block. The term "central metabolite" is used herein to denote a metabolite that is produced in all microorganisms to support growth.

Host microorganisms described herein can include endogenous pathways that can be manipulated such that one or more C4 building blocks can be produced. In an endogenous pathway, the host microorganism naturally expresses all of the enzymes catalyzing the reactions within the pathway. A host microorganism containing an engineered pathway does not naturally express all of the enzymes catalyzing the reactions within the pathway but has been engineered such that all of the enzymes within the pathway are expressed in the host.

The term "exogenous" as used herein with reference to a nucleic acid (or a protein) and a host refers to a nucleic acid that does not occur in (and cannot be obtained from) a cell of that particular type as it is found in nature or a protein encoded by such a nucleic acid. Thus, a non-naturally-occurring nucleic acid is considered to be exogenous to a host once in the host. It is important to note that non-naturally-occurring nucleic acids can contain nucleic acid subsequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular host microorganism. For example, an entire chromosome isolated from a cell of yeast x is an exogenous nucleic acid with respect to a cell of yeast y once that chromosome is introduced into a cell of yeast y.

In contrast, the term "endogenous" as used herein with reference to a nucleic acid (e.g., a gene) (or a protein) and a host refers to a nucleic acid (or protein) that does occur in (and can be obtained from) that particular host as it is found in nature. Moreover, a cell "endogenously expressing" a nucleic acid (or protein) expresses that nucleic acid (or protein) as does a host of the same particular type as it is found in nature. Moreover, a host "endogenously producing" or that "endogenously produces" a nucleic acid, protein, or other compound produces that nucleic acid, protein, or compound as does a host of the same particular type as it is found in nature.

For example, depending on the host and the compounds produced by the host, one or more of the following enzymes may be expressed in the host including a glutamate synthase, a glutamate decarboxylase, a 2-oxoghlarate decarboxylase, a 5-hydroxyvalerate dehydrogenase, an alcohol dehydrogenase, a 4-hydroxybutyrate dehydrogenase, a ω-transaminase, or a carboxylate reductase. In recombinant hosts expressing a carboxylate reductase, aphosphopantetheinyl transferase also can be expressed as it enhances activity of the carboxylate reductase.

In some embodiments, a recombinant host includes an exogenous glutamate synthase and produces L-glutamate.

In some embodiments, a recombinant host includes an exogenous glutamate synthase and an exogenous glutamate decarboxylase and produces 4-aminobutyrate.

In some embodiments, a recombinant host includes an exogenous glutamate decarboxylase and produces 4-aminobutyrate.

In some embodiments, a recombinant host producing 4-aminobutyrate includes at least one exogenous nucleic acid encoding a ω-transaminase and further produces succinate semialdehyde. For example, a recombinant host can include an exogenous glutamate decarboxylase, an exogenous ω-transaminase, and an optional an exogenous glutamate synthase, and further produce succinate semialdehyde.

In some embodiments, a recombinant host producing 4-aminobutyrate can include at least one exogenous nucleic acid encoding a ω-transaminase and a dehydrogenase such as a 4-hydroxybutyrate dehydrogenase or a 5-hydroxyvalerate dehydrogenase, and further produce 4-hydroxybuytrate. For example, a recombinant host can include an exogenous glutamate decarboxylase, an exogenous ω-transaminase, an exogenous dehydrogenase, and an optional exogenous glutamate synthase, and further produce 4-hydroxybutyrate.

In some embodiments, a recombinant host can include an exogenous 2-oxoglutarate decarboxylase and an exogenous dehydrogenase such as a 4-hydroxybutyrate dehydrogenase or a 5-hydroxyvalerate dehydrogenase, and produce 4-hydroxybutyrate. Such a host further can include an exogenous carboxylate reductase and an exogenous alcohol dehydrogenase, and further produce 1,4-butanediol.

A recombinant host producing 4-aminobutyrate, 4-hydroxybutyrate, or succinate semialdehyde can include one or more of an exogenous carboxylate reductase, an exogenous ω transaminase, or an exogenous alcohol dehydrogenase, and one or more (e.g., one, two, or three) optional exogenous enzymes such as a decarboxylase, dehydrogenase and/or a synthase, and produce putrescine.

In some embodiments, a recombinant host can include each of an exogenous carboxylate reductase and an exogenous ω-transaminase and produce putrescine. In some embodiments, a recombinant host can include each of an exogenous carboxylate reductase, an exogenous ω-transaminase, and an exogenous glutamate decarboxylase and produce putrescine.

In some embodiments, a recombinant host can include each of an exogenous carboxylate reductase, an exogenous ω-transaminase, an exogenous glutamate synthase, and an exogenous glutamate decarboxylase and produce putrescine.

In some embodiments, a recombinant host can include each of an exogenous carboxylate reductase, at least one exogenous ω-transaminase (e.g., two different exogenous ω-transaminases), an exogenous alcohol dehydrogenase, and produce putrescine.

In some embodiments, a recombinant host can include each of an exogenous carboxylate reductase, at least one exogenous ω-transaminase (e.g., two or three different exogenous ω-transaminases), an exogenous alcohol dehydrogenase, an exogenous 4-hydroxybutyrate dehydrogenase or an exogenous 5-hydroxyvalerate dehydrogenase, and an exogenous 2-oxoglutarate decarboxylase and produce putrescine.

In some embodiments, a recombinant host can include each of an exogenous carboxylate reductase, at least one exogenous ω-transaminase (e.g., two or three different exogenous ω-transaminases), an exogenous alcohol dehydrogenase, an exogenous 4-hydroxybutyrate dehydrogenase or an exogenous 5-hydroxyvalerate dehydrogenase, an exogenous glutamate decarboxylase, and an optional glutamate synthase, and produce putrescine.

A recombinant host producing 4-hydroxybutyrate can include one or more of a carboxylate reductase and an alcohol dehydrogenase, and produce 1,4-butanediol. A recombinant host producing 1,4-butanediol can include at least one exogenous ω-transaminase (e.g., one exogenous ω-transaminase or two different exogenous ω-transaminases) and optional second and/or third exogenous alcohol dehydrogenases and produce putrescine.

Within an engineered pathway, the enzymes can be from a single source, i.e., from one species or genus, or can be from multiple sources, i.e., different species or genera. Nucleic acids encoding the enzymes described herein have been identified from various organisms and are readily available in publicly available databases such as GenBank or EMBL.

As used herein, references to a particular enzyme (e.g. ω-transaminase) means a polypeptide having the activity of the particular enzyme (e.g. a polypeptide ω-transaminase activity).

Any of the enzymes described herein that can be used for production of one or more C4 building blocks can have at least 70% sequence identity (homology) (e.g., at least 75%, 80%, 85%, 90%, 91%, 92%, 93%, 95%, 96%, 97%, 98%, 99%, or 100%) to the amino acid sequence of the corresponding wild-type enzyme. It will be appreciated that the sequence identity can be determined on the basis of the mature enzyme (e.g., with any signal sequence removed) or on the basis of the immature enzyme (e.g., with any signal sequence included). It also will be appreciated that the initial methionine residue may or may not be present on any of the enzyme sequences described herein.

For example, a carboxylate reductase described herein can have at least 70%/sequence identity (homology) (e.g., at least 75%, 80%, 85%, 90%, 91%, 92%, 93%, 95%, 96%, 97%, 98%, 99%, or 100%) to the amino acid sequence of a *Mycobacterium marinum* (see Genbank Accession No. ACC40567.1, SEQ ID NO: 1), a *Mycobacterium smegmatis* (see Genbank Accession No. ABK71854.1, SEQ ID NO: 2), a *Segniliparus rugosus* (see Genbank Accession No. EFV11917.1, SEQ ID NO: 3), a *Mycobacterium massiliense* (see Genbank Accession No. EIV11143.1, SEQ ID NO: 4), a *Segniliparus rotundus* (see Genbank Accession No. ADG98140.1, SEQ ID NO: 5), or a *Mycobacterium smegmalis* (see Genbank Accession No. ABK75684.1, SEQ ID NO: 18) carboxylate reductase. See, FIG. 5.

For example, a ω-transaminase described herein can have at least 70% sequence identity (homology) (e.g., at least 75%, 80%, 85%, 90%, 91%, 92%, 93%, 95%, 96%, 97%, 98%, 99%, or 100%) to the amino acid sequence of a *Chromobacterium violaceum* (see Genbank Accession No. AAQ59697.1, SEQ ID NO: 6), a *Pseudomonas aeruginosa* (see Genbank Accession No. AAG08191.1, SEQ ID NO: 7), a *Pseudomonas syringae* (see Genbank Accession No. AAY39893.1, SEQ ID NO: 8), a *Rhodobacter sphaeroides* (see Genbank Accession No. ABA81135.1, SEQ ID NO: 9), an *Escherichia coli* (see Genbank Accession No. AAA57874.1, SEQ ID NO: 10), or a *Vibrio fluvialis* (see Genbank Accession No. AEA39183.1, SEQ ID NO: 11) ω-transaminase. Some of these ω-transaminases are diamine ω-transaminases. See, FIG. 5.

For example, a phosphopantetheinyl transferase described herein can have at least 70% sequence identity (homology) (e.g., at least 75%, 80%, 85%, 90%, 91%, 92%, 93%, 95%, 96%, 97%, 98%, 99%, or 100%) to the amino acid sequence of a *Bacillus subtilis* phosphopantetheinyl transferase (see Genbank Accession No. CAA44858.1, SEQ ID NO: 12) or a *Nocardia* sp. NRRL 5646 phosphopanietheinyl transferase (see Genbank Accession No. ABI83656.1, SEQ ID NO:13). See FIG. 5.

For example, a decarboxylase described herein can have at least 70% sequence identity (homology) (e.g., at least 75%, 80%, 85%, 90%, 91%, 92%, 93%, 95%, 96%, 97%, 98%, 99%, or 100%) to the amino acid sequence of a *Escherichia coli* L-glutamate decarboxylase (see Genbank Accession No. AAA23833.1 (SEQ ID NO: 14) & AAA23834.1 (SEQ ID NO: 19)), a *Lactococcus lactis* α-ketoisovalerate decarboxylase (see Genbank Accession No. ADA65057.1, SEQ ID NO: 15), a *Mycobacterium smegmatis* 2-oxoglutarate decarboxylase (see Genbank Accession No. ABK74238.1, SEQ ID NO:16), or a *Salmo-* nella typhimurium indolepyruvate decarboxylase (see Genbank Accession No. AHX78209.1, SEQ ID NO: 17). See FIG. 5.

The percent identity (homology) between two amino acid sequences can be determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from Fish & Richardson's web site (e.g., worldwide web at .fr.com/blast/) or the U.S. government's National Center for Biotechnology Information web site (worldwide web at ncbi.nlm.nih.gov). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology (identity), then the designated output file will present those regions of homology as aligned sequences. If the two compared sequences do not share homology (identity), then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity (homology) is determined by dividing the number of matches by the length of the full-length polypeptide amino acid sequence followed by multiplying the resulting value by 100. It is noted that the percent identity (homology) value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

Functional fragments of any of the enzymes described herein can also be used in the methods of the document. The term "functional fragment" as used herein refers to a peptide fragment of a protein that has at least 25% (e.g., at least: 30%; 40%; 50%; 60%; 70%; 75%; 80%; 85%; 90%; 95%; 98%; 99%; 100%; or even greater than 100%) of the activity of the corresponding mature, full-length, wild-type protein. The functional fragment can generally, but not always, be comprised of a continuous region of the protein, wherein the region has functional activity.

This document also provides (i) functional variants of the enzymes used in the methods of the document and (ii) functional variants of the functional fragments described above. Functional variants of the enzymes and functional fragments can contain additions, deletions, or substitutions relative to the corresponding wild-type sequences. Enzymes with substitutions will generally have not more than 50 (e.g., not more than one, two, three, four, five, six, seven, eight, nine, ten, 12, 15, 20, 25, 30, 35, 40, or 50) amino acid substitutions (e.g., conservative substitutions). This applies to any of the enzymes described herein and functional fragments. A conservative substitution is a substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution. By contrast, a nonconservative substitution is a substitution of one amino acid for another with dissimilar characteristics.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. Additions (addition variants) include fusion proteins containing: (a) any of the enzymes described herein or a fragment thereof; and (b) internal or terminal (C or N) irrelevant or heterologous amino acid sequences. In the context of such fusion proteins, the term "heterologous amino acid sequences" refers to an amino acid sequence other than (a). A heterologous sequence can be, for example a sequence used for purification of the recombinant protein (e.g., FLAG, polyhistidine (e.g., hexahistidine), hemagglutinin (HA), glutathione-S-transferase (GST), or maltosebinding protein (MBP)). Heterologous sequences also can be proteins useful as detectable markers, for example, luciferase, green fluorescent protein (GFP), or chloramphenicol acetyl transferase (CAT). In some embodiments, the fusion protein contains a signal sequence from another protein. In certain host cells (e.g., yeast host cells), expression and/or secretion of the target protein can be increased through use of a heterologous signal sequence. In some embodiments, the fusion protein can contain a carrier (e.g., KLH) useful, e.g., in eliciting an immune response for antibody generation) or ER or Golgi apparatus retention signals. Heterologous sequences can be of varying length and in some cases can be a longer sequences than the full-length target proteins to which the heterologous sequences are attached.

Engineered hosts can naturally express none or some (e.g., one or more, two or more, three or more, four or more, five or more, or six or more) of the enzymes of the pathways described herein in FIG. 1, 2, 3, or 4. Thus, a pathway within an engineered host can include all exogenous enzymes, or can include both endogenous and exogenous enzymes. Endogenous genes of the engineered hosts also can be disrupted to prevent the formation of undesirable metabolites or prevent the loss of intermediates in the pathway through other enzymes acting on such intermediates. Engineered hosts can be referred to as recombinant hosts or recombinant host cells. As described herein recombinant hosts can include nucleic acids encoding one or more of a reductase, decarboxylase, synthase, dehydrogenase, or ω-transaminase as described herein.

In addition, the production of one or more C4 building blocks can be performed in vitro using the isolated enzymes described herein, using a lysate (e.g., a cell lysate) from a host microorganism as a source of the enzymes, or using a plurality of lysates from different host microorganisms as the source of the enzymes.

Figure 4:
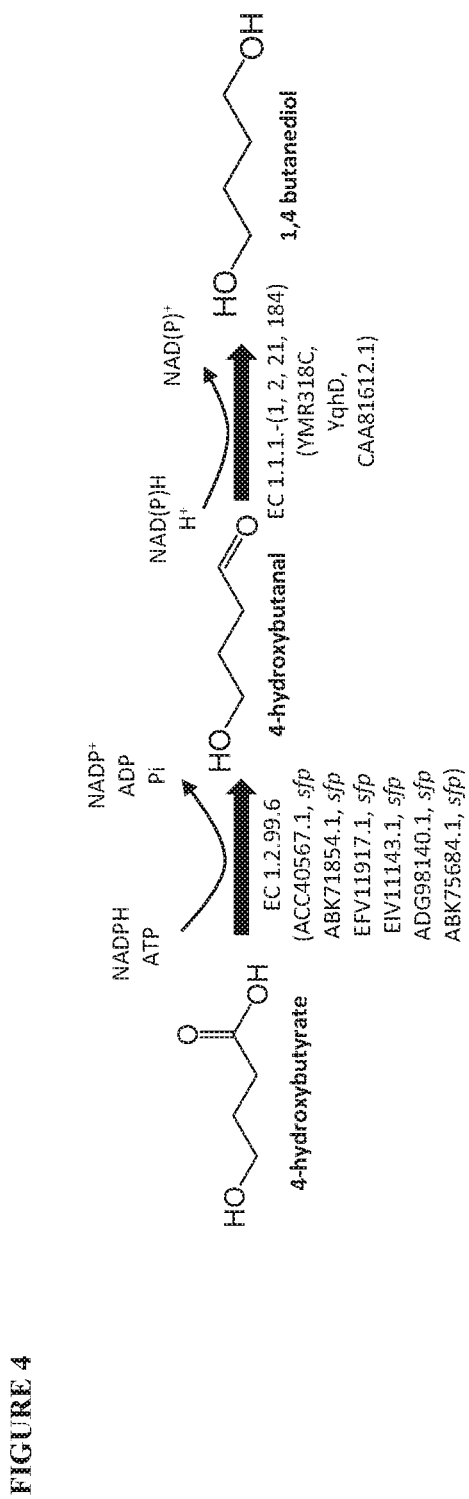
FIG. 4 is a schematic of an exemplary biochemical pathway leading to 1,4 butanediol using 4-hydroxybutyrate as a central precursor.

Enzymes Generating the Terminal Hydroxyl Group in the Biosynthesis of a C4 Building Block As depicted in FIGS. 1 and 4, a terminal hydroxyl group can be enzymatically formed using a dehydrogenase such as an alcohol dehydrogenase, a 5-hydroxyvalerate dehydrogenase, or a 4-hydroxybutyrate dehydrogenase.

For example, a terminal hydroxyl group leading to the synthesis of 4-hydroxybutyrate can be enzymatically formed by a dehydrogenase classified, for example, under EC 1.1.1.—such as a 5-hydroxyvalerate dehydrogenase (also known as 5-hydroxypentanoate dehydrogenase), for example, the gene product of CpnD (see, for example, Iwaki et al., 2002, *Appl. Environ. Microbiol.*, 68(11):5671-5684), a 5-hydroxyvalerate dehydrogenase from *Clostridium viride*, or a 4-hydroxybutyrate dehydrogenase classified under EC 1.1.1.61 such as gbd (see, for example, Lütke-Eversloh & Steinbüchel, 1999, *FEMS Microbiology Letters*, 181(1):63-71). See, FIG. 1.

A terminal hydroxyl group leading to the synthesis of 1,4 butanediol can be enzymatically formed by an alcohol dehydrogenase classified under EC 1.1.1.—(e.g., EC 1.1.1.1, 1.1.1.2, 1.1.1.21, or 1.1.1.184). See, FIG. 4.

Figure 2:
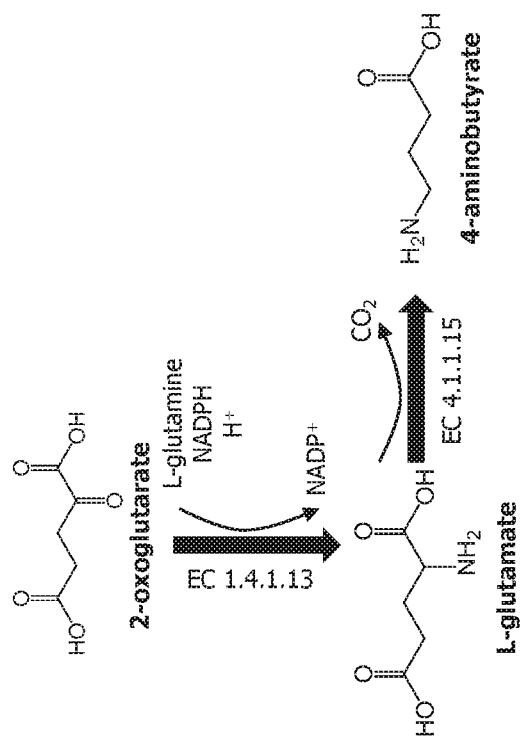
FIG. 2 is a schematic of an exemplary biochemical pathway leading to 4-aminobutyrate using 2-oxoglutarate acid as a central precursor.
Figure 3:
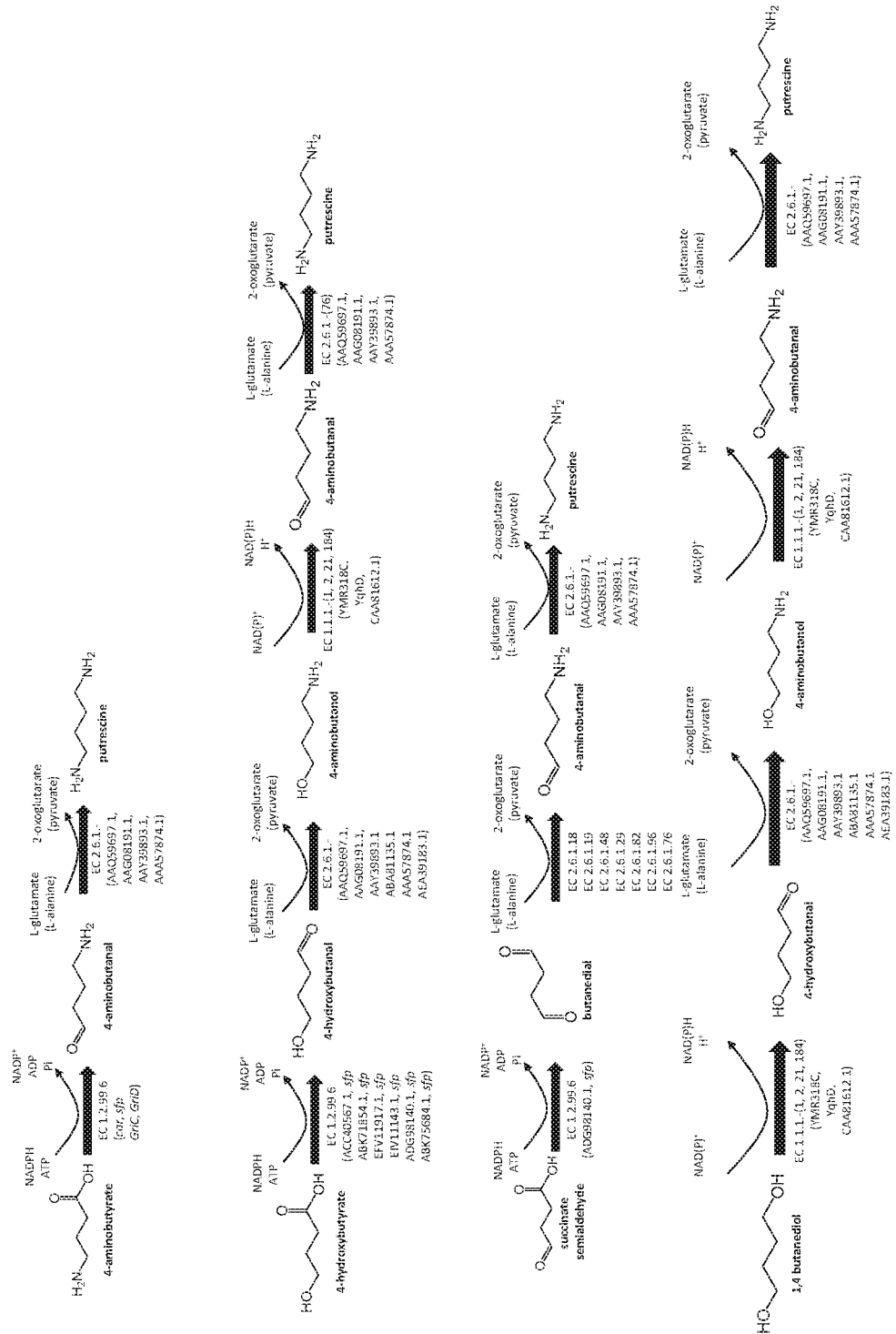
FIG. 3 is a schematic of exemplary biochemical pathways leading to putrescine using 4-aminobutyrate, 4-hydroxybutyrate, succinate semialdehyde, or 1,4-butanediol as a central precursor.

Enzymes Generating the Terminal Amine Groups in the Biosynthesis of a C4 Building Block As depicted in FIGS. 1-3, terminal amine groups can be enzymatically formed using a ω-transaminase or a glutamate decarboxylase.

In some embodiments, one terminal amine group is enzymatically formed by a glutamate decarboxylase classified, for example, under EC 4.1.1.15, producing 4-aminobutyrate. See, FIGS. 1 and 2.

In some embodiments, one terminal amine group leading to the synthesis of putrescine can be enzymatically formed by a ω-transaminase classified, for example, under EC 2.6.1.18, EC 2.6.1.19, EC 2.6.1.29, EC 2.6.1.48, or EC 2.6.1.82 such as that obtained from *Chromobacterium violaceum* (Genbank Accession No. AAQ59697.1, SEQ ID NO: 6), *Pseudomonas aeruginosa* (Genbank Accession No. AAG08191.1, SEQ ID NO: 7), *Pseudomonas syringae* (Genbank Accession No. AAY39893.1, SEQ ID NO: 8), *Rhodobacter sphaeroides* (Genbank Accession No. ABA81135.1, SEQ ID NO: 9), *Vibrio fluvialis* (Genbank Accession No. AEA39183.1, SEQ ID NO: 11), *Streptomyces griseus*, or *Clostridium viride*. An additional ω-transaminase that can be used in the methods and hosts described herein is from *Escherichia coli* (Genbank Accession No. AAA57874.1, SEQ ID NO: 10). Some of the ω-transaminases classified, for example, under EC 2.6.1.29 or EC 2.6.1.82 are diamine ω-transaminases (e.g., SEQ ID NO: 8). See, FIG. 3.

The reversible ω-transaminase from *Chromobacterium violaceum* (Genbank Accession No. AAQ59697.1, SEQ ID NO: 7) has demonstrated activity accepting 4-aminobutyric acid as amino donor, thus forming the first terminal amine group in succinate semialdehyde (Kaulmann et al., *Enzyme and Microbial Technology*, 2007, 41, 628-637).

The reversible 4-aminobutyrate:2-oxoglutarate transaminase from *Streptomyces griseus* has been characterized (Yonaha et al., *Eur. J. Biochem.*, 1985, 146, 101-106).

In some embodiments, the second terminal amine group leading to the synthesis of putrescine is enzymatically formed by a diamine transaminase. For example, the second terminal amino group can be enzymatically formed by a diamine transaminase classified, for example, under EC 2.6.1.29 or EC 2.6.1.76, or classified, for example, under EC 2.6.1.82, such as the gene product of YgjG from *E. coli* (Genbank Accession No. AAA57874.1, SEQ ID NO: 10).

The gene product of ygjG accepts a broad range of diamine carbon chain length substrates, including putrescine (Samsonova et al., *BMC Microbiology*, 2003, 3:2).

The diamine transaminase from *E. coli* strain B has demonstrated activity for 1,4 diaminobutane (Kim, *The Journal of Chemistry*, 1964, 239(3), 783-786).

Biochemical Pathways
Pathway to 4-Hydroxybutyrate

As depicted in FIG. 1, 2-oxoglutarate can be converted to L-glutamate by a glutamate synthase classified, for example, under EC 1.4.1.13; followed by conversion of L-glutamate to 4-aminobutyrate by a glutamate decarboxylase classified, for example, under EC 4.1.1.15 (see Genbank Accession No. AAA23833.1 (SEQ ID NO: 14) & AAA23834.1 (SEQ ID NO: 19)); followed by conversion of 4-aminobutyrate to succinate semialdehyde by a ω-transaminase classified, for example, under EC 2.6.1.18, EC 2.6.1.19, EC 2.6.1.48, or EC 2.6.1.96; followed by conversion of succinate semialdehyde to 4-hydroxybutyrate by a dehydrogenase classified, for example, under EC 1.1.1.—such as EC 1.1.1.61 (e.g., the gene product of gbd) or the gene product of cpnD.

As depicted in FIG. 1, 2-oxoglutarate can be converted to succinate semialdehyde using a 2-oxoglutarate decarboxylase classified, for example, under EC 4.1.1.43, EC 4.1.1.71, or EC 4.1.1.73, followed by conversion of succinate semialdehyde to 4-hydroxybutyrate by a dehydrogenase classified, for example, under EC 1.1.1.—such as EC 1.1.1.61 (e.g., the gene product of gbd) or the gene product of cpnD).

Pathway to 4-Aminobutyrate Using 2-Oxoglutarate as a Central Precursor

As depicted in FIG. 1, 2-oxoglutarate can be converted to succinate semialdehyde by a decarboxylase classified, for example, under EC 4.1.1.43, EC 4.1.1.71 or EC 4.1.1.74; followed by conversion of succinate semialdehyde to 4-aminobutyrate by a ω-transaminase classified, for example, under EC 2.6.1.—. The decarboxylase can be obtained, for example, from *Lactococcus lactis* α-ketoisovalerate decarboxylase (see Genbank Accession No. ADA65057.1, SEQ ID NO: 15), from *Mycobacterium smegmatis* 2-oxoglutarate decarboxylase (see Genbank Accession No. ABK74238.1, SEQ ID NO: 16) or from *Salmonella typhimurium* indolepyruvate decarboxylase (see Genbank Accession No. AHX78209.1, SEQ ID NO: 17).

As depicted in FIGS. 1 and 2, 2-oxoglutarate can be converted to L-glutamate by a glutamate synthase classified, for example, under EC 1.4.1.13; followed by conversion of L-glutamate to 4-aminobutyrate by a glutamate decarboxylase classified, for example, under EC 4.1.1.15.

Pathway Using 4-Aminobutyrate, 4-Hydroxybutyrate, Succinate Semialdehyde or 1,4-Butanediol as Central Precursor to Putrescine In some embodiments, putrescine is synthesized from the central precursor 4-aminobutyrate (which can be produced, for example, as described in FIG. 2) by conversion of 4-aminobutyrate to 4-aminobutanal by a carboxylate reductase classified, for example, under EC 1.2.99.6 such as the gene product of car in combination with a phosphopantetheine transferase enhancer (e.g., encoded by a sfp gene from *Bacillus subtilis* or npt gene from *Nocardia*, SEQ ID NOs:

12 and 13, respectively) or the gene products of GriC and GriD from *Streptomyces griseus* (Suzuki et al., *J. Antibiot.*, 2007, 60(6), 380-387); followed by conversion of 4-aminobutanal to putrescine by a ω-transaminase (e.g., EC 2.6.1.—such as one of SEQ ID NOs: 6, 7, 8, or 10). The carboxylate reductase can be obtained, for example, from *Mycobacterium marinum* (Genbank Accession No. ACC40567.1, SEQ ID NO: 1), *Mycobacterium smegmatis* (Genbank Accession No. ABK71854.1, SEQ ID NO: 2), *Segniliparus rugosus* (Genbank Accession No. EFV11917.1, SEQ ID NO: 3), *Mycobacterium massiliense* (Genbank Accession No. EIV11143.1, SEQ ID NO: 4), *Segniliparus rotundus* (Genbank Accession No. ADG98140.1, SEQ ID NO: 5), or *Mycobacterium smegmatis* (see Genbank Accession No. ABK75684.1, SEQ ID NO: 18). See FIG. 3.

The carboxylate reductase encoded by the gene product of car and enhancer npt or sfp has broad substrate specificity, including terminal difunctional C4 and C5 carboxylic acids (Venkitasubramanian et al., *Enzyme and Microbial Technology*, 2008, 42, 130-137).

In some embodiments, putrescine is synthesized from the central precursor 4-hydroxybutyrate (which can be produced, for example, as described in FIG. 1), by conversion of 4-hydroxybutyrate to 4-hydroxybutanal by a carboxylate reductase classified, for example, under EC 1.2.99.6 such as the gene product of car (see above, e.g., one of SEQ ID NOs. 1-5) in combination with a phosphopantetheine transferase enhancer (see above); followed by conversion of 4-hydroxybutanal to 4-aminobutanol by a ω-transaminase classified, for example, under EC 2.6.1.18, EC 2.6.1.19, EC 2.6.1.29, EC 2.6.1.48, or EC 2.6.1.82 such as SEQ ID NOs:6-11, see above; followed by conversion to 4-aminobutanal by an alcohol dehydrogenase classified, for example, under EC 1.1.1.—(e.g., EC 1.1.1.1, EC 1.1.1.2, EC 1.1.1.21, or EC 1.1.1.184) such as the gene product of YMR318C or YqhD (Liu et al., *Microbiology*, 2009, 155, 2078-2085; Larroy et al., 2002, *Biochem J.*, 361(Pt 1), 163-172; Jarboe, 2011, *Appl. Microbiol. Biotechnol.*, 89(2), 249-257) or the protein having GenBank Accession No. CAA81612.1; followed by conversion to putrescine by a ω-transaminase classified, for example, under EC 2.6.1.18, EC 2.6.1.19, EC 2.6.1.29, EC 2.6.1.48, or EC 2.6.1.82 such as one of SEQ ID NOs: 6-8 and 10, see above. See FIG. 3.

In some embodiments, putrescine is synthesized from the central precursor succinate semialdehyde (also known as 4-oxobutanoate) by conversion of succinate semialdehyde to butanedial by a carboxylate reductase classified, for example, under EC 1.2.99.6 such as the gene product of car (see above, e.g., SEQ ID NO: 5) in combination with a phosphopantelheine transferase enhancer (see above); followed by conversion to 4-aminobutanal by a ω-transaminase classified, for example, under EC 2.6.1.18, EC 2.6.1.19, or EC 2.6.1.48; followed by conversion of 4-aminobutanal to putrescine by a ω-transaminase classified, for example, under EC 2.6.1.—such as one of SEQ ID NOs: 6-8 and 10. See FIG. 3.

In some embodiments, putrescine is synthesized from the central precursor 1,4-butanediol (which can be produced, for example, as described in FIG. 4), by conversion of 1,4-butanediol to 4-hydroxybutanal by an alcohol dehydrogenase classified, for example, under EC 1.1.1.—such as EC 1.1.1.1, EC 1.1.1.2, EC 1.1.1.21, or EC 1.1.1.184) such as the gene product of YIMR318C or YqhD (from *E. coli*, GenBank Accession No. AAA69178.1) (see, e.g., Liu et al., *Microbiology*, 2009, 155, 2078-2085; Larroy et al., 2002, *Biochem J.*, 361(Pt 1), 163-172; or Jarboe, 2011, *Appl. Microbiol. Biotechnol.*, 89(2), 249-257) or the protein having GenBank Accession No. CAA81612.1 (from *Geobacillus stearothermophilus*); followed by conversion of 4-hydroxybutanal to 4-aminobutanol by a ω-transaminase classified, for example, under EC 2.6.1.18, EC 2.6.1.19, EC 2.6.1.29, EC 2.6.1.48, or EC 2.6.1.82 such as SEQ ID NOs:6-11, see above; followed by conversion to 4-aminobutanal by an alcohol dehydrogenase classified, for example, under EC 1.1.1.—(e.g., EC 1.1.1.1, EC 1.1.1.2, EC 1.1.1.21, or EC 1.1.1.184) such as the gene product of YMR318C or YqhD (Liu et al., *Microbiology*, 2009, 155, 2078-2085; Larroy et al., 2002, *Biochem J.*, 361(Pt 1), 163-172; Jarboe, 2011, *Appl. Microbiol. Biotechnol.*, 89(2), 249-257) or the protein having GenBank Accession No. CAA81612.1; followed by conversion to putrescine by a ω-transaminase classified, for example, under EC 2.6.1.—such as one of SEQ ID NOs:6-8 or 10, see above. See FIG. 3.

Pathway to 1,4-Butanediol Using 4-Hydroxybutyrate as Central Precursor

As depicted in FIG. 4, 1,4 butanediol can be synthesized from the central precursor 4-hydroxybutyrate by conversion of 4-hydroxybutyrate to 4-hydroxybutanal by a carboxylate reductase classified, for example, under EC 1.2.99.6 such as the gene product of car (see above, e.g., one of SEQ ID NOs: 1-5) in combination with a phosphopantelheine transferase enhancer (see above); followed by conversion of 4-hydroxybutanal to 1,4 butanediol by an alcohol dehydrogenase classified, for example, under EC 1.1.1.—such as EC 1.1.1.1, EC 1.1.1.2, EC 1.1.1.21, or EC 1.1.1.184 such as the gene product of YMR318C or YqhD (from *E. coli*, GenBank Accession No. AAA69178.1) (see, e.g., Liu et al., *Microbiology*, 2009, 155, 2078-2085; Larroy et al., 2002, *Biochem J.*, 361(Pt 1), 163-172; or Jarboe, 2011, *Appl. Microbiol. Biotechnol.*, 89(2), 249-257) or the protein having GenBank Accession No. CAA81612.1 (from *Geobacillus stearothermophilus*). See, FIG. 5 for the amino acid sequences of the above proteins.

Cultivation Strategy

In some embodiments, a cultivation strategy entails either achieving an anaerobic, aerobic or micro-aerobic cultivation condition.

In some embodiments, the cultivation strategy entails nutrient limitation such as nitrogen, phosphate or oxygen limitation.

In some embodiments, a cell retention strategy using, for example, ceramic hollow fiber membranes can be employed to achieve and maintain a high cell density during either fed-batch or continuous fermentation.

In some embodiments, the principal carbon source fed to the fermentation in the synthesis of one or more C4 building blocks can derive from biological or non-biological feedstocks.

In some embodiments, the biological feedstock can be or can derive from, monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

The efficient catabolism of crude glycerol stemming from the production of biodiesel has been demonstrated in several microorganisms such as *Escherichia coli, Cupriavidus necator, Pseudomonas oleavorans, Pseudomonas putida* and *Yarrowia lipolytica* (Lee et al., *Appl. Biochem. Biotechnol.*, 2012, 166:1801-1813; Yang et al., *Biotechnology for Biofuels*, 2012, 5:13; Meijnen et al., *Appl. Microbiol. Biotechnol.*, 2011, 90:885-893).

The efficient catabolism of lignocellulosic-derived levulinic acid has been demonstrated in several organisms such as *Cupriavidus* necator and *Pseudomonas putida* in the synthesis of 3-hydroxyvalerate via the precursor propanoyl-CoA (Jaremko and Yu, 2011, supra; Martin and Prather, *J. Biotechnol.*, 2009, 139:61-67).

The efficient catabolism of lignin-derived aromatic compounds such as benzoate analogues has been demonstrated in several microorganisms such as *Pseudomonas putida*, *Cupriavidus necator* (Bugg et al., *Current Opinion in Biotechnology*, 2011, 22, 394-400; Pérez-Pantoja et al., *FEMS Microbiol. Rev.*, 2008, 32, 736-794).

The efficient utilization of agricultural waste, such as olive mill waste water has been demonstrated in several microorganisms, including *Yarrowia lipolytica* (Papanikolaou et al., *Bioresour. Technol.*, 2008, 99(7):2419-2428).

The efficient utilization of fermentable sugars such as monosaccharides and disaccharides derived from cellulosic, hemicellulosic, cane and beet molasses, cassava, corn and other agricultural sources has been demonstrated for several microorganism such as *Escherichia coli, Corynebacterium glutamicum* and *Lactobacillus delbrueckii* and *Lactococcus lactis* (see, e.g., Hermann et al, *J. Biotechnol.*, 2003, 104: 155-172; Wee et al., *Food Technol. Biotechnol.*, 2006, 44(2): 163-172; Ohashi et al., *J. Bioscience and Bioengineering*, 1999, 87(5):647-654).

The efficient utilization of furfural, derived from a variety of agricultural lignocellulosic sources, has been demonstrated for *Cupriavidus necator* (Li et al., *Biodegradation*, 2011, 22:1215-1225).

In some embodiments, the non-biological feedstock can be or can derive from natural gas, syngas, $CO_2/H_2$, methanol, ethanol, benzoate, non-volatile residue (NVR) or a caustic wash waste stream from cyclohexane oxidation processes, or terephthalic acid/isophthalic acid mixture waste streams.

The efficient catabolism of methanol has been demonstrated for the methylotrophic yeast *Pichia pastoris*.

The efficient catabolism of ethanol has been demonstrated for *Clostridium kluyveri* (Seedorf et al., *Proc. Natl. Acad. Sci. USA*, 2008, 105(6) 2128-2133).

The efficient catabolism of $CO_2$ and $H_2$, which may be derived from natural gas and other chemical and petrochemical sources, has been demonstrated for *Cupriavidus necator* (Prybylski et al., *Energy, Sustainability and Society*, 2012, 2:11).

The efficient catabolism of syngas has been demonstrated for numerous microorganisms, such as *Clostridium ljungdahlii* and *Clostridium autoethanogenum* (Kopke et al., *Applied and Environmental Microbiology*, 2011, 77(15): 5467-5475).

The efficient catabolism of the non-volatile residue waste stream from cyclohexane processes has been demonstrated for numerous microorganisms, such as *Delftia acidovorans* and *Cupriavidus necator* (Ramsay et al., *Applied and Environmental Microbiology*, 1986, 52(1):152-156).

In some embodiments, the host microorganism is a prokaryote. For example, the prokaryote can be a bacterium from the genus *Escherichia* such as *Escherichia coli*; from the genus *Clostridia* such as *Clostridium ljungdahlii*, *Clostridium autoethanogenum* or *Clostridium kluyveri*; from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens, Pseudomonas putida* or *Pseudomonas oleavorans*; from the genus *Delftia* such as *Delftia acidovorans*; from the genus *Bacillus* such as *Bacillus subtillis*; from the genus *Lactobacillus* such as *Lactobacillus delbrueckii*; or from the genus *Lactococcus* such as *Lactococcus lactis*. Such prokaryotes also can be a source of genes to construct recombinant host cells described herein that are capable of producing one or more C4 building blocks.

In some embodiments, the host microorganism is a eukaryote. For example, the eukaryote can be a filamentous fungus, e.g., one from the genus *Aspergillus* such as *Aspergillus niger*. Alternatively, the eukaryote can be a yeast, e.g., one from the genus *Saccharomyces* such as *Saccharomyces cerevisiae*; from the genus *Pichia* such as *Pichia pastoris*; or from the genus *Yarrowia* such as *Yarrowia lipolytica*; from the genus *Issatchenkia* such as *Issathenkia orientalis*; from the genus *Debaryomyces* such as *Debaryomyces hansenii*; from the genus *Arxula* such as *Arxula adenoinivorans*; or from the genus *Kluyveromyces* such as *Kluyveromyces lactis*. Such eukaryotes also can be a source of genes to construct recombinant host cells described herein that are capable of producing one or more C4 building blocks.

Metabolic Engineering

The present document provides methods involving less than all the steps described for all the above pathways. Such methods can involve, for example, one, two, three, four, five, six, seven, eight, nine, ten, eleven, twelve or more of such steps. Where less than all the steps are included in such a method, the first, and in some embodiments the only, step can be any one of the steps listed.

Furthermore, recombinant hosts described herein can include any combination of the above enzymes such that one or more of the steps, e.g., one, two, three, four, five, six, seven, eight, nine, ten, or more of such steps, can be performed within a recombinant host. This document provides host cells of any of the genera and species listed and genetically engineered to express one or more (e.g., two, three, four, five, six, seven, eight, nine, 10, 11, 12 or more) recombinant forms of any of the enzymes recited in the document. Thus, for example, the host cells can contain exogenous nucleic acids encoding enzymes catalyzing one or more of the steps of any of the pathways described herein.

In addition, this document recognizes that where enzymes have been described as accepting CoA-activated substrates, analogous enzyme activities associated with [acp]-bound substrates exist that are not necessarily in the same enzyme class.

Also, this document recognizes that where enzymes have been described accepting (R)-enantiomers of substrate, analogous enzyme activities associated with (S)-enantiomer substrates exist that are not necessarily in the same enzyme class.

This document also recognizes that where an enzyme is shown to accept a particular co-factor, such as NADPH, or co-substrate, such as acetyl-CoA, many enzymes are promiscuous in terms of accepting a number of different co-factors or co-substrates in catalyzing a particular enzyme activity. Also, this document recognizes that where enzymes have high specificity for e.g., a particular co-factor such as NADH, an enzyme with similar or identical activity that has high specificity for the co-factor NADPH may be in a different enzyme class.

In some embodiments, the enzymes in the pathways outlined herein are the result of enzyme engineering via non-direct or rational enzyme design approaches with aims of improving activity, improving specificity, reducing feedback inhibition, reducing repression, improving enzyme solubility, changing stereo-specificity, or changing co-factor specificity.

In some embodiments, the enzymes in the pathways outlined here can be gene dosed, i.e., overexpressed, into the resulting genetically modified organism via episomal or chromosomal integration approaches.

In some embodiments, genome-scale system biology techniques such as Flux Balance Analysis can be utilized to devise genome scale attenuation or knockout strategies for directing carbon flux to a C4 building block.

Attenuation strategies include, but are not limited to; the use of transposons, homologous recombination (double cross-over approach), mutagenesis, enzyme inhibitors and RNAi interference.

In some embodiments, fluxomic, metabolomic and transcriptomal data can be utilized to inform or support genome-scale system biology techniques, thereby devising genome scale attenuation or knockout strategies in directing carbon flux to a C4 building block.

In some embodiments, the host microorganism's tolerance to high concentrations of a C4 building block can be improved through continuous cultivation in a selective environment.

In some embodiments, the host microorganism's endogenous biochemical network can be attenuated or augmented to (1) ensure the intracellular availability of 2-oxoglutarate or glutamic acid, (2) create a co-factor imbalance that may only be balanced via the formation of one or more C4 building blocks, (3) prevent degradation of central metabolites, central precursors leading to and including one or more C4 building blocks and/or (4) ensure efficient efflux from the cell.

In some embodiments requiring the intracellular availability of 2-oxogluratate or L-glutamate for C4 building block synthesis, the enzymes catalyzing anaplerotic reactions supplementing the citric acid cycle intermediates are amplified, such as a phosphoenolpyruvate carboxylase or a pyruvate carboxylase.

In some embodiments, where pathways require excess NADH co-factor for C4 building block synthesis, a recombinant formate dehydrogenase gene can be overexpressed in the host organism (Shen et al., 2011, supra).

In some embodiments, where pathways require excess NADH or NADPH co-factor for C4 building block synthesis, a transhydrogenase can be attenuated.

In some embodiments, carbon flux can be directed into the pentose phosphate cycle to increase the supply of NADPH by attenuating an endogenous glucose-6-phosphate isomerase (EC 5.3.1.9).

In some embodiments, carbon flux can be redirected into the pentose phosphate cycle to increase the supply of NADPH by overexpression a 6-phosphogluconate dehydrogenase and/or a transketolase (Lee et al., 2003, *Biotechnology Progress*, 19(5), 1444-1449).

In some embodiments, where pathways require excess NADPH co-factor in the synthesis of a C4 building block, a gene such as UdhA encoding apuridine nucleotide transhydrogenase can be overexpressed in the host organisms (Brigham et al., *Advanced Biofuels and Bioproducts*, 2012, Chapter 39, 1065-1090).

In some embodiments, where pathways require excess NADPH co-factor in the synthesis of a C4 Building Block, a recombinant glyceraldehyde-3-phosphate-dehydrogenase gene such as GapN can be overexpressed in the host organisms (Brigham et al., 2012, supra).

In some embodiments, where pathways require excess NADPH co-factor in the synthesis of a C4 building block, a recombinant malic enzyme gene such as maeA or maeB can be overexpressed in the host organisms (Brigham et al., 2012, supra).

In some embodiments, where pathways require excess NADPH co-factor in the synthesis of a C4 building block, a recombinant glucose-6-phosphate dehydrogenase gene such as zwf can be overexpressed in the host organisms (Lim et al., *J. Bioscience and Bioengineering*, 2002, 93(6), 543-549).

In some embodiments, where pathways require excess NADPH co-factor in the synthesis of a C4 building block, a recombinant fructose 1.6 diphosphatase gene such as fbp can be overexpressed in the host organisms (Becker et al., *J. Biotechnol.*, 2007, 132:99-109).

In some embodiments, where pathways require excess NADPH co-factor in the synthesis of a C4 building block, endogenous triose phosphate isomerase (EC 5.3.1.1) can be attenuated.

In some embodiments, where pathways require excess NADPH co-factor in the synthesis of a C4 building block, a recombinant glucose dehydrogenase such as the gene product of gdh can be overexpressed in the host organism (Satoh et al., *J. Bioscience and Bioengineering*, 2003, 95(4):335-341).

In some embodiments, endogenous enzymes facilitating the conversion of NADPH to NADH can be attenuated, such as the NADH generation cycle that may be generated via inter-conversion of glutamate dehydrogenases classified under EC 1.4.1.2 (NADH-specific) and EC 1.4.1.4 (NADPH-specific).

In some embodiments, an endogenous glutamate dehydrogenase (EC 1.4.1.3) that utilizes both NADH and NADPH as co-factors can be attenuated.

In some embodiments using hosts that naturally accumulate polyhydroxyalkanoates, the endogenous polyhydroxyalkanoate synthase enzymes can be attenuated in the host strain.

In some embodiments, a L-alanine dehydrogenase can be overexpressed in the host to regenerate L-alanine from pyruvate as an amino donor for ω-transaminase reactions.

In some embodiments, a L-glutamate dehydrogenase, a L-glutamine synthetase, or a glutamate synthase can be overexpressed in the host to regenerate L-glutamate from 2-oxoglutarate as an amino donor for ω-transaminase reactions.

In some embodiments, the efflux of a C4 building block across the cell membrane to the extracellular media can be enhanced or amplified by genetically engineering structural modifications to the cell membrane or increasing any associated transporter activity for a C4 building block.

The efflux of putrescine can be enhanced or amplified by overexpressing broad substrate range multidrug transporters such as Bit from *Bacillus subtilis* (Woolridge et al., 1997, *J. Biol. Chem.*, 272(14):8864-8866); AcrB and AcrD from *Escherichia coli* (Elkins & Nikaido, 2002, *J. Bacteriol.*, 184(23), 6490-6499), NorA from *Staphylococcus aereus* (Ng et al., 1994, *Antimicrob Agents Chemother*, 38(6), 1345-1355), or Bmr from *Bacillus subtilis* (Neyfakh, 1992, *Antimicrob Agents Chemother*, 36(2), 484-485).

The efflux of 4-aminobutyrate and putrescine can be enhanced or amplified by overexpressing the solute transporters such as the lysE transporter from *Corynebacterium glutamicum* (Bellmann et al., 2001, *Microbiology*, 147, 1765-1774).

Producing C4 Building Blocks Using a Recombinant Host

Typically, one or more C4 building blocks can be produced by providing a host microorganism and culturing the provided microorganism with a culture medium containing a suitable carbon source as described above. In general, the culture media and/or culture conditions can be such that the microorganisms grow to an adequate density and produce a C4 building block efficiently. For large-scale production processes, any method can be used such as those described elsewhere (Manual of Industrial Microbiology and Biotechnology, 2$^{nd}$ Edition, Editors: A. L. Demain and J. E. Davies, ASM Press; and Principles of Fermentation Technology, P. F. Stanbury and A. Whitaker, Pergamon). Briefly, a large tank (e.g., a 100 gallon, 200 gallon, 500 gallon, or more tank) containing an appropriate culture medium is inoculated with a particular microorganism. After inoculation, the microorganism is incubated to allow biomass to be produced. Once a desired biomass is reached, the broth containing the microorganisms can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank.

Once transferred, the microorganisms can be incubated to allow for the production of a C4 building block. Once produced, any method can be used to isolate C4 building blocks. For example, C4 building blocks can be recovered selectively from the fermentation broth via adsorption processes. In the case of 4-aminobutyrate, the resulting eluate can be further concentrated via evaporation, crystallized via evaporative and/or cooling crystallization, and the crystals recovered via centrifugation. In the case of putrescine and 1,4-butanediol, distillation may be employed to achieve the desired product purity.

EXAMPLES

Example 1

Enzyme Activity of Carboxylate Reductase Using 4-Hydroxybutyrate as Substrate and Forming 4-Hydroxybutanal A nucleotide sequence encoding a HIS-tag was added to the nucleic acid sequences from *Mycobacterium smegmatis*, *Segniliparus rugosus* and *Segniliparus rotundus* that encode the carboxylate reductases of SEQ ID NO: 18 (ABK75684.1), SEQ ID NO: 3 (EFV11917.1) and SEQ ID NO: 5 (ADG98140.1), respectively (see FIG. 5), such that N-terminal HIS tagged carboxylate reductases could be produced. Each of the modified genes was cloned into a pET Duet expression vector along with a sfp gene encoding a HIS-tagged phosphopantetheine transferase from *Bacillus subtilis*, both under the T7 promoter. Each expression vector was transformed into a BL21 [DE3] *E. coli* host. The resulting recombinant *E. coli* strains were cultivated in pre-culture containing 20 mL LB media and antibiotic selection pressure at 37° C., thereafter inoculating a 1 L shake flask containing 350 mL LB media with antibiotic selection pressure at 37° C., shaking at 200 rpm. The cultures were induced using 1 mM IPTG and each culture was cultivated overnight at 25° C.

The pellet from each induced shake flask culture was harvested via centrifugation. Each pellet was resuspended and lysed via sonication, and the cell debris was separated from the supernatant via centrifugation at 4° C. The carboxylate reductases and phosphopantetheine transferases were purified from the supernatant using Ni-affinity chromatography and buffer exchanged and concentrated into 50 mM potassium phosphate buffer (pH=6.8), 50 mM NaCl and 5% glycerol via ultrafiltration.

Figure 6:
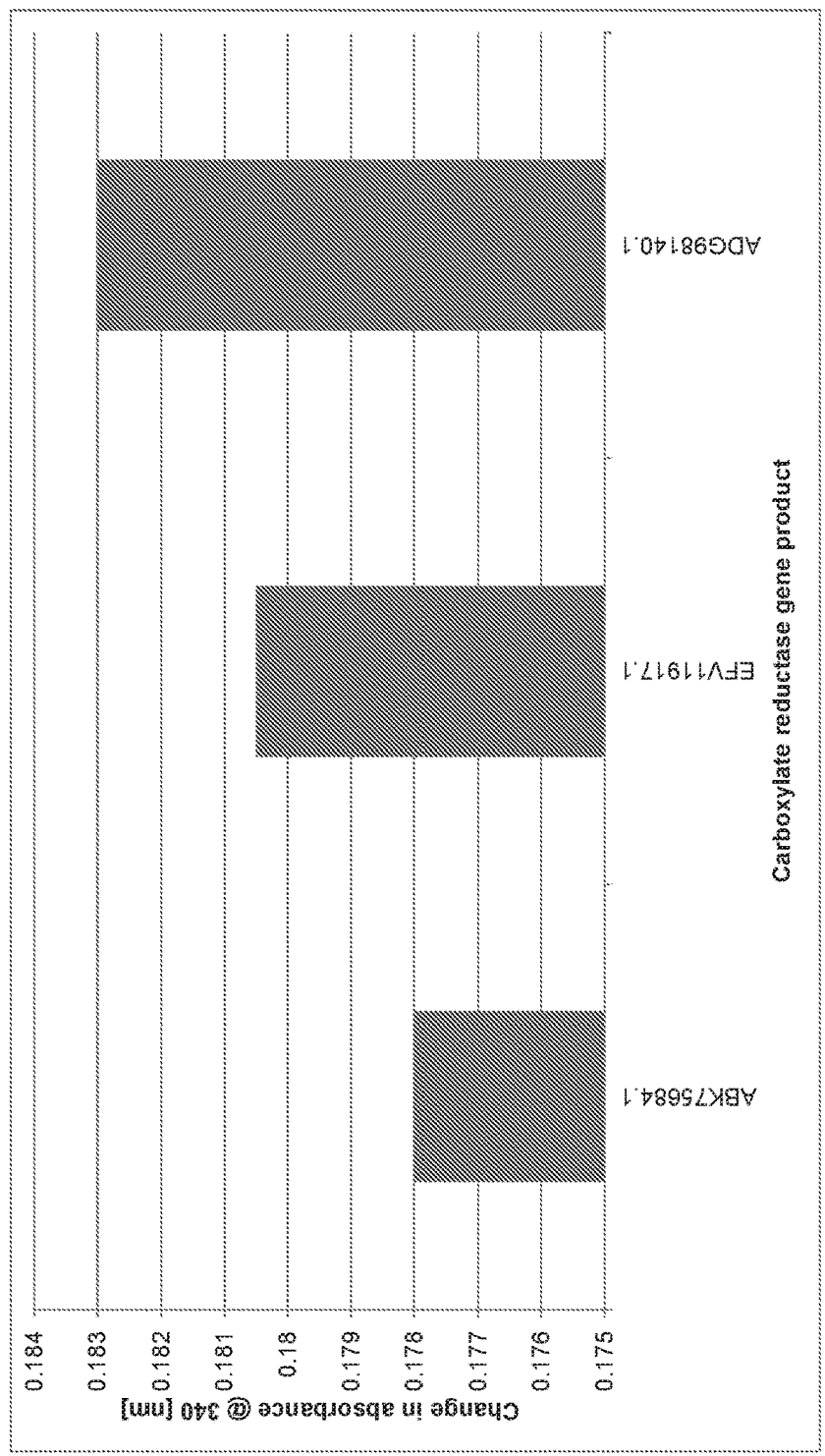
FIG. 6 is a bar graph summarizing the change in absorbance at 340 nm after 1 hour, which is a measure of the consumption of NADPH and activity of three carboxylate reductase preparations in enzyme only controls (no substrate).

Enzyme activity assays (i.e., from γ-butyrolactone via 4-hydroxybutyrate to 4-hydroxybutanal) were performed in duplicate in a buffer composed of a final concentration of 50 mM potassium phosphate buffer (pH=6.8), 75 μM $ZnCl_2$, 1.25 mg/mL *Acinetobacter* sp SE19 lactonase, 10 mM γ-butyrolactone, 10 mM $MgCl_2$, 1 mM ATP and 0.5 mM NADPH. Each enzyme activity assay reaction was initiated by adding purified carboxylate reductase and phosphopantetheine transferase gene products or the empty vector control to the assay buffer containing the 4-hydroxybutyrate formed from γ-butyrolactone and then incubated at room temperature for 1 hour. The consumption of NADPH was monitored by absorbance at 340 nm. Each enzyme only control without γ-butyrolactone demonstrated low base line consumption of NADPH. See bars for ABK75684.1, EFV11917.1 and ADG98140.1 in FIG. 6.

Figure 7:
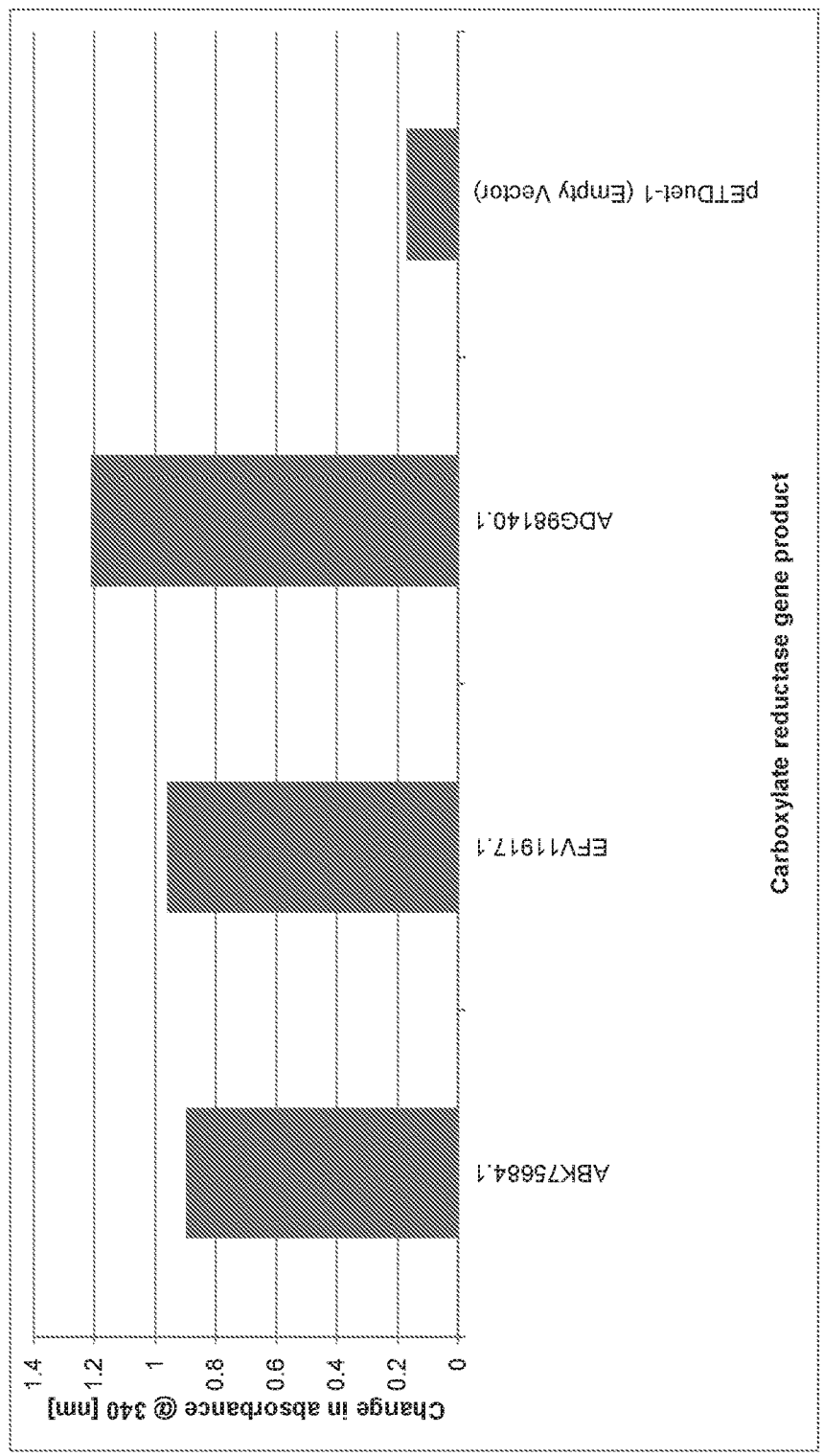
FIG. 7 is a bar graph of the change in absorbance at 340 nm after 1 hour, which is a measure of the consumption of NADPH and the activity of three carboxylate reductase preparations for converting 4-hydroxybutyrate to 4-hydroxybutanal relative to the empty vector control.

The gene products of SEQ ID NOs: 18 (ABK75684.1), SEQ ID NO: 3 (EFV11917.1) and SEQ ID NO: 5 (ADG98140.1), enhanced by the gene product of sfp, accepted 4-hydroxybutyrate as substrate, as confirmed against the empty vector control (see FIG. 7), and synthesized 4-hydroxybutanal.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A recombinant host microorganism comprising:
exogenous nucleic acids encoding (I) a glutamate decarboxylase (EC 4.1.1.15), and (II) an alcohol dehydrogenase selected from the group consisting of a 4-hydroxybutyrate dehydrogenase and a 5-hydroxyvalerate dehydrogenase, and (III) a first ω-transaminase (EC 2.6.1.29); or
exogenous nucleic acids encoding (A) a 2-oxoglutarate decarboxylase (EC 4.1.1.71), and (B) an alcohol dehydrogenase selected from the group consisting of a 4-hydroxybutyrate dehydrogenase and a 5-hydroxyvalerate dehydrogenase,
wherein the recombinant host produces 4-hydroxybutyrate.

2. The recombinant host microorganism of claim 1, said host (i) further comprising an exogenous carboxylate reductase (EC 1.2.99.6), a second and a third exogenous ω-transaminase, and an exogenous alcohol dehydrogenase, wherein the recombinant host further produces putrescine; or (ii) further comprising an exogenous carboxylate reductase and an exogenous alcohol dehydrogenase, wherein the recombinant host further produces 1,4-butanediol.

* * * * *

SEQUENCE LISTING

```
<160> NUMBER OF SEQ ID NOS: 19

<210> SEQ ID NO 1
<211> LENGTH: 1174
<212> TYPE: PRT
<213> ORGANISM: Mycobacterium marinum

<400> SEQUENCE: 1

Met Ser Pro Ile Thr Arg Glu Glu Arg Leu Glu Arg Arg Ile Gln Asp
1               5                   10                  15

Leu Tyr Ala Asn Asp Pro Gln Phe Ala Ala Ala Lys Pro Ala Thr Ala
            20                  25                  30
```

```
Ile Thr Ala Ala Ile Glu Arg Pro Gly Leu Pro Leu Pro Gln Ile Ile
            35                  40                  45

Glu Thr Val Met Thr Gly Tyr Ala Asp Arg Pro Ala Leu Ala Gln Arg
 50                  55                  60

Ser Val Glu Phe Val Thr Asp Ala Gly Thr Gly His Thr Thr Leu Arg
 65                  70                  75                  80

Leu Leu Pro His Phe Glu Thr Ile Ser Tyr Gly Leu Trp Asp Arg
                 85                  90                  95

Ile Ser Ala Leu Ala Asp Val Leu Ser Thr Gln Thr Val Lys Pro
                100                 105                 110

Gly Asp Arg Val Cys Leu Leu Gly Phe Asn Ser Val Asp Tyr Ala Thr
                115                 120                 125

Ile Asp Met Thr Leu Ala Arg Leu Gly Ala Val Ala Val Pro Leu Gln
            130                 135                 140

Thr Ser Ala Ala Ile Thr Gln Leu Gln Pro Ile Val Ala Glu Thr Gln
145                 150                 155                 160

Pro Thr Met Ile Ala Ala Ser Val Asp Ala Leu Ala Asp Ala Thr Glu
                165                 170                 175

Leu Ala Leu Ser Gly Gln Thr Ala Thr Arg Val Leu Val Phe Asp His
                180                 185                 190

His Arg Gln Val Asp Ala His Arg Ala Ala Val Glu Ser Ala Arg Glu
            195                 200                 205

Arg Leu Ala Gly Ser Ala Val Val Glu Thr Leu Ala Glu Ala Ile Ala
                210                 215                 220

Arg Gly Asp Val Pro Arg Gly Ala Ser Ala Gly Ser Ala Pro Gly Thr
225                 230                 235                 240

Asp Val Ser Asp Asp Ser Leu Ala Leu Leu Ile Tyr Thr Ser Gly Ser
                245                 250                 255

Thr Gly Ala Pro Lys Gly Ala Met Tyr Pro Arg Arg Asn Val Ala Thr
                260                 265                 270

Phe Trp Arg Lys Arg Thr Trp Phe Glu Gly Gly Tyr Glu Pro Ser Ile
            275                 280                 285

Thr Leu Asn Phe Met Pro Met Ser His Val Met Gly Arg Gln Ile Leu
            290                 295                 300

Tyr Gly Thr Leu Cys Asn Gly Gly Thr Ala Tyr Phe Val Ala Lys Ser
305                 310                 315                 320

Asp Leu Ser Thr Leu Phe Glu Asp Leu Ala Leu Val Arg Pro Thr Glu
                325                 330                 335

Leu Thr Phe Val Pro Arg Val Trp Asp Met Val Phe Asp Glu Phe Gln
                340                 345                 350

Ser Glu Val Asp Arg Arg Leu Val Asp Gly Ala Asp Arg Val Ala Leu
                355                 360                 365

Glu Ala Gln Val Lys Ala Glu Ile Arg Asn Asp Val Leu Gly Gly Arg
            370                 375                 380

Tyr Thr Ser Ala Leu Thr Gly Ser Ala Pro Ile Ser Asp Glu Met Lys
385                 390                 395                 400

Ala Trp Val Glu Glu Leu Leu Asp Met His Leu Val Glu Gly Tyr Gly
                405                 410                 415

Ser Thr Glu Ala Gly Met Ile Leu Ile Asp Gly Ala Ile Arg Arg Pro
                420                 425                 430

Ala Val Leu Asp Tyr Lys Leu Val Asp Val Pro Asp Leu Gly Tyr Phe
            435                 440                 445
```

```
Leu Thr Asp Arg Pro His Pro Arg Gly Glu Leu Leu Val Lys Thr Asp
450                 455                 460

Ser Leu Phe Pro Gly Tyr Tyr Gln Arg Ala Glu Val Thr Ala Asp Val
465                 470                 475                 480

Phe Asp Ala Asp Gly Phe Tyr Arg Thr Gly Asp Ile Met Ala Glu Val
                485                 490                 495

Gly Pro Glu Gln Phe Val Tyr Leu Asp Arg Arg Asn Asn Val Leu Lys
            500                 505                 510

Leu Ser Gln Gly Glu Phe Val Thr Val Ser Lys Leu Glu Ala Val Phe
        515                 520                 525

Gly Asp Ser Pro Leu Val Arg Gln Ile Tyr Ile Tyr Gly Asn Ser Ala
530                 535                 540

Arg Ala Tyr Leu Leu Ala Val Ile Val Pro Thr Gln Glu Ala Leu Asp
545                 550                 555                 560

Ala Val Pro Val Glu Glu Leu Lys Ala Arg Leu Gly Asp Ser Leu Gln
                565                 570                 575

Glu Val Ala Lys Ala Ala Gly Leu Gln Ser Tyr Glu Ile Pro Arg Asp
            580                 585                 590

Phe Ile Ile Glu Thr Thr Pro Trp Thr Leu Glu Asn Gly Leu Leu Thr
        595                 600                 605

Gly Ile Arg Lys Leu Ala Arg Pro Gln Leu Lys Lys His Tyr Gly Glu
610                 615                 620

Leu Leu Glu Gln Ile Tyr Thr Asp Leu Ala His Gly Asn Ala Asp Glu
625                 630                 635                 640

Leu Arg Ser Leu Arg Gln Ser Gly Ala Asp Ala Pro Val Leu Val Thr
                645                 650                 655

Val Cys Arg Ala Ala Ala Leu Leu Gly Gly Ser Ala Ser Asp Val
            660                 665                 670

Gln Pro Asp Ala His Phe Thr Asp Leu Gly Gly Asp Ser Leu Ser Ala
        675                 680                 685

Leu Ser Phe Thr Asn Leu Leu His Glu Ile Phe Asp Ile Glu Val Pro
690                 695                 700

Val Gly Val Ile Val Ser Pro Ala Asn Asp Leu Gln Ala Leu Ala Asp
705                 710                 715                 720

Tyr Val Glu Ala Ala Arg Lys Pro Gly Ser Ser Arg Pro Thr Phe Ala
                725                 730                 735

Ser Val His Gly Ala Ser Asn Gly Gln Val Thr Glu Val His Ala Gly
            740                 745                 750

Asp Leu Ser Leu Asp Lys Phe Ile Asp Ala Ala Thr Leu Ala Glu Ala
        755                 760                 765

Pro Arg Leu Pro Ala Ala Asn Thr Gln Val Arg Thr Val Leu Leu Thr
770                 775                 780

Gly Ala Thr Gly Phe Leu Gly Arg Tyr Leu Ala Leu Glu Trp Leu Glu
785                 790                 795                 800

Arg Met Asp Leu Val Asp Gly Lys Leu Ile Cys Leu Val Arg Ala Lys
                805                 810                 815

Ser Asp Thr Glu Ala Arg Ala Arg Leu Asp Lys Thr Phe Asp Ser Gly
            820                 825                 830

Asp Pro Glu Leu Leu Ala His Tyr Arg Ala Leu Ala Gly Asp His Leu
        835                 840                 845

Glu Val Leu Ala Gly Asp Lys Gly Glu Ala Asp Leu Gly Leu Asp Arg
850                 855                 860
```

-continued

Gln Thr Trp Gln Arg Leu Ala Asp Thr Val Asp Leu Ile Val Asp Pro
865                 870                 875                 880

Ala Ala Leu Val Asn His Val Leu Pro Tyr Ser Gln Leu Phe Gly Pro
            885                 890                 895

Asn Ala Leu Gly Thr Ala Glu Leu Leu Arg Leu Ala Leu Thr Ser Lys
        900                 905                 910

Ile Lys Pro Tyr Ser Tyr Thr Ser Thr Ile Gly Val Ala Asp Gln Ile
    915                 920                 925

Pro Pro Ser Ala Phe Thr Glu Asp Ala Asp Ile Arg Val Ile Ser Ala
930                 935                 940

Thr Arg Ala Val Asp Asp Ser Tyr Ala Asn Gly Tyr Ser Asn Ser Lys
945                 950                 955                 960

Trp Ala Gly Glu Val Leu Leu Arg Glu Ala His Asp Leu Cys Gly Leu
            965                 970                 975

Pro Val Ala Val Phe Arg Cys Asp Met Ile Leu Ala Asp Thr Thr Trp
        980                 985                 990

Ala Gly Gln Leu Asn Val Pro Asp Met Phe Thr Arg Met Ile Leu Ser
    995                 1000                1005

Leu Ala Ala Thr Gly Ile Ala Pro Gly Ser Phe Tyr Glu Leu Ala Ala
    1010                1015                1020

Asp Gly Ala Arg Gln Arg Ala His Tyr Asp Gly Leu Pro Val Glu Phe
1025                1030                1035                1040

Ile Ala Glu Ala Ile Ser Thr Leu Gly Ala Gln Ser Gln Asp Gly Phe
                1045                1050                1055

His Thr Tyr His Val Met Asn Pro Tyr Asp Asp Gly Ile Gly Leu Asp
            1060                1065                1070

Glu Phe Val Asp Trp Leu Asn Glu Ser Gly Cys Pro Ile Gln Arg Ile
        1075                1080                1085

Ala Asp Tyr Gly Asp Trp Leu Gln Arg Phe Glu Thr Ala Leu Arg Ala
    1090                1095                1100

Leu Pro Asp Arg Gln Arg His Ser Ser Leu Leu Pro Leu Leu His Asn
1105                1110                1115                1120

Tyr Arg Gln Pro Glu Arg Pro Val Arg Gly Ser Ile Ala Pro Thr Asp
                1125                1130                1135

Arg Phe Arg Ala Ala Val Gln Glu Ala Lys Ile Gly Pro Asp Lys Asp
            1140                1145                1150

Ile Pro His Val Gly Ala Pro Ile Ile Val Lys Tyr Val Ser Asp Leu
    1155                1160                1165

Arg Leu Leu Gly Leu Leu
    1170

<210> SEQ ID NO 2
<211> LENGTH: 1173
<212> TYPE: PRT
<213> ORGANISM: Mycobacterium smegmatis

<400> SEQUENCE: 2

Met Thr Ser Asp Val His Asp Ala Thr Asp Gly Val Thr Glu Thr Ala
1               5                   10                  15

Leu Asp Asp Glu Gln Ser Thr Arg Arg Ile Ala Glu Leu Tyr Ala Thr
            20                  25                  30

Asp Pro Glu Phe Ala Ala Ala Pro Leu Pro Ala Val Val Asp Ala
        35                  40                  45

Ala His Lys Pro Gly Leu Arg Leu Ala Glu Ile Leu Gln Thr Leu Phe
    50                  55                  60

-continued

```
Thr Gly Tyr Gly Asp Arg Pro Ala Leu Gly Tyr Arg Ala Arg Glu Leu
 65              70                  75                  80

Ala Thr Asp Glu Gly Gly Arg Thr Val Thr Arg Leu Leu Pro Arg Phe
                 85                  90                  95

Asp Thr Leu Thr Tyr Ala Gln Val Trp Ser Arg Val Gln Ala Val Ala
                100                 105                 110

Ala Ala Leu Arg His Asn Phe Ala Gln Pro Ile Tyr Pro Gly Asp Ala
            115                 120                 125

Val Ala Thr Ile Gly Phe Ala Ser Pro Asp Tyr Leu Thr Leu Asp Leu
130                 135                 140

Val Cys Ala Tyr Leu Gly Leu Val Ser Val Pro Leu Gln His Asn Ala
145                 150                 155                 160

Pro Val Ser Arg Leu Ala Pro Ile Leu Ala Glu Val Glu Pro Arg Ile
                165                 170                 175

Leu Thr Val Ser Ala Glu Tyr Leu Asp Leu Ala Val Glu Ser Val Arg
                180                 185                 190

Asp Val Asn Ser Val Ser Gln Leu Val Val Phe Asp His His Pro Glu
            195                 200                 205

Val Asp Asp His Arg Asp Ala Leu Ala Arg Ala Arg Glu Gln Leu Ala
210                 215                 220

Gly Lys Gly Ile Ala Val Thr Thr Leu Asp Ala Ile Ala Asp Glu Gly
225                 230                 235                 240

Ala Gly Leu Pro Ala Glu Pro Ile Tyr Thr Ala Asp His Asp Gln Arg
                245                 250                 255

Leu Ala Met Ile Leu Tyr Thr Ser Gly Ser Thr Gly Ala Pro Lys Gly
                260                 265                 270

Ala Met Tyr Thr Glu Ala Met Val Ala Arg Leu Trp Thr Met Ser Phe
            275                 280                 285

Ile Thr Gly Asp Pro Thr Pro Val Ile Asn Val Asn Phe Met Pro Leu
290                 295                 300

Asn His Leu Gly Gly Arg Ile Pro Ile Ser Thr Ala Val Gln Asn Gly
305                 310                 315                 320

Gly Thr Ser Tyr Phe Val Pro Glu Ser Asp Met Ser Thr Leu Phe Glu
                325                 330                 335

Asp Leu Ala Leu Val Arg Pro Thr Glu Leu Gly Leu Val Pro Arg Val
            340                 345                 350

Ala Asp Met Leu Tyr Gln His His Leu Ala Thr Val Asp Arg Leu Val
            355                 360                 365

Thr Gln Gly Ala Asp Glu Leu Thr Ala Glu Lys Gln Ala Gly Ala Glu
            370                 375                 380

Leu Arg Glu Gln Val Leu Gly Arg Val Ile Thr Gly Phe Val Ser
385                 390                 395                 400

Thr Ala Pro Leu Ala Ala Glu Met Arg Ala Phe Leu Asp Ile Thr Leu
                405                 410                 415

Gly Ala His Ile Val Asp Gly Tyr Gly Leu Thr Glu Thr Gly Ala Val
            420                 425                 430

Thr Arg Asp Gly Val Ile Val Arg Pro Pro Val Ile Asp Tyr Lys Leu
            435                 440                 445

Ile Asp Val Pro Glu Leu Gly Tyr Phe Ser Thr Asp Lys Pro Tyr Pro
450                 455                 460

Arg Gly Glu Leu Leu Val Arg Ser Gln Thr Leu Thr Pro Gly Tyr Tyr
465                 470                 475                 480
```

-continued

```
Lys Arg Pro Glu Val Thr Ala Ser Val Phe Asp Arg Asp Gly Tyr Tyr
                485                 490                 495

His Thr Gly Asp Val Met Ala Glu Thr Ala Pro Asp His Leu Val Tyr
                500                 505                 510

Val Asp Arg Arg Asn Asn Val Leu Lys Leu Ala Gln Gly Glu Phe Val
                515                 520                 525

Ala Val Ala Asn Leu Glu Ala Val Phe Ser Gly Ala Ala Leu Val Arg
            530                 535                 540

Gln Ile Phe Val Tyr Gly Asn Ser Glu Arg Ser Phe Leu Leu Ala Val
545                 550                 555                 560

Val Val Pro Thr Pro Glu Ala Leu Glu Gln Tyr Asp Pro Ala Ala Leu
                565                 570                 575

Lys Ala Ala Leu Ala Asp Ser Leu Gln Arg Thr Ala Arg Asp Ala Glu
                580                 585                 590

Leu Gln Ser Tyr Glu Val Pro Ala Asp Phe Ile Val Glu Thr Glu Pro
            595                 600                 605

Phe Ser Ala Ala Asn Gly Leu Leu Ser Gly Val Gly Lys Leu Leu Arg
610                 615                 620

Pro Asn Leu Lys Asp Arg Tyr Gly Gln Arg Leu Glu Gln Met Tyr Ala
625                 630                 635                 640

Asp Ile Ala Ala Thr Gln Ala Asn Gln Leu Arg Glu Leu Arg Arg Ala
                645                 650                 655

Ala Ala Thr Gln Pro Val Ile Asp Thr Leu Thr Gln Ala Ala Ala Thr
            660                 665                 670

Ile Leu Gly Thr Gly Ser Glu Val Ala Ser Asp Ala His Phe Thr Asp
            675                 680                 685

Leu Gly Gly Asp Ser Leu Ser Ala Leu Thr Leu Ser Asn Leu Leu Ser
    690                 695                 700

Asp Phe Phe Gly Phe Glu Val Pro Val Gly Thr Ile Val Asn Pro Ala
705                 710                 715                 720

Thr Asn Leu Ala Gln Leu Ala Gln His Ile Glu Ala Gln Arg Thr Ala
                725                 730                 735

Gly Asp Arg Arg Pro Ser Phe Thr Thr Val His Gly Ala Asp Ala Thr
            740                 745                 750

Glu Ile Arg Ala Ser Glu Leu Thr Leu Asp Lys Phe Ile Asp Ala Glu
        755                 760                 765

Thr Leu Arg Ala Ala Pro Gly Leu Pro Lys Val Thr Thr Glu Pro Arg
    770                 775                 780

Thr Val Leu Leu Ser Gly Ala Asn Gly Trp Leu Gly Arg Phe Leu Thr
785                 790                 795                 800

Leu Gln Trp Leu Glu Arg Leu Ala Pro Val Gly Gly Thr Leu Ile Thr
                805                 810                 815

Ile Val Arg Gly Arg Asp Asp Ala Ala Ala Arg Ala Arg Leu Thr Gln
            820                 825                 830

Ala Tyr Asp Thr Asp Pro Glu Leu Ser Arg Arg Phe Ala Glu Leu Ala
        835                 840                 845

Asp Arg His Leu Arg Val Val Ala Gly Asp Ile Gly Asp Pro Asn Leu
    850                 855                 860

Gly Leu Thr Pro Glu Ile Trp His Arg Leu Ala Ala Glu Val Asp Leu
865                 870                 875                 880

Val Val His Pro Ala Ala Leu Val Asn His Val Leu Pro Tyr Arg Gln
                885                 890                 895

Leu Phe Gly Pro Asn Val Val Gly Thr Ala Glu Val Ile Lys Leu Ala
```

```
                        900                 905                 910
Leu Thr Glu Arg Ile Lys Pro Val Thr Tyr Leu Ser Thr Val Ser Val
                915                 920                 925

Ala Met Gly Ile Pro Asp Phe Glu Glu Asp Gly Asp Ile Arg Thr Val
            930                 935                 940

Ser Pro Val Arg Pro Leu Asp Gly Gly Tyr Ala Asn Gly Tyr Gly Asn
945                 950                 955                 960

Ser Lys Trp Ala Gly Glu Val Leu Leu Arg Glu Ala His Asp Leu Cys
                965                 970                 975

Gly Leu Pro Val Ala Thr Phe Arg Ser Asp Met Ile Leu Ala His Pro
            980                 985                 990

Arg Tyr Arg Gly Gln Val Asn Val Pro Asp Met Phe Thr Arg Leu Leu
            995                 1000                1005

Leu Ser Leu Leu Ile Thr Gly Val Ala Pro Arg Ser Phe Tyr Ile Gly
        1010                1015                1020

Asp Gly Glu Arg Pro Arg Ala His Tyr Pro Gly Leu Thr Val Asp Phe
1025                1030                1035                1040

Val Ala Glu Ala Val Thr Thr Leu Gly Ala Gln Gln Arg Glu Gly Tyr
                1045                1050                1055

Val Ser Tyr Asp Val Met Asn Pro His Asp Gly Ile Ser Leu Asp
            1060                1065                1070

Val Phe Val Asp Trp Leu Ile Arg Ala Gly His Pro Ile Asp Arg Val
        1075                1080                1085

Asp Asp Tyr Asp Asp Trp Val Arg Arg Phe Glu Thr Ala Leu Thr Ala
1090                1095                1100

Leu Pro Glu Lys Arg Arg Ala Gln Thr Val Leu Pro Leu Leu His Ala
1105                1110                1115                1120

Phe Arg Ala Pro Gln Ala Pro Leu Arg Gly Ala Pro Glu Pro Thr Glu
                1125                1130                1135

Val Phe His Ala Ala Val Arg Thr Ala Lys Val Gly Pro Gly Asp Ile
            1140                1145                1150

Pro His Leu Asp Glu Ala Leu Ile Asp Lys Tyr Ile Arg Asp Leu Arg
        1155                1160                1165

Glu Phe Gly Leu Ile
    1170

<210> SEQ ID NO 3
<211> LENGTH: 1148
<212> TYPE: PRT
<213> ORGANISM: Segniliparus rugosus

<400> SEQUENCE: 3

Met Gly Asp Gly Glu Glu Arg Ala Lys Arg Phe Phe Gln Arg Ile Gly
1               5                   10                  15

Glu Leu Ser Ala Thr Asp Pro Gln Phe Ala Ala Ala Pro Asp Pro
            20                  25                  30

Ala Val Val Glu Ala Val Ser Asp Pro Ser Leu Ser Phe Thr Arg Tyr
        35                  40                  45

Leu Asp Thr Leu Met Arg Gly Tyr Ala Glu Arg Pro Ala Leu Ala His
    50                  55                  60

Arg Val Gly Ala Gly Tyr Glu Thr Ile Ser Tyr Gly Glu Leu Trp Ala
65                  70                  75                  80

Arg Val Gly Ala Ile Ala Ala Ala Trp Gln Ala Asp Gly Leu Ala Pro
                85                  90                  95
```

-continued

```
Gly Asp Phe Val Ala Thr Val Gly Phe Thr Ser Pro Asp Tyr Val Ala
                100                 105                 110
Val Asp Leu Ala Ala Ala Arg Ser Gly Leu Val Ser Val Pro Leu Gln
            115                 120                 125
Ala Gly Ala Ser Leu Ala Gln Leu Val Gly Ile Leu Glu Glu Thr Glu
        130                 135                 140
Pro Lys Val Leu Ala Ala Ser Ala Ser Ser Leu Glu Gly Ala Val Ala
145                 150                 155                 160
Cys Ala Leu Ala Ala Pro Ser Val Gln Arg Leu Val Val Phe Asp Leu
                165                 170                 175
Arg Gly Pro Asp Ala Ser Glu Ser Ala Ala Asp Glu Arg Arg Gly Ala
            180                 185                 190
Leu Ala Asp Ala Glu Glu Gln Leu Ala Arg Ala Gly Arg Ala Val Val
        195                 200                 205
Val Glu Thr Leu Ala Asp Leu Ala Ala Arg Gly Glu Ala Leu Pro Glu
    210                 215                 220
Ala Pro Leu Phe Glu Pro Ala Glu Gly Glu Asp Pro Leu Ala Leu Leu
225                 230                 235                 240
Ile Tyr Thr Ser Gly Ser Thr Gly Ala Pro Lys Gly Ala Met Tyr Ser
                245                 250                 255
Gln Arg Leu Val Ser Gln Leu Trp Gly Arg Thr Pro Val Val Pro Gly
            260                 265                 270
Met Pro Asn Ile Ser Leu His Tyr Met Pro Leu Ser His Ser Tyr Gly
        275                 280                 285
Arg Ala Val Leu Ala Gly Ala Leu Ser Ala Gly Thr Ala His Phe
    290                 295                 300
Thr Ala Asn Ser Asp Leu Ser Thr Leu Phe Glu Asp Ile Ala Leu Ala
305                 310                 315                 320
Arg Pro Thr Phe Leu Ala Leu Val Pro Arg Val Cys Glu Met Leu Phe
                325                 330                 335
Gln Glu Ser Gln Arg Gly Gln Asp Val Ala Glu Leu Arg Glu Arg Val
            340                 345                 350
Leu Gly Gly Arg Leu Leu Val Ala Val Cys Gly Ser Ala Pro Leu Ser
        355                 360                 365
Pro Glu Met Arg Ala Phe Met Glu Glu Val Leu Gly Phe Pro Leu Leu
    370                 375                 380
Asp Gly Tyr Gly Ser Thr Glu Ala Leu Gly Val Met Arg Asn Gly Ile
385                 390                 395                 400
Ile Gln Arg Pro Pro Val Ile Asp Tyr Lys Leu Val Asp Val Pro Glu
                405                 410                 415
Leu Gly Tyr Arg Thr Thr Asp Lys Pro Tyr Pro Arg Gly Glu Leu Cys
            420                 425                 430
Ile Arg Ser Thr Ser Leu Ile Ser Gly Tyr Tyr Lys Arg Pro Glu Ile
        435                 440                 445
Thr Ala Glu Val Phe Asp Ala Gln Gly Tyr Tyr Lys Thr Gly Asp Val
    450                 455                 460
Met Ala Glu Ile Ala Pro Asp His Leu Val Tyr Val Asp Arg Ser Lys
465                 470                 475                 480
Asn Val Leu Lys Leu Ser Gln Gly Glu Phe Val Ala Val Ala Lys Leu
                485                 490                 495
Glu Ala Ala Tyr Gly Thr Ser Pro Tyr Val Lys Gln Ile Phe Val Tyr
            500                 505                 510
Gly Asn Ser Glu Arg Ser Phe Leu Leu Ala Val Val Val Pro Asn Ala
```

```
            515                 520                 525
Glu Val Leu Gly Ala Arg Asp Gln Glu Ala Lys Pro Leu Ile Ala
            530                 535                 540
Ala Ser Leu Gln Lys Ile Ala Lys Glu Ala Gly Leu Gln Ser Tyr Glu
545                 550                 555                 560
Val Pro Arg Asp Phe Leu Ile Glu Thr Glu Pro Phe Thr Thr Gln Asn
                565                 570                 575
Gly Leu Leu Ser Glu Val Gly Lys Leu Leu Arg Pro Lys Leu Lys Ala
                580                 585                 590
Arg Tyr Gly Glu Ala Leu Glu Ala Arg Tyr Asp Glu Ile Ala His Gly
                595                 600                 605
Gln Ala Asp Glu Leu Arg Ala Leu Arg Asp Gly Ala Gly Gln Arg Pro
            610                 615                 620
Val Val Glu Thr Val Val Arg Ala Ala Val Ala Ile Ser Gly Ser Glu
625                 630                 635                 640
Gly Ala Glu Val Gly Pro Glu Ala Asn Phe Ala Asp Leu Gly Gly Asp
                645                 650                 655
Ser Leu Ser Ala Leu Ser Leu Ala Asn Leu Leu His Asp Val Phe Glu
                660                 665                 670
Val Glu Val Pro Val Arg Ile Ile Ile Gly Pro Thr Ala Ser Leu Ala
            675                 680                 685
Gly Ile Ala Lys His Ile Glu Ala Glu Arg Ala Gly Ala Ser Ala Pro
            690                 695                 700
Thr Ala Ala Ser Val His Gly Ala Gly Ala Thr Arg Ile Arg Ala Ser
705                 710                 715                 720
Glu Leu Thr Leu Glu Lys Phe Leu Pro Glu Asp Leu Leu Ala Ala Ala
                725                 730                 735
Lys Gly Leu Pro Ala Ala Asp Gln Val Arg Thr Val Leu Leu Thr Gly
                740                 745                 750
Ala Asn Gly Trp Leu Gly Arg Phe Leu Ala Leu Glu Gln Leu Glu Arg
            755                 760                 765
Leu Ala Arg Ser Gly Gln Asp Gly Gly Lys Leu Ile Cys Leu Val Arg
            770                 775                 780
Gly Lys Asp Ala Ala Ala Arg Arg Arg Ile Glu Glu Thr Leu Gly
785                 790                 795                 800
Thr Asp Pro Ala Leu Ala Ala Arg Phe Ala Glu Leu Ala Glu Gly Arg
                805                 810                 815
Leu Glu Val Val Pro Gly Asp Val Gly Glu Pro Lys Phe Gly Leu Asp
                820                 825                 830
Asp Ala Ala Trp Asp Arg Leu Ala Glu Glu Val Asp Val Ile Val His
            835                 840                 845
Pro Ala Ala Leu Val Asn His Val Leu Pro Tyr His Gln Leu Phe Gly
            850                 855                 860
Pro Asn Val Val Gly Thr Ala Glu Ile Ile Arg Leu Ala Ile Thr Ala
865                 870                 875                 880
Lys Arg Lys Pro Val Thr Tyr Leu Ser Thr Val Ala Val Ala Ala Gly
                885                 890                 895
Val Glu Pro Ser Ser Phe Glu Glu Asp Gly Asp Ile Arg Ala Val Val
                900                 905                 910
Pro Glu Arg Pro Leu Gly Asp Gly Tyr Ala Asn Gly Tyr Gly Asn Ser
            915                 920                 925
Lys Trp Ala Gly Glu Val Leu Leu Arg Glu Ala His Glu Leu Val Gly
            930                 935                 940
```

Leu Pro Val Ala Val Phe Arg Ser Asp Met Ile Leu Ala His Thr Arg
945                 950                 955                 960

Tyr Thr Gly Gln Leu Asn Val Pro Asp Gln Phe Thr Arg Leu Val Leu
            965                 970                 975

Ser Leu Leu Ala Thr Gly Ile Ala Pro Lys Ser Phe Tyr Gln Gln Gly
            980                 985                 990

Ala Ala Gly Glu Arg Gln Arg Ala His Tyr Asp Gly Ile Pro Val Asp
        995                1000                1005

Phe Thr Ala Glu Ala Ile Thr Thr Leu Gly Ala Glu Pro Ser Trp Phe
    1010                1015                1020

Asp Gly Gly Ala Gly Phe Arg Ser Phe Asp Val Phe Asn Pro His His
1025                1030                1035                1040

Asp Gly Val Gly Leu Asp Glu Phe Val Asp Trp Leu Ile Glu Ala Gly
            1045                1050                1055

His Pro Ile Ser Arg Ile Asp Asp His Lys Glu Trp Phe Ala Arg Phe
            1060                1065                1070

Glu Thr Ala Val Arg Gly Leu Pro Glu Ala Gln Arg Gln His Ser Leu
            1075                1080                1085

Leu Pro Leu Leu Arg Ala Tyr Ser Phe Pro His Pro Val Asp Gly
            1090                1095                1100

Ser Val Tyr Pro Thr Gly Lys Phe Gln Gly Ala Val Lys Ala Ala Gln
1105                1110                1115                1120

Val Gly Ser Asp His Asp Val Pro His Leu Gly Lys Ala Leu Ile Val
            1125                1130                1135

Lys Tyr Ala Asp Asp Leu Lys Ala Leu Gly Leu Leu
            1140                1145

<210> SEQ ID NO 4
<211> LENGTH: 1185
<212> TYPE: PRT
<213> ORGANISM: Mycobacterium massiliense

<400> SEQUENCE: 4

Met Thr Asn Glu Thr Asn Pro Gln Gln Glu Gln Leu Ser Arg Arg Ile
1               5                   10                  15

Glu Ser Leu Arg Glu Ser Asp Pro Gln Phe Arg Ala Ala Gln Pro Asp
            20                  25                  30

Pro Ala Val Ala Glu Gln Val Leu Arg Pro Gly Leu His Leu Ser Glu
        35                  40                  45

Ala Ile Ala Ala Leu Met Thr Gly Tyr Ala Glu Arg Pro Ala Leu Gly
    50                  55                  60

Glu Arg Ala Arg Glu Leu Val Ile Asp Gln Asp Gly Arg Thr Thr Leu
65                  70                  75                  80

Arg Leu Leu Pro Arg Phe Asp Thr Thr Thr Tyr Gly Glu Leu Trp Ser
                85                  90                  95

Arg Thr Thr Ser Val Ala Ala Ala Trp His His Asp Ala Thr His Pro
            100                 105                 110

Val Lys Ala Gly Asp Leu Val Ala Thr Leu Gly Phe Thr Ser Ile Asp
        115                 120                 125

Tyr Thr Val Leu Asp Leu Ala Ile Met Ile Leu Gly Gly Val Ala Val
    130                 135                 140

Pro Leu Gln Thr Ser Ala Pro Ala Ser Gln Trp Thr Thr Ile Leu Ala
145                 150                 155                 160

Glu Ala Glu Pro Asn Thr Leu Ala Val Ser Ile Glu Leu Ile Gly Ala

```
                165                 170                 175
Ala Met Glu Ser Val Arg Ala Thr Pro Ser Ile Lys Gln Val Val
            180                 185                 190

Phe Asp Tyr Thr Pro Glu Val Asp Asp Gln Arg Glu Ala Phe Glu Ala
            195                 200                 205

Ala Ser Thr Gln Leu Ala Gly Thr Gly Ile Ala Leu Glu Thr Leu Asp
            210                 215                 220

Ala Val Ile Ala Arg Gly Ala Leu Pro Ala Ala Pro Leu Tyr Ala
225                 230                 235                 240

Pro Ser Ala Gly Asp Asp Pro Leu Ala Leu Leu Ile Tyr Thr Ser Gly
                245                 250                 255

Ser Thr Gly Ala Pro Lys Gly Ala Met His Ser Glu Asn Ile Val Arg
            260                 265                 270

Arg Trp Trp Ile Arg Glu Asp Val Met Ala Gly Thr Glu Asn Leu Pro
            275                 280                 285

Met Ile Gly Leu Asn Phe Met Pro Met Ser His Ile Met Gly Arg Gly
            290                 295                 300

Thr Leu Thr Ser Thr Leu Ser Thr Gly Gly Thr Gly Tyr Phe Ala Ala
305                 310                 315                 320

Ser Ser Asp Met Ser Thr Leu Phe Glu Asp Met Glu Leu Ile Arg Pro
                325                 330                 335

Thr Ala Leu Ala Leu Val Pro Arg Val Cys Asp Met Val Phe Gln Arg
            340                 345                 350

Phe Gln Thr Glu Val Asp Arg Arg Leu Ala Ser Gly Asp Thr Ala Ser
            355                 360                 365

Ala Glu Ala Val Ala Ala Glu Val Lys Ala Asp Ile Arg Asp Asn Leu
            370                 375                 380

Phe Gly Gly Arg Val Ser Ala Val Met Val Gly Ser Ala Pro Leu Ser
385                 390                 395                 400

Glu Glu Leu Gly Glu Phe Ile Glu Ser Cys Phe Glu Leu Asn Leu Thr
                405                 410                 415

Asp Gly Tyr Gly Ser Thr Glu Ala Gly Met Val Phe Arg Asp Gly Ile
            420                 425                 430

Val Gln Arg Pro Pro Val Ile Asp Tyr Lys Leu Val Asp Val Pro Glu
            435                 440                 445

Leu Gly Tyr Phe Ser Thr Asp Lys Pro His Pro Arg Gly Glu Leu Leu
            450                 455                 460

Leu Lys Thr Asp Gly Met Phe Leu Gly Tyr Tyr Lys Arg Pro Glu Val
465                 470                 475                 480

Thr Ala Ser Val Phe Asp Ala Asp Gly Phe Tyr Met Thr Gly Asp Ile
                485                 490                 495

Val Ala Glu Leu Ala His Asp Asn Ile Glu Ile Asp Arg Arg Asn
            500                 505                 510

Asn Val Leu Lys Leu Ser Gln Gly Glu Phe Val Ala Val Ala Thr Leu
            515                 520                 525

Glu Ala Glu Tyr Ala Asn Ser Pro Val Val His Gln Ile Tyr Val Tyr
            530                 535                 540

Gly Ser Ser Glu Arg Ser Tyr Leu Leu Ala Val Val Pro Thr Pro
545                 550                 555                 560

Glu Ala Val Ala Ala Ala Lys Gly Asp Ala Ala Ala Leu Lys Thr Thr
                565                 570                 575

Ile Ala Asp Ser Leu Gln Asp Ile Ala Lys Glu Ile Gln Leu Gln Ser
            580                 585                 590
```

-continued

Tyr Glu Val Pro Arg Asp Phe Ile Ile Glu Pro Gln Pro Phe Thr Gln
            595                 600                 605

Gly Asn Gly Leu Leu Thr Gly Ile Ala Lys Leu Ala Arg Pro Asn Leu
    610                 615                 620

Lys Ala His Tyr Gly Pro Arg Leu Glu Gln Met Tyr Ala Glu Ile Ala
625                 630                 635                 640

Glu Gln Gln Ala Ala Glu Leu Arg Ala Leu His Gly Val Asp Pro Asp
                645                 650                 655

Lys Pro Ala Leu Glu Thr Val Leu Lys Ala Ala Gln Ala Leu Leu Gly
                660                 665                 670

Val Ser Ser Ala Glu Leu Ala Ala Asp Ala His Phe Thr Asp Leu Gly
            675                 680                 685

Gly Asp Ser Leu Ser Ala Leu Ser Phe Ser Asp Leu Leu Arg Asp Ile
    690                 695                 700

Phe Ala Val Glu Val Pro Val Gly Val Ile Val Ser Ala Ala Asn Asp
705                 710                 715                 720

Leu Gly Gly Val Ala Lys Phe Val Asp Glu Gln Arg His Ser Gly Gly
                725                 730                 735

Thr Arg Pro Thr Ala Glu Thr Val His Gly Ala Gly Thr Glu Ile
            740                 745                 750

Arg Ala Ala Asp Leu Thr Leu Asp Lys Phe Ile Asp Glu Ala Thr Leu
            755                 760                 765

His Ala Ala Pro Ser Leu Pro Lys Ala Ala Gly Ile Pro His Thr Val
    770                 775                 780

Leu Leu Thr Gly Ser Asn Gly Tyr Leu Gly His Tyr Leu Ala Leu Glu
785                 790                 795                 800

Trp Leu Glu Arg Leu Asp Lys Thr Asp Gly Lys Leu Ile Val Ile Val
                805                 810                 815

Arg Gly Lys Asn Ala Glu Ala Ala Tyr Gly Arg Leu Glu Glu Ala Phe
            820                 825                 830

Asp Thr Gly Asp Thr Glu Leu Leu Ala His Phe Arg Ser Leu Ala Asp
    835                 840                 845

Lys His Leu Glu Val Leu Ala Gly Asp Ile Gly Asp Pro Asn Leu Gly
850                 855                 860

Leu Asp Ala Asp Thr Trp Gln Arg Leu Ala Asp Thr Val Asp Val Ile
865                 870                 875                 880

Val His Pro Ala Ala Leu Val Asn His Val Leu Pro Tyr Asn Gln Leu
            885                 890                 895

Phe Gly Pro Asn Val Val Gly Thr Ala Glu Ile Ile Lys Leu Ala Ile
    900                 905                 910

Thr Thr Lys Ile Lys Pro Val Thr Tyr Leu Ser Thr Val Ala Val Ala
    915                 920                 925

Ala Tyr Val Asp Pro Thr Thr Phe Asp Glu Glu Ser Asp Ile Arg Leu
    930                 935                 940

Ile Ser Ala Val Arg Pro Ile Asp Asp Gly Tyr Ala Asn Gly Tyr Gly
945                 950                 955                 960

Asn Ala Lys Trp Ala Gly Glu Val Leu Leu Arg Glu Ala His Asp Leu
                965                 970                 975

Cys Gly Leu Pro Val Ala Val Phe Arg Ser Asp Met Ile Leu Ala His
            980                 985                 990

Ser Arg Tyr Thr Gly Gln Leu Asn Val Pro Asp Gln Phe Thr Arg Leu
    995                 1000                1005

-continued

```
Ile Leu Ser Leu Ile Ala Thr Gly Ile Ala Pro Gly Ser Phe Tyr Gln
    1010                1015                1020

Ala Gln Thr Thr Gly Glu Arg Pro Leu Ala His Tyr Asp Gly Leu Pro
1025                1030                1035                1040

Gly Asp Phe Thr Ala Glu Ala Ile Thr Thr Leu Gly Thr Gln Val Pro
                1045                1050                1055

Glu Gly Ser Glu Gly Phe Val Thr Tyr Asp Cys Val Asn Pro His Ala
                1060                1065                1070

Asp Gly Ile Ser Leu Asp Asn Phe Val Asp Trp Leu Ile Glu Ala Gly
                    1075                1080                1085

Tyr Pro Ile Ala Arg Ile Asp Asn Tyr Thr Glu Trp Phe Thr Arg Phe
    1090                1095                1100

Asp Thr Ala Ile Arg Gly Leu Ser Glu Lys Gln Lys Gln His Ser Leu
1105                1110                1115                1120

Leu Pro Leu Leu His Ala Phe Glu Gln Pro Ser Ala Ala Glu Asn His
                1125                1130                1135

Gly Val Val Pro Ala Lys Arg Phe Gln His Ala Val Gln Ala Ala Gly
                1140                1145                1150

Ile Gly Pro Val Gly Gln Asp Gly Thr Thr Asp Ile Pro His Leu Ser
                    1155                1160                1165

Arg Arg Leu Ile Val Lys Tyr Ala Lys Asp Leu Glu Gln Leu Gly Leu
    1170                1175                1180

Leu
1185

<210> SEQ ID NO 5
<211> LENGTH: 1186
<212> TYPE: PRT
<213> ORGANISM: Segniliparus rotundus

<400> SEQUENCE: 5

Met Thr Gln Ser His Thr Gln Gly Pro Gln Ala Ser Ala Ala His Ser
1               5                   10                  15

Arg Leu Ala Arg Arg Ala Ala Glu Leu Leu Ala Thr Asp Pro Gln Ala
            20                  25                  30

Ala Ala Thr Leu Pro Asp Pro Glu Val Val Arg Gln Ala Thr Arg Pro
        35                  40                  45

Gly Leu Arg Leu Ala Glu Arg Val Asp Ala Ile Leu Ser Gly Tyr Ala
    50                  55                  60

Asp Arg Pro Ala Leu Gly Gln Arg Ser Phe Gln Thr Val Lys Asp Pro
65                  70                  75                  80

Ile Thr Gly Arg Ser Ser Val Glu Leu Leu Pro Thr Phe Asp Thr Ile
                85                  90                  95

Thr Tyr Arg Glu Leu Arg Glu Arg Ala Thr Ala Ile Ala Ser Asp Leu
            100                 105                 110

Ala His His Pro Gln Ala Pro Ala Lys Pro Gly Asp Phe Leu Ala Ser
        115                 120                 125

Ile Gly Phe Ile Ser Val Asp Tyr Val Ala Ile Asp Ile Ala Gly Val
    130                 135                 140

Phe Ala Gly Leu Thr Ala Val Pro Leu Gln Thr Gly Ala Thr Leu Ala
145                 150                 155                 160

Thr Leu Thr Ala Ile Thr Ala Glu Thr Ala Pro Thr Leu Phe Ala Ala
                165                 170                 175

Ser Ile Glu His Leu Pro Thr Ala Val Asp Ala Val Leu Ala Thr Pro
            180                 185                 190
```

Ser Val Arg Arg Leu Leu Val Phe Asp Tyr Arg Ala Gly Ser Asp Glu
    195                 200                 205

Asp Arg Glu Ala Val Glu Ala Ala Lys Arg Lys Ile Ala Asp Ala Gly
210                 215                 220

Ser Ser Val Leu Val Asp Val Leu Asp Glu Val Ile Ala Arg Gly Lys
225                 230                 235                 240

Ser Ala Pro Lys Ala Pro Leu Pro Pro Ala Thr Asp Ala Gly Asp Asp
                245                 250                 255

Ser Leu Ser Leu Leu Ile Tyr Thr Ser Gly Ser Thr Gly Thr Pro Lys
            260                 265                 270

Gly Ala Met Tyr Pro Glu Arg Asn Val Ala His Phe Trp Gly Gly Val
        275                 280                 285

Trp Ala Ala Ala Phe Asp Glu Asp Ala Ala Pro Pro Val Pro Ala Ile
    290                 295                 300

Asn Ile Thr Phe Leu Pro Leu Ser His Val Ala Ser Arg Leu Ser Leu
305                 310                 315                 320

Met Pro Thr Leu Ala Arg Gly Gly Leu Met His Phe Val Ala Lys Ser
                325                 330                 335

Asp Leu Ser Thr Leu Phe Glu Asp Leu Lys Leu Ala Arg Pro Thr Asn
            340                 345                 350

Leu Phe Leu Val Pro Arg Val Val Glu Met Leu Tyr Gln His Tyr Gln
        355                 360                 365

Ser Glu Leu Asp Arg Arg Gly Val Gln Asp Gly Thr Arg Glu Ala Glu
    370                 375                 380

Ala Val Lys Asp Asp Leu Arg Thr Gly Leu Leu Gly Gly Arg Ile Leu
385                 390                 395                 400

Thr Ala Gly Phe Gly Ser Ala Pro Leu Ser Ala Glu Leu Ala Gly Phe
                405                 410                 415

Ile Glu Ser Leu Leu Gln Ile His Leu Val Asp Gly Tyr Gly Ser Thr
            420                 425                 430

Glu Ala Gly Pro Val Trp Arg Asp Gly Tyr Leu Val Lys Pro Pro Val
        435                 440                 445

Thr Asp Tyr Lys Leu Ile Asp Val Pro Glu Leu Gly Tyr Phe Ser Thr
    450                 455                 460

Asp Ser Pro His Pro Arg Gly Glu Leu Ala Ile Lys Thr Gln Thr Ile
465                 470                 475                 480

Leu Pro Gly Tyr Tyr Lys Arg Pro Glu Thr Thr Ala Glu Val Phe Asp
                485                 490                 495

Glu Asp Gly Phe Tyr Leu Thr Gly Asp Val Val Ala Gln Ile Gly Pro
            500                 505                 510

Glu Gln Phe Ala Tyr Val Asp Arg Arg Lys Asn Val Leu Lys Leu Ser
        515                 520                 525

Gln Gly Glu Phe Val Thr Leu Ala Lys Leu Glu Ala Ala Tyr Ser Ser
    530                 535                 540

Ser Pro Leu Val Arg Gln Leu Phe Val Tyr Gly Ser Ser Glu Arg Ser
545                 550                 555                 560

Tyr Leu Leu Ala Val Ile Val Pro Thr Pro Asp Ala Leu Lys Lys Phe
                565                 570                 575

Gly Val Gly Glu Ala Ala Lys Ala Ala Leu Gly Glu Ser Leu Gln Lys
            580                 585                 590

Ile Ala Arg Asp Glu Gly Leu Gln Ser Tyr Glu Val Pro Arg Asp Phe
        595                 600                 605

```
Ile Ile Glu Thr Asp Pro Phe Thr Val Glu Asn Gly Leu Leu Ser Asp
610             615                 620
Ala Arg Lys Ser Leu Arg Pro Lys Leu Lys Glu His Tyr Gly Glu Arg
625             630                 635                 640
Leu Glu Ala Met Tyr Lys Glu Leu Ala Asp Gly Gln Ala Asn Glu Leu
                645                 650                 655
Arg Asp Ile Arg Arg Gly Val Gln Gln Arg Pro Thr Leu Glu Thr Val
            660                 665                 670
Arg Arg Ala Ala Ala Met Leu Gly Ala Ser Ala Ala Glu Ile Lys
                675                 680                 685
Pro Asp Ala His Phe Thr Asp Leu Gly Gly Asp Ser Leu Ser Ala Leu
690                 695                 700
Thr Phe Ser Asn Phe Leu His Asp Leu Phe Glu Val Asp Val Pro Val
705                 710                 715                 720
Gly Val Ile Val Ser Ala Ala Asn Thr Leu Gly Ser Val Ala Glu His
                725                 730                 735
Ile Asp Ala Gln Leu Ala Gly Gly Arg Ala Arg Pro Thr Phe Ala Thr
                740                 745                 750
Val His Gly Lys Gly Ser Thr Thr Ile Lys Ala Ser Asp Leu Thr Leu
    755                 760                 765
Asp Lys Phe Ile Asp Glu Gln Thr Leu Glu Ala Lys His Leu Pro
770                 775                 780
Lys Pro Ala Asp Pro Pro Arg Thr Val Leu Leu Thr Gly Ala Asn Gly
785                 790                 795                 800
Trp Leu Gly Arg Phe Leu Ala Leu Glu Trp Leu Glu Arg Leu Ala Pro
                805                 810                 815
Ala Gly Gly Lys Leu Ile Thr Ile Val Arg Gly Lys Asp Ala Ala Gln
                820                 825                 830
Ala Lys Ala Arg Leu Asp Ala Ala Tyr Glu Ser Gly Asp Pro Lys Leu
                835                 840                 845
Ala Gly His Tyr Gln Asp Leu Ala Ala Thr Thr Leu Glu Val Leu Ala
                850                 855                 860
Gly Asp Phe Ser Glu Pro Arg Leu Gly Leu Asp Glu Ala Thr Trp Asn
865                 870                 875                 880
Arg Leu Ala Asp Glu Val Asp Phe Ile Ser His Pro Gly Ala Leu Val
                885                 890                 895
Asn His Val Leu Pro Tyr Asn Gln Leu Phe Gly Pro Asn Val Ala Gly
                900                 905                 910
Val Ala Glu Ile Ile Lys Leu Ala Ile Thr Thr Arg Ile Lys Pro Val
                915                 920                 925
Thr Tyr Leu Ser Thr Val Ala Val Ala Ala Gly Val Glu Pro Ser Ala
                930                 935                 940
Leu Asp Glu Asp Gly Asp Ile Arg Thr Val Ser Ala Glu Arg Ser Val
945                 950                 955                 960
Asp Glu Gly Tyr Ala Asn Gly Tyr Gly Asn Ser Lys Trp Gly Gly Glu
                965                 970                 975
Val Leu Leu Arg Glu Ala His Asp Arg Thr Gly Leu Pro Val Arg Val
                980                 985                 990
Phe Arg Ser Asp Met Ile Leu Ala His Gln Lys Tyr Thr Gly Gln Val
            995                 1000                1005
Asn Ala Thr Asp Gln Phe Thr Arg Leu Val Gln Ser Leu Leu Ala Thr
            1010                1015                1020
Gly Leu Ala Pro Lys Ser Phe Tyr Glu Leu Asp Ala Gln Gly Asn Arg
```

```
            1025                1030                1035                1040
    Gln Arg Ala His Tyr Asp Gly Ile Pro Val Asp Phe Thr Ala Glu Ser
                        1045                1050                1055
    Ile Thr Thr Leu Gly Gly Asp Gly Leu Glu Gly Tyr Arg Ser Tyr Asn
                        1060                1065                1070
    Val Phe Asn Pro His Arg Asp Gly Val Gly Leu Asp Glu Phe Val Asp
                1075                1080                1085
    Trp Leu Ile Glu Ala Gly His Pro Ile Thr Arg Ile Asp Asp Tyr Asp
                1090                1095                1100
    Gln Trp Leu Ser Arg Phe Glu Thr Ser Leu Arg Gly Leu Pro Glu Ser
    1105                1110                1115                1120
    Lys Arg Gln Ala Ser Val Leu Pro Leu Leu His Ala Phe Ala Arg Pro
                        1125                1130                1135
    Gly Pro Ala Val Asp Gly Ser Pro Phe Arg Asn Thr Val Phe Arg Thr
                        1140                1145                1150
    Asp Val Gln Lys Ala Lys Ile Gly Ala Glu His Asp Ile Pro His Leu
                        1155                1160                1165
    Gly Lys Ala Leu Val Leu Lys Tyr Ala Asp Asp Ile Lys Gln Leu Gly
            1170                1175                1180
    Leu Leu
    1185

<210> SEQ ID NO 6
<211> LENGTH: 459
<212> TYPE: PRT
<213> ORGANISM: Chromobacterium violaceum

<400> SEQUENCE: 6

Met Gln Lys Gln Arg Thr Thr Ser Gln Trp Arg Glu Leu Asp Ala Ala
    1               5                   10                  15
    His His Leu His Pro Phe Thr Asp Thr Ala Ser Leu Asn Gln Ala Gly
                        20                  25                  30
    Ala Arg Val Met Thr Arg Gly Glu Gly Val Tyr Leu Trp Asp Ser Glu
                35                  40                  45
    Gly Asn Lys Ile Ile Asp Gly Met Ala Gly Leu Trp Cys Val Asn Val
            50                  55                  60
    Gly Tyr Gly Arg Lys Asp Phe Ala Glu Ala Ala Arg Arg Gln Met Glu
    65                  70                  75                  80
    Glu Leu Pro Phe Tyr Asn Thr Phe Phe Lys Thr Thr His Pro Ala Val
                        85                  90                  95
    Val Glu Leu Ser Ser Leu Leu Ala Glu Val Thr Pro Ala Gly Phe Asp
                        100                 105                 110
    Arg Val Phe Tyr Thr Asn Ser Gly Ser Glu Ser Val Asp Thr Met Ile
                115                 120                 125
    Arg Met Val Arg Arg Tyr Trp Asp Val Gln Gly Lys Pro Glu Lys Lys
            130                 135                 140
    Thr Leu Ile Gly Arg Trp Asn Gly Tyr His Gly Ser Thr Ile Gly Gly
    145                 150                 155                 160
    Ala Ser Leu Gly Gly Met Lys Tyr Met His Glu Gln Gly Asp Leu Pro
                        165                 170                 175
    Ile Pro Gly Met Ala His Ile Glu Gln Pro Trp Trp Tyr Lys His Gly
                        180                 185                 190
    Lys Asp Met Thr Pro Asp Glu Phe Gly Val Val Ala Ala Arg Trp Leu
                195                 200                 205
```

```
Glu Glu Lys Ile Leu Glu Ile Gly Ala Asp Lys Val Ala Ala Phe Val
    210                 215                 220

Gly Glu Pro Ile Gln Gly Ala Gly Val Ile Val Pro Pro Ala Thr
225                 230                 235                 240

Tyr Trp Pro Glu Ile Glu Arg Ile Cys Arg Lys Tyr Asp Val Leu Leu
                    245                 250                 255

Val Ala Asp Glu Val Ile Cys Gly Phe Gly Arg Thr Gly Glu Trp Phe
                260                 265                 270

Gly His Gln His Phe Gly Phe Gln Pro Asp Leu Phe Thr Ala Ala Lys
            275                 280                 285

Gly Leu Ser Ser Gly Tyr Leu Pro Ile Gly Ala Val Phe Val Gly Lys
        290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                    325                 330                 335

Ala Ala Leu Arg Asp Glu Gly Ile Val Gln Arg Val Lys Asp Asp Ile
                340                 345                 350

Gly Pro Tyr Met Gln Lys Arg Trp Arg Glu Thr Phe Ser Arg Phe Glu
            355                 360                 365

His Val Asp Asp Val Arg Gly Val Gly Met Val Gln Ala Phe Thr Leu
        370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Arg
                    405                 410                 415

Ala Cys Gly Asp His Ile Val Ser Ala Pro Pro Leu Val Met Thr Arg
                420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
        450                 455

<210> SEQ ID NO 7
<211> LENGTH: 468
<212> TYPE: PRT
<213> ORGANISM: Pseudomonas aeruginosa

<400> SEQUENCE: 7

Met Asn Ala Arg Leu His Ala Thr Ser Pro Leu Gly Asp Ala Asp Leu
1               5                   10                  15

Val Arg Ala Asp Gln Ala His Tyr Met His Gly Tyr His Val Phe Asp
                20                  25                  30

Asp His Arg Val Asn Gly Ser Leu Asn Ile Ala Ala Gly Asp Gly Ala
            35                  40                  45

Tyr Ile Tyr Asp Thr Ala Gly Asn Arg Tyr Leu Asp Ala Val Gly Gly
        50                  55                  60

Met Trp Cys Thr Asn Ile Gly Leu Gly Arg Glu Glu Met Ala Arg Thr
65                  70                  75                  80

Val Ala Glu Gln Thr Arg Leu Leu Ala Tyr Ser Asn Pro Phe Cys Asp
                85                  90                  95

Met Ala Asn Pro Arg Ala Ile Glu Leu Cys Arg Lys Leu Ala Glu Leu
                100                 105                 110

Ala Pro Gly Asp Leu Asp His Val Phe Leu Thr Thr Gly Gly Ser Thr
            115                 120                 125
```

```
Ala Val Asp Thr Ala Ile Arg Leu Met His Tyr Tyr Gln Asn Cys Arg
            130                 135                 140

Gly Lys Arg Ala Lys Lys His Val Ile Thr Arg Ile Asn Ala Tyr His
145                 150                 155                 160

Gly Ser Thr Phe Leu Gly Met Ser Leu Gly Gly Lys Ser Ala Asp Arg
                165                 170                 175

Pro Ala Glu Phe Asp Phe Leu Asp Glu Arg Ile His His Leu Ala Cys
                180                 185                 190

Pro Tyr Tyr Tyr Arg Ala Pro Glu Gly Leu Gly Glu Ala Glu Phe Leu
            195                 200                 205

Asp Gly Leu Val Asp Glu Phe Glu Arg Lys Ile Leu Glu Leu Gly Ala
210                 215                 220

Asp Arg Val Gly Ala Phe Ile Ser Glu Pro Val Phe Gly Ser Gly Gly
225                 230                 235                 240

Val Ile Val Pro Pro Ala Gly Tyr His Arg Arg Met Trp Glu Leu Cys
                245                 250                 255

Gln Arg Tyr Asp Val Leu Tyr Ile Ser Asp Glu Val Val Thr Ser Phe
            260                 265                 270

Gly Arg Leu Gly His Phe Phe Ala Ser Gln Ala Val Phe Gly Val Gln
            275                 280                 285

Pro Asp Ile Ile Leu Thr Ala Lys Gly Leu Thr Ser Gly Tyr Gln Pro
290                 295                 300

Leu Gly Ala Cys Ile Phe Ser Arg Arg Ile Trp Glu Val Ile Ala Glu
305                 310                 315                 320

Pro Asp Lys Gly Arg Cys Phe Ser His Gly Phe Thr Tyr Ser Gly His
                325                 330                 335

Pro Val Ala Cys Ala Ala Ala Leu Lys Asn Ile Glu Ile Ile Glu Arg
                340                 345                 350

Glu Gly Leu Leu Ala His Ala Asp Glu Val Gly Arg Tyr Phe Glu Glu
            355                 360                 365

Arg Leu Gln Ser Leu Arg Asp Leu Pro Ile Val Gly Asp Val Arg Gly
            370                 375                 380

Met Arg Phe Met Ala Cys Val Glu Phe Val Ala Asp Lys Ala Ser Lys
385                 390                 395                 400

Ala Leu Phe Pro Glu Ser Leu Asn Ile Gly Glu Trp Val His Leu Arg
                405                 410                 415

Ala Gln Lys Arg Gly Leu Leu Val Arg Pro Ile Val His Leu Asn Val
            420                 425                 430

Met Ser Pro Pro Leu Ile Leu Thr Arg Glu Gln Val Asp Thr Val Val
            435                 440                 445

Arg Val Leu Arg Glu Ser Ile Glu Glu Thr Val Glu Asp Leu Val Arg
450                 455                 460

Ala Gly His Arg
465

<210> SEQ ID NO 8
<211> LENGTH: 454
<212> TYPE: PRT
<213> ORGANISM: Pseudomonas syringae

<400> SEQUENCE: 8

Met Ser Ala Asn Asn Pro Gln Thr Leu Glu Trp Gln Ala Leu Ser Ser
1                   5                   10                  15

Glu His His Leu Ala Pro Phe Ser Asp Tyr Lys Gln Leu Lys Glu Lys
```

```
                20                  25                  30
Gly Pro Arg Ile Ile Thr Arg Ala Glu Gly Val Tyr Leu Trp Asp Ser
            35                  40                  45
Glu Gly Asn Lys Ile Leu Asp Gly Met Ser Gly Leu Trp Cys Val Ala
        50                  55                  60
Ile Gly Tyr Gly Arg Glu Leu Ala Asp Ala Ser Lys Gln Met
65                  70                  75                  80
Arg Glu Leu Pro Tyr Tyr Asn Leu Phe Phe Gln Thr Ala His Pro Pro
                85                  90                  95
Val Leu Glu Leu Ala Lys Ala Ile Ser Asp Ile Ala Pro Glu Gly Met
            100                 105                 110
Asn His Val Phe Phe Thr Gly Ser Gly Ser Glu Gly Asn Asp Thr Met
        115                 120                 125
Leu Arg Met Val Arg His Tyr Trp Ala Leu Lys Gly Gln Pro Asn Lys
            130                 135                 140
Lys Thr Ile Ile Ser Arg Val Asn Gly Tyr His Gly Ser Thr Val Ala
145                 150                 155                 160
Gly Ala Ser Leu Gly Gly Met Thr Tyr Met His Glu Gln Gly Asp Leu
                165                 170                 175
Pro Ile Pro Gly Val Val His Ile Pro Gln Pro Tyr Trp Phe Gly Glu
            180                 185                 190
Gly Gly Asp Met Thr Pro Asp Glu Phe Gly Ile Trp Ala Ala Glu Gln
        195                 200                 205
Leu Glu Lys Lys Ile Leu Glu Leu Gly Val Glu Asn Val Gly Ala Phe
            210                 215                 220
Ile Ala Glu Pro Ile Gln Gly Ala Gly Gly Val Ile Val Pro Pro Asp
225                 230                 235                 240
Ser Tyr Trp Pro Lys Ile Lys Glu Ile Leu Ser Arg Tyr Asp Ile Leu
                245                 250                 255
Phe Ala Ala Asp Glu Val Ile Cys Gly Phe Gly Arg Thr Ser Glu Trp
            260                 265                 270
Phe Gly Ser Asp Phe Tyr Gly Leu Arg Pro Asp Met Met Thr Ile Ala
        275                 280                 285
Lys Gly Leu Thr Ser Gly Tyr Val Pro Met Gly Gly Leu Ile Val Arg
            290                 295                 300
Asp Glu Ile Val Ala Val Leu Asn Glu Gly Gly Asp Phe Asn His Gly
305                 310                 315                 320
Phe Thr Tyr Ser Gly His Pro Val Ala Ala Val Ala Leu Glu Asn
                325                 330                 335
Ile Arg Ile Leu Arg Glu Glu Lys Ile Val Glu Arg Val Arg Ser Glu
            340                 345                 350
Thr Ala Pro Tyr Leu Gln Lys Arg Leu Arg Glu Leu Ser Asp His Pro
        355                 360                 365
Leu Val Gly Glu Val Arg Gly Val Gly Leu Leu Gly Ala Ile Glu Leu
            370                 375                 380
Val Lys Asp Lys Thr Thr Arg Glu Arg Tyr Thr Asp Lys Gly Ala Gly
385                 390                 395                 400
Met Ile Cys Arg Thr Phe Cys Phe Asp Asn Gly Leu Ile Met Arg Ala
                405                 410                 415
Val Gly Asp Thr Met Ile Ile Ala Pro Pro Leu Val Ile Ser Phe Ala
            420                 425                 430
Gln Ile Asp Glu Leu Val Glu Lys Ala Arg Thr Cys Leu Asp Leu Thr
        435                 440                 445
```

Leu Ala Val Leu Gln Gly
      450

<210> SEQ ID NO 9
<211> LENGTH: 467
<212> TYPE: PRT
<213> ORGANISM: Rhodobacter sphaeroides

<400> SEQUENCE: 9

Met Thr Arg Asn Asp Ala Thr Asn Ala Ala Gly Ala Val Gly Ala Ala
1               5                   10                  15

Met Arg Asp His Ile Leu Leu Pro Ala Gln Glu Met Ala Lys Leu Gly
            20                  25                  30

Lys Ser Ala Gln Pro Val Leu Thr His Ala Glu Gly Ile Tyr Val His
        35                  40                  45

Thr Glu Asp Gly Arg Arg Leu Ile Asp Gly Pro Ala Gly Met Trp Cys
    50                  55                  60

Ala Gln Val Gly Tyr Gly Arg Arg Glu Ile Val Asp Ala Met Ala His
65                  70                  75                  80

Gln Ala Met Val Leu Pro Tyr Ala Ser Pro Trp Tyr Met Ala Thr Ser
                85                  90                  95

Pro Ala Ala Arg Leu Ala Glu Lys Ile Ala Thr Leu Thr Pro Gly Asp
            100                 105                 110

Leu Asn Arg Ile Phe Phe Thr Thr Gly Gly Ser Thr Ala Val Asp Ser
        115                 120                 125

Ala Leu Arg Phe Ser Glu Phe Tyr Asn Asn Val Leu Gly Arg Pro Gln
    130                 135                 140

Lys Lys Arg Ile Ile Val Arg Tyr Asp Gly Tyr His Gly Ser Thr Ala
145                 150                 155                 160

Leu Thr Ala Ala Cys Thr Gly Arg Thr Gly Asn Trp Pro Asn Phe Asp
                165                 170                 175

Ile Ala Gln Asp Arg Ile Ser Phe Leu Ser Ser Pro Asn Pro Arg His
            180                 185                 190

Ala Gly Asn Arg Ser Gln Glu Ala Phe Leu Asp Asp Leu Val Gln Glu
        195                 200                 205

Phe Glu Asp Arg Ile Glu Ser Leu Gly Pro Asp Thr Ile Ala Ala Phe
    210                 215                 220

Leu Ala Glu Pro Ile Leu Ala Ser Gly Gly Val Ile Ile Pro Pro Ala
225                 230                 235                 240

Gly Tyr His Ala Arg Phe Lys Ala Ile Cys Glu Lys His Asp Ile Leu
                245                 250                 255

Tyr Ile Ser Asp Glu Val Val Thr Gly Phe Gly Arg Cys Gly Glu Trp
            260                 265                 270

Phe Ala Ser Glu Lys Val Phe Gly Val Pro Asp Ile Ile Thr Phe
        275                 280                 285

Ala Lys Gly Val Thr Ser Gly Tyr Val Pro Leu Gly Gly Leu Ala Ile
    290                 295                 300

Ser Glu Ala Val Leu Ala Arg Ile Ser Gly Glu Asn Ala Lys Gly Ser
305                 310                 315                 320

Trp Phe Thr Asn Gly Tyr Thr Tyr Ser Asn Gln Pro Val Ala Cys Ala
                325                 330                 335

Ala Ala Leu Ala Asn Ile Glu Leu Met Glu Arg Glu Gly Ile Val Asp
            340                 345                 350

Gln Ala Arg Glu Met Ala Asp Tyr Phe Ala Ala Ala Leu Ala Ser Leu

```
                355                 360                 365
Arg Asp Leu Pro Gly Val Ala Glu Thr Arg Ser Val Gly Leu Val Gly
    370                 375                 380

Cys Val Gln Cys Leu Leu Asp Pro Thr Arg Ala Asp Gly Thr Ala Glu
385                 390                 395                 400

Asp Lys Ala Phe Thr Leu Lys Ile Asp Glu Arg Cys Phe Glu Leu Gly
                405                 410                 415

Leu Ile Val Arg Pro Leu Gly Asp Leu Cys Val Ile Ser Pro Pro Leu
            420                 425                 430

Ile Ile Ser Arg Ala Gln Ile Asp Glu Met Val Ala Ile Met Arg Gln
        435                 440                 445

Ala Ile Thr Glu Val Ser Ala Ala His Gly Leu Thr Ala Lys Glu Pro
    450                 455                 460

Ala Ala Val
465

<210> SEQ ID NO 10
<211> LENGTH: 459
<212> TYPE: PRT
<213> ORGANISM: Escherichia coli

<400> SEQUENCE: 10

Met Asn Arg Leu Pro Ser Ser Ala Ser Ala Leu Ala Cys Ser Ala His
1               5                   10                  15

Ala Leu Asn Leu Ile Glu Lys Arg Thr Leu Asp His Glu Glu Met Lys
            20                  25                  30

Ala Leu Asn Arg Glu Val Ile Glu Tyr Phe Lys Glu His Val Asn Pro
        35                  40                  45

Gly Phe Leu Glu Tyr Arg Lys Ser Val Thr Ala Gly Gly Asp Tyr Gly
    50                  55                  60

Ala Val Glu Trp Gln Ala Gly Ser Leu Asn Thr Leu Val Asp Thr Gln
65                  70                  75                  80

Gly Gln Glu Phe Ile Asp Cys Leu Gly Gly Phe Gly Ile Phe Asn Val
                85                  90                  95

Gly His Arg Asn Pro Val Val Ser Ala Val Gln Asn Gln Leu Ala
            100                 105                 110

Lys Gln Pro Leu His Ser Gln Glu Leu Leu Asp Pro Leu Arg Ala Met
        115                 120                 125

Leu Ala Lys Thr Leu Ala Ala Leu Thr Pro Gly Lys Leu Lys Tyr Ser
    130                 135                 140

Phe Phe Cys Asn Ser Gly Thr Glu Ser Val Glu Ala Ala Leu Lys Leu
145                 150                 155                 160

Ala Lys Ala Tyr Gln Ser Pro Arg Gly Lys Phe Thr Phe Ile Ala Thr
                165                 170                 175

Ser Gly Ala Phe His Gly Lys Ser Leu Gly Ala Leu Ser Ala Thr Ala
            180                 185                 190

Lys Ser Thr Phe Arg Lys Pro Phe Met Pro Leu Leu Pro Gly Phe Arg
        195                 200                 205

His Val Pro Phe Gly Asn Ile Glu Ala Met Arg Thr Ala Leu Asn Glu
    210                 215                 220

Cys Lys Lys Thr Gly Asp Asp Val Ala Ala Val Ile Leu Glu Pro Ile
225                 230                 235                 240

Gln Gly Glu Gly Gly Val Ile Leu Pro Pro Gly Tyr Leu Thr Ala
                245                 250                 255
```

```
Val Arg Lys Leu Cys Asp Glu Phe Gly Ala Leu Met Ile Leu Asp Glu
            260                 265                 270

Val Gln Thr Gly Met Gly Arg Thr Gly Lys Met Phe Ala Cys Glu His
        275                 280                 285

Glu Asn Val Gln Pro Asp Ile Leu Cys Leu Ala Lys Ala Leu Gly Gly
    290                 295                 300

Gly Val Met Pro Ile Gly Ala Thr Ile Ala Thr Glu Glu Val Phe Ser
305                 310                 315                 320

Val Leu Phe Asp Asn Pro Phe Leu His Thr Thr Thr Phe Gly Gly Asn
                325                 330                 335

Pro Leu Ala Cys Ala Ala Ala Leu Ala Thr Ile Asn Val Leu Leu Glu
            340                 345                 350

Gln Asn Leu Pro Ala Gln Ala Glu Gln Lys Gly Asp Met Leu Leu Asp
        355                 360                 365

Gly Phe Arg Gln Leu Ala Arg Glu Tyr Pro Asp Leu Val Gln Glu Ala
    370                 375                 380

Arg Gly Lys Gly Met Leu Met Ala Ile Glu Phe Val Asp Asn Glu Ile
385                 390                 395                 400

Gly Tyr Asn Phe Ala Ser Glu Met Phe Arg Gln Arg Val Leu Val Ala
                405                 410                 415

Gly Thr Leu Asn Asn Ala Lys Thr Ile Arg Ile Glu Pro Pro Leu Thr
            420                 425                 430

Leu Thr Ile Glu Gln Cys Glu Leu Val Ile Lys Ala Ala Arg Lys Ala
        435                 440                 445

Leu Ala Ala Met Arg Val Ser Val Glu Glu Ala
    450                 455

<210> SEQ ID NO 11
<211> LENGTH: 453
<212> TYPE: PRT
<213> ORGANISM: Vibrio fluvialis

<400> SEQUENCE: 11

Met Asn Lys Pro Gln Ser Trp Glu Ala Arg Ala Glu Thr Tyr Ser Leu
1               5                   10                  15

Tyr Gly Phe Thr Asp Met Pro Ser Leu His Gln Arg Gly Thr Val Val
                20                  25                  30

Val Thr His Gly Glu Gly Pro Tyr Ile Val Asp Val Asn Gly Arg Arg
            35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175
```

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
    210                 215                 220

Val Met Gly Ala Gly Gly Val Ile Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Met Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 12
<211> LENGTH: 224
<212> TYPE: PRT
<213> ORGANISM: Bacillus subtilis

<400> SEQUENCE: 12

Met Lys Ile Tyr Gly Ile Tyr Met Asp Arg Pro Leu Ser Gln Glu Glu
1               5                   10                  15

Asn Glu Arg Phe Met Ser Phe Ile Ser Pro Lys Arg Glu Lys Cys
            20                  25                  30

Arg Arg Phe Tyr His Lys Glu Asp Ala His Arg Thr Leu Leu Gly Asp
        35                  40                  45

Val Leu Val Arg Ser Val Ile Ser Arg Gln Tyr Gln Leu Asp Lys Ser
    50                  55                  60

Asp Ile Arg Phe Ser Thr Gln Glu Tyr Gly Lys Pro Cys Ile Pro Asp
65                  70                  75                  80

Leu Pro Asp Ala His Phe Asn Ile Ser His Ser Gly Arg Trp Val Ile

```
                    85                  90                  95
Cys Ala Phe Asp Ser Gln Pro Ile Gly Ile Asp Ile Glu Lys Thr Lys
            100                 105                 110

Pro Ile Ser Leu Glu Ile Ala Lys Arg Phe Phe Ser Lys Thr Glu Tyr
            115                 120                 125

Ser Asp Leu Leu Ala Lys Asp Lys Glu Gln Thr Asp Tyr Phe Tyr
130                 135                 140

His Leu Trp Ser Met Lys Glu Ser Phe Ile Lys Gln Glu Gly Lys Gly
145                 150                 155                 160

Leu Ser Leu Pro Leu Asp Ser Phe Ser Val Arg Leu His Gln Asp Gly
                165                 170                 175

Gln Val Ser Ile Glu Leu Pro Asp Ser His Ser Pro Cys Tyr Ile Lys
            180                 185                 190

Thr Tyr Glu Val Asp Pro Gly Tyr Lys Met Ala Val Cys Ala Ala His
            195                 200                 205

Pro Asp Phe Pro Glu Asp Ile Thr Met Val Ser Tyr Glu Glu Leu Leu
210                 215                 220

<210> SEQ ID NO 13
<211> LENGTH: 222
<212> TYPE: PRT
<213> ORGANISM: Nocardia sp. NRRL 5646

<400> SEQUENCE: 13

Met Ile Glu Thr Ile Leu Pro Ala Gly Val Glu Ser Ala Glu Leu Leu
1               5                   10                  15

Glu Tyr Pro Glu Asp Leu Lys Ala His Pro Ala Glu Glu His Leu Ile
            20                  25                  30

Ala Lys Ser Val Glu Lys Arg Arg Asp Phe Ile Gly Ala Arg His
        35                  40                  45

Cys Ala Arg Leu Ala Leu Ala Glu Leu Gly Glu Pro Pro Val Ala Ile
    50                  55                  60

Gly Lys Gly Glu Arg Gly Ala Pro Ile Trp Pro Arg Gly Val Val Gly
65                  70                  75                  80

Ser Leu Thr His Cys Asp Gly Tyr Arg Ala Ala Val Ala His Lys
                85                  90                  95

Met Arg Phe Arg Ser Ile Gly Ile Asp Ala Glu Pro His Ala Thr Leu
            100                 105                 110

Pro Glu Gly Val Leu Asp Ser Val Ser Leu Pro Pro Glu Arg Glu Trp
            115                 120                 125

Leu Lys Thr Thr Asp Ser Ala Leu His Leu Asp Arg Leu Leu Phe Cys
130                 135                 140

Ala Lys Glu Ala Thr Tyr Lys Ala Trp Trp Pro Leu Thr Ala Arg Trp
145                 150                 155                 160

Leu Gly Phe Glu Glu Ala His Ile Thr Phe Glu Ile Glu Asp Gly Ser
                165                 170                 175

Ala Asp Ser Gly Asn Gly Thr Phe His Ser Glu Leu Leu Val Pro Gly
            180                 185                 190

Gln Thr Asn Asp Gly Gly Thr Pro Leu Leu Ser Phe Asp Gly Arg Trp
            195                 200                 205

Leu Ile Ala Asp Gly Phe Ile Leu Thr Ala Ile Ala Tyr Ala
210                 215                 220

<210> SEQ ID NO 14
<211> LENGTH: 466
```

<212> TYPE: PRT
<213> ORGANISM: Escherichia coli

<400> SEQUENCE: 14

Met Asp Gln Lys Leu Leu Thr Asp Phe Arg Ser Glu Leu Leu Asp Ser
1               5                   10                  15

Arg Phe Gly Ala Lys Ala Ile Ser Thr Ile Ala Glu Ser Lys Arg Phe
            20                  25                  30

Pro Leu His Glu Met Arg Asp Asp Val Ala Phe Gln Ile Ile Asn Asp
        35                  40                  45

Glu Leu Tyr Leu Asp Gly Asn Ala Arg Gln Asn Leu Ala Thr Phe Cys
    50                  55                  60

Gln Thr Trp Asp Asp Glu Asn Val His Lys Leu Met Asp Leu Ser Ile
65                  70                  75                  80

Asn Lys Asn Trp Ile Asp Lys Glu Glu Tyr Pro Gln Ser Ala Ala Ile
                85                  90                  95

Asp Leu Arg Cys Val Asn Met Val Ala Asp Leu Trp His Ala Pro Ala
            100                 105                 110

Pro Lys Asn Gly Gln Ala Val Gly Thr Asn Thr Ile Gly Ser Ser Glu
        115                 120                 125

Ala Cys Met Leu Gly Gly Met Ala Met Lys Trp Arg Trp Arg Lys Arg
    130                 135                 140

Met Glu Ala Ala Gly Lys Pro Thr Asp Lys Pro Asn Leu Val Cys Gly
145                 150                 155                 160

Pro Val Gln Ile Cys Trp His Lys Phe Ala Arg Tyr Trp Asp Val Glu
                165                 170                 175

Leu Arg Glu Ile Pro Met Arg Pro Gly Gln Leu Phe Met Asp Pro Lys
            180                 185                 190

Arg Met Ile Glu Ala Cys Asp Glu Asn Thr Ile Gly Val Val Pro Thr
        195                 200                 205

Phe Gly Val Thr Tyr Thr Gly Asn Tyr Glu Phe Pro Gln Pro Leu His
    210                 215                 220

Asp Ala Leu Asp Lys Phe Gln Ala Asp Thr Gly Ile Asp Ile Asp Met
225                 230                 235                 240

His Ile Asp Ala Ala Ser Gly Gly Phe Leu Ala Pro Phe Val Ala Pro
                245                 250                 255

Asp Ile Val Trp Asp Phe Arg Leu Pro Arg Val Lys Ser Ile Ser Ala
            260                 265                 270

Ser Gly His Lys Phe Gly Leu Ala Pro Leu Gly Cys Gly Trp Val Ile
        275                 280                 285

Trp Arg Asp Glu Glu Ala Leu Pro Gln Glu Leu Val Phe Asn Val Asp
    290                 295                 300

Tyr Leu Gly Gly Gln Ile Gly Thr Phe Ala Ile Asn Phe Ser Arg Pro
305                 310                 315                 320

Ala Gly Gln Val Ile Ala Gln Tyr Tyr Glu Phe Leu Arg Leu Gly Arg
                325                 330                 335

Glu Gly Tyr Thr Lys Val Gln Asn Ala Ser Tyr Gln Val Ala Ala Tyr
            340                 345                 350

Leu Ala Asp Glu Ile Ala Lys Leu Gly Pro Tyr Glu Phe Ile Cys Thr
        355                 360                 365

Gly Arg Pro Asp Glu Gly Ile Pro Ala Val Cys Phe Lys Leu Lys Asp
    370                 375                 380

Gly Glu Asp Pro Gly Tyr Thr Leu Tyr Asp Leu Ser Glu Arg Leu Arg
385                 390                 395                 400

```
Leu Arg Gly Trp Gln Val Pro Ala Phe Thr Leu Gly Gly Glu Ala Thr
                405                 410                 415

Asp Ile Val Val Met Arg Ile Met Cys Arg Arg Gly Phe Glu Met Asp
                420                 425                 430

Phe Ala Glu Leu Leu Glu Asp Tyr Lys Ala Ser Leu Lys Tyr Leu
            435                 440                 445

Ser Asp His Pro Lys Leu Gln Gly Ile Ala Gln Asn Ser Phe Lys
    450                 455                 460

His Thr
465

<210> SEQ ID NO 15
<211> LENGTH: 548
<212> TYPE: PRT
<213> ORGANISM: Lactococcus lactis

<400> SEQUENCE: 15

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Pro Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Asn Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Thr Leu Pro Ser Phe Leu Gly Ile
                245                 250                 255

Tyr Asn Gly Lys Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
```

```
                290                 295                 300

Ile Asp Glu Gly Lys Ile Phe Asn Glu Ser Ile Gln Asn Phe Asp Phe
305                 310                 315                 320

Glu Ser Leu Ile Ser Ser Leu Leu Asp Leu Ser Gly Ile Glu Tyr Lys
                325                 330                 335

Gly Lys Tyr Ile Asp Lys Lys Gln Glu Asp Phe Val Pro Ser Asn Ala
                340                 345                 350

Leu Leu Ser Gln Asp Arg Leu Trp Gln Ala Val Glu Asn Leu Thr Gln
                355                 360                 365

Ser Asn Glu Thr Ile Val Ala Glu Gln Gly Thr Ser Phe Phe Gly Ala
370                 375                 380

Ser Ser Ile Phe Leu Lys Pro Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
                420                 425                 430

Gln Leu Thr Val Gln Glu Leu Gly Leu Ala Ile Arg Glu Lys Ile Asn
                435                 440                 445

Pro Ile Cys Phe Ile Ile Asn Asn Asp Gly Tyr Thr Val Glu Arg Glu
                450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Glu Arg Val Val Ser
                485                 490                 495

Lys Ile Val Arg Thr Glu Asn Glu Phe Val Ser Val Met Lys Glu Ala
                500                 505                 510

Gln Ala Asp Pro Asn Arg Met Tyr Trp Ile Glu Leu Val Leu Ala Lys
                515                 520                 525

Glu Asp Ala Pro Lys Val Leu Lys Lys Met Gly Lys Leu Phe Ala Glu
                530                 535                 540

Gln Asn Lys Ser
545

<210> SEQ ID NO 16
<211> LENGTH: 1227
<212> TYPE: PRT
<213> ORGANISM: Mycobacterium smegmatis

<400> SEQUENCE: 16

Met Ser Ser Ser Pro Ser Pro Phe Gly Gln Asn Glu Trp Leu Val Glu
1               5                   10                  15

Glu Met Tyr Arg Lys Phe Arg Asp Asp Pro Ser Ser Val Asp Pro Ser
                20                  25                  30

Trp His Glu Phe Leu Val Asp Tyr Ser Pro Glu Pro Thr Thr Asp Ser
                35                  40                  45

Ala Ser Asn Gly Arg Thr Thr Thr Ala Ala Pro Val Thr Pro Pro Thr
                50                  55                  60

Pro Ala Pro Ala Pro Ala Pro Glu Pro Lys Ala Ala Pro Lys Pro Ala
65                  70                  75                  80

Ala Lys Thr Glu Ala Lys Pro Ala Lys Pro Ala Lys Ser Ala Thr Pro
                85                  90                  95

Ala Lys Gly Asp Glu Ser Gln Ile Leu Arg Gly Ala Ala Ala Ala Val
                100                 105                 110
```

```
Val Lys Asn Met Asn Ala Ser Leu Glu Val Pro Thr Ala Thr Ser Val
        115                 120                 125
Arg Ala Ile Pro Ala Lys Leu Met Ile Asp Asn Arg Val Val Ile Asn
130                 135                 140
Asn His Leu Lys Arg Thr Arg Gly Gly Lys Ile Ser Phe Thr His Leu
145                 150                 155                 160
Leu Gly Tyr Ala Ile Val Gln Ala Val Lys Lys Phe Pro Asn Met Asn
                165                 170                 175
Arg His Phe Ala Val Val Asp Gly Lys Pro Thr Ala Ile Thr Pro Ala
                180                 185                 190
His Thr Asn Leu Gly Leu Ala Ile Asp Leu Gln Gly Lys Asp Gly Asn
                195                 200                 205
Arg Ser Leu Val Val Ala Ala Ile Lys Arg Cys Glu Thr Met Arg Phe
210                 215                 220
Gly Gln Phe Ile Ala Ala Tyr Glu Asp Ile Val Arg Arg Ala Arg Asp
225                 230                 235                 240
Gly Lys Leu Thr Ala Glu Asp Phe Ser Gly Val Thr Ile Ser Leu Thr
                245                 250                 255
Asn Pro Gly Thr Leu Gly Thr Val His Ser Val Pro Arg Leu Met Gln
                260                 265                 270
Gly Gln Gly Ala Ile Ile Gly Ala Gly Ala Met Glu Tyr Pro Ala Glu
                275                 280                 285
Phe Gln Gly Ala Ser Glu Glu Arg Ile Ala Asp Leu Gly Ile Gly Lys
                290                 295                 300
Leu Ile Thr Leu Thr Ser Thr Tyr Asp His Arg Ile Ile Gln Gly Ala
305                 310                 315                 320
Glu Ser Gly Asp Phe Leu Arg Thr Ile His Gln Leu Leu Leu Asp Asp
                325                 330                 335
Asp Phe Phe Asp Glu Ile Phe Arg Glu Leu Gly Ile Pro Tyr Glu Pro
                340                 345                 350
Val Arg Trp Arg Thr Asp Asn Pro Asp Ser Ile Glu Asp Lys Asn Ala
                355                 360                 365
Arg Val Ile Glu Leu Ile Ala Ala Tyr Arg Asn Arg Gly His Leu Met
370                 375                 380
Ala Asp Ile Asp Pro Leu Arg Leu Asp Asn Thr Arg Phe Arg Ser His
385                 390                 395                 400
Pro Asp Leu Asp Val Asn Ser His Gly Leu Thr Leu Trp Asp Leu Asp
                405                 410                 415
Arg Glu Phe Lys Val Asp Gly Phe Ala Gly Val Gln Arg Lys Lys Leu
                420                 425                 430
Arg Asp Ile Leu Ser Val Leu Arg Asp Ala Tyr Cys Arg His Val Gly
                435                 440                 445
Val Glu Tyr Thr His Ile Leu Glu Pro Glu Gln Gln Arg Trp Ile Gln
                450                 455                 460
Glu Arg Val Glu Thr Lys His Asp Lys Pro Thr Val Ala Glu Gln Lys
465                 470                 475                 480
Tyr Ile Leu Ser Lys Leu Asn Ala Ala Glu Ala Phe Glu Thr Phe Leu
                485                 490                 495
Gln Thr Lys Tyr Val Gly Gln Lys Arg Phe Ser Leu Glu Gly Ala Glu
                500                 505                 510
Thr Val Ile Pro Met Met Asp Ala Val Ile Asp Gln Cys Ala Glu His
                515                 520                 525
Gly Leu Asp Glu Val Val Ile Ala Met Pro His Arg Gly Arg Leu Asn
```

```
                530             535             540
Val Leu Ala Asn Ile Val Gly Lys Pro Tyr Ser Gln Ile Phe Ser Glu
545                 550                 555                 560

Phe Glu Gly Asn Leu Asn Pro Ser Gln Ala His Gly Ser Gly Asp Val
                565                 570                 575

Lys Tyr His Leu Gly Ala Thr Gly Thr Tyr Ile Gln Met Phe Gly Asp
                580                 585                 590

Asn Asp Ile Glu Val Ser Leu Thr Ala Asn Pro Ser His Leu Glu Ala
                595                 600                 605

Val Asp Pro Val Leu Glu Gly Leu Val Arg Ala Lys Gln Asp Leu Leu
            610                 615                 620

Asp Thr Gly Glu Glu Gly Ser Asp Asn Arg Phe Ser Val Val Pro Leu
625                 630                 635                 640

Met Leu His Gly Asp Ala Ala Phe Ala Gly Gln Gly Val Val Ala Glu
                645                 650                 655

Thr Leu Asn Leu Ala Leu Leu Arg Gly Tyr Arg Thr Gly Gly Thr Ile
                660                 665                 670

His Ile Val Val Asn Asn Gln Ile Gly Phe Thr Thr Ala Pro Thr Asp
            675                 680                 685

Ser Arg Ser Ser Glu Tyr Cys Thr Asp Val Ala Lys Met Ile Gly Ala
690                 695                 700

Pro Ile Phe His Val Asn Gly Asp Asp Pro Glu Ala Cys Ala Trp Val
705                 710                 715                 720

Ala Arg Leu Ala Val Asp Phe Arg Gln Ala Phe Lys Lys Asp Val Val
                725                 730                 735

Ile Asp Met Leu Cys Tyr Arg Arg Gly His Asn Glu Gly Asp Asp
                740                 745                 750

Pro Ser Met Thr Gln Pro Tyr Met Tyr Asp Val Ile Asp Thr Lys Arg
                755                 760                 765

Gly Ser Arg Lys Ala Tyr Thr Glu Ala Leu Ile Gly Arg Gly Asp Ile
770                 775                 780

Ser Met Lys Glu Ala Glu Asp Ala Leu Arg Asp Tyr Gln Gly Gln Leu
785                 790                 795                 800

Glu Arg Val Phe Asn Glu Val Arg Glu Leu Glu Lys His Glu Ile Glu
                805                 810                 815

Pro Ser Glu Ser Val Glu Ala Asp Gln Gln Ile Pro Ser Lys Leu Ala
                820                 825                 830

Thr Ala Val Asp Lys Ala Met Leu Gln Arg Ile Gly Asp Ala His Leu
                835                 840                 845

Ala Leu Pro Glu Gly Phe Thr Val His Pro Arg Val Arg Pro Val Leu
850                 855                 860

Glu Lys Arg Arg Glu Met Ala Tyr Glu Gly Arg Ile Asp Trp Ala Phe
865                 870                 875                 880

Ala Glu Leu Leu Ala Leu Gly Ser Leu Ile Ala Glu Gly Lys Leu Val
                885                 890                 895

Arg Leu Ser Gly Gln Asp Thr Gln Arg Gly Thr Phe Thr Gln Arg His
                900                 905                 910

Ala Val Ile Val Asp Arg Lys Thr Gly Glu Glu Phe Thr Pro Leu Gln
            915                 920                 925

Leu Leu Ala Thr Asn Pro Asp Gly Thr Pro Thr Gly Gly Lys Phe Leu
            930                 935                 940

Val Tyr Asn Ser Ala Leu Ser Glu Phe Ala Ala Val Gly Phe Glu Tyr
945                 950                 955                 960
```

```
Gly Tyr Ser Val Gly Asn Pro Asp Ala Met Val Leu Trp Glu Ala Gln
                965                 970                 975

Phe Gly Asp Phe Val Asn Gly Ala Gln Ser Ile Ile Asp Glu Phe Ile
            980                 985                 990

Ser Ser Gly Glu Ala Lys Trp Gly Gln Leu Ser Asp Val Val Leu Leu
        995                 1000                1005

Leu Pro His Gly His Glu Gly Gln Gly Pro Asp His Thr Ser Gly Arg
    1010                1015                1020

Ile Glu Arg Phe Leu Gln Leu Trp Ala Glu Gly Ser Met Thr Ile Ala
1025                1030                1035                1040

Met Pro Ser Thr Pro Ala Asn Tyr Phe His Leu Leu Arg Arg His Gly
                1045                1050                1055

Lys Asp Gly Ile Gln Arg Pro Leu Ile Val Phe Thr Pro Lys Ser Met
            1060                1065                1070

Leu Arg Asn Lys Ala Ala Val Ser Asp Ile Arg Asp Phe Thr Glu Ser
        1075                1080                1085

Lys Phe Arg Ser Val Leu Glu Glu Pro Met Tyr Thr Asp Gly Glu Gly
    1090                1095                1100

Asp Arg Asn Lys Val Thr Arg Leu Leu Leu Thr Ser Gly Lys Ile Tyr
1105                1110                1115                1120

Tyr Glu Leu Ala Ala Arg Lys Ala Lys Glu Asn Arg Glu Asp Val Ala
                1125                1130                1135

Ile Val Arg Ile Glu Gln Leu Ala Pro Leu Pro Arg Arg Leu Ala
            1140                1145                1150

Glu Thr Leu Asp Arg Tyr Pro Asn Val Lys Gly Lys Phe Trp Val Gln
        1155                1160                1165

Glu Glu Pro Ala Asn Gln Gly Ala Trp Pro Ser Phe Gly Leu Thr Leu
    1170                1175                1180

Pro Glu Ile Leu Pro Asp His Phe Thr Gly Leu Lys Arg Ile Ser Arg
1185                1190                1195                1200

Arg Ala Met Ser Ala Pro Ser Ser Gly Ser Ser Lys Val His Ala Val
                1205                1210                1215

Glu Gln Gln Glu Ile Leu Asp Thr Ala Phe Gly
            1220                1225

<210> SEQ ID NO 17
<211> LENGTH: 550
<212> TYPE: PRT
<213> ORGANISM: Salmonella typhimurium

<400> SEQUENCE: 17

Met Gln Asn Pro Tyr Thr Val Ala Asp Tyr Leu Leu Asp Arg Leu Ala
1               5                   10                  15

Gly Cys Gly Ile Gly His Leu Phe Gly Val Pro Gly Asp Tyr Asn Leu
            20                  25                  30

Gln Phe Leu Asp His Val Ile Asp His Pro Thr Leu Arg Trp Val Gly
        35                  40                  45

Cys Ala Asn Glu Leu Asn Ala Ala Tyr Ala Ala Asp Gly Tyr Ala Arg
    50                  55                  60

Met Ser Gly Ala Gly Ala Leu Leu Thr Thr Phe Gly Val Gly Glu Leu
65                  70                  75                  80

Ser Ala Ile Asn Gly Ile Ala Gly Ser Tyr Ala Glu Tyr Val Pro Val
                85                  90                  95

Leu His Ile Val Gly Ala Pro Cys Ser Ala Ala Gln Gln Arg Gly Glu
            100                 105                 110
```

```
Leu Met His His Thr Leu Gly Asp Gly Asp Phe Arg His Phe Tyr Arg
            115                 120                 125

Met Ser Gln Ala Ile Ser Ala Ala Ser Ala Ile Leu Asp Glu Gln Asn
130                 135                 140

Ala Cys Phe Glu Ile Asp Arg Val Leu Gly Glu Met Leu Ala Ala Arg
145                 150                 155                 160

Arg Pro Gly Tyr Ile Met Leu Pro Ala Asp Val Ala Lys Lys Thr Ala
                165                 170                 175

Ile Pro Pro Thr Gln Ala Leu Ala Leu Pro Val His Glu Ala Gln Ser
                180                 185                 190

Gly Val Glu Thr Ala Phe Arg Tyr His Ala Arg Gln Cys Leu Met Asn
            195                 200                 205

Ser Arg Arg Ile Ala Leu Leu Ala Asp Phe Leu Ala Gly Arg Phe Gly
210                 215                 220

Leu Arg Pro Leu Leu Gln Arg Trp Met Ala Glu Thr Pro Ile Ala His
225                 230                 235                 240

Ala Thr Leu Leu Met Gly Lys Gly Leu Phe Asp Glu Gln His Pro Asn
                245                 250                 255

Phe Val Gly Thr Tyr Ser Ala Gly Ala Ser Ser Lys Glu Val Arg Gln
                260                 265                 270

Ala Ile Glu Asp Ala Asp Arg Val Ile Cys Val Gly Thr Arg Phe Val
            275                 280                 285

Asp Thr Leu Thr Ala Gly Phe Thr Gln Gln Leu Pro Ala Glu Arg Thr
            290                 295                 300

Leu Glu Ile Gln Pro Tyr Ala Ser Arg Ile Gly Glu Thr Trp Phe Asn
305                 310                 315                 320

Leu Pro Met Ala Gln Ala Val Ser Thr Leu Arg Glu Leu Cys Leu Glu
                325                 330                 335

Cys Ala Phe Ala Pro Pro Thr Arg Ser Ala Gly Gln Pro Val Arg
                340                 345                 350

Ile Asp Lys Gly Glu Leu Thr Gln Glu Ser Phe Trp Gln Thr Leu Gln
            355                 360                 365

Gln Tyr Leu Lys Pro Gly Asp Ile Ile Leu Val Asp Gln Gly Thr Ala
370                 375                 380

Ala Phe Gly Ala Ala Ala Leu Ser Leu Pro Asp Gly Ala Glu Val Val
385                 390                 395                 400

Leu Gln Pro Leu Trp Gly Ser Ile Gly Tyr Ser Leu Pro Ala Ala Phe
                405                 410                 415

Gly Ala Gln Thr Ala Cys Pro Asp Arg Arg Val Ile Leu Ile Ile Gly
                420                 425                 430

Asp Gly Ala Ala Gln Leu Thr Ile Gln Glu Met Gly Ser Met Leu Arg
            435                 440                 445

Asp Gly Gln Ala Pro Val Ile Leu Leu Leu Asn Asn Asp Gly Tyr Thr
450                 455                 460

Val Glu Arg Ala Ile His Gly Ala Ala Gln Arg Tyr Asn Asp Ile Ala
465                 470                 475                 480

Ser Trp Asn Trp Thr Gln Ile Pro Pro Ala Leu Asn Ala Ala Gln Gln
                485                 490                 495

Ala Glu Cys Trp Arg Val Thr Gln Ala Ile Gln Leu Ala Glu Val Leu
                500                 505                 510

Glu Arg Leu Ala Arg Pro Gln Arg Leu Ser Phe Ile Glu Val Met Leu
            515                 520                 525
```

Pro Lys Ala Asp Leu Pro Glu Leu Leu Arg Thr Val Thr Arg Ala Leu
530                 535                 540

Glu Ala Arg Asn Gly Gly
545                 550

<210> SEQ ID NO 18
<211> LENGTH: 1168
<212> TYPE: PRT
<213> ORGANISM: Mycobacterium smegmatis

<400> SEQUENCE: 18

Met Thr Ile Glu Thr Arg Glu Asp Arg Phe Asn Arg Arg Ile Asp His
1               5                   10                  15

Leu Phe Glu Thr Asp Pro Gln Phe Ala Ala Ala Arg Pro Asp Glu Ala
                20                  25                  30

Ile Ser Ala Ala Ala Ala Asp Pro Glu Leu Arg Leu Pro Ala Ala Val
            35                  40                  45

Lys Gln Ile Leu Ala Gly Tyr Ala Asp Arg Pro Ala Leu Gly Lys Arg
50                  55                  60

Ala Val Glu Phe Val Thr Asp Glu Glu Gly Arg Thr Thr Ala Lys Leu
65                  70                  75                  80

Leu Pro Arg Phe Asp Thr Ile Thr Tyr Arg Gln Leu Ala Gly Arg Ile
                85                  90                  95

Gln Ala Val Thr Asn Ala Trp His Asn His Pro Val Asn Ala Gly Asp
                100                 105                 110

Arg Val Ala Ile Leu Gly Phe Thr Ser Val Asp Tyr Thr Thr Ile Asp
            115                 120                 125

Ile Ala Leu Leu Glu Leu Gly Ala Val Ser Val Pro Leu Gln Thr Ser
130                 135                 140

Ala Pro Val Ala Gln Leu Gln Pro Ile Val Ala Glu Thr Glu Pro Lys
145                 150                 155                 160

Val Ile Ala Ser Ser Val Asp Phe Leu Ala Asp Ala Val Ala Leu Val
                165                 170                 175

Glu Ser Gly Pro Ala Pro Ser Arg Leu Val Val Phe Asp Tyr Ser His
            180                 185                 190

Glu Val Asp Asp Gln Arg Glu Ala Phe Glu Ala Ala Lys Gly Lys Leu
        195                 200                 205

Ala Gly Thr Gly Val Val Glu Thr Ile Thr Asp Ala Leu Asp Arg
210                 215                 220

Gly Arg Ser Leu Ala Asp Ala Pro Leu Tyr Val Pro Asp Glu Ala Asp
225                 230                 235                 240

Pro Leu Thr Leu Leu Ile Tyr Thr Ser Gly Ser Thr Gly Thr Pro Lys
                245                 250                 255

Gly Ala Met Tyr Pro Glu Ser Lys Thr Ala Thr Met Trp Gln Ala Gly
            260                 265                 270

Ser Lys Ala Arg Trp Asp Glu Thr Leu Gly Val Met Pro Ser Ile Thr
        275                 280                 285

Leu Asn Phe Met Pro Met Ser His Val Met Gly Arg Gly Ile Leu Cys
290                 295                 300

Ser Thr Leu Ala Ser Gly Gly Thr Ala Tyr Phe Ala Ala Arg Ser Asp
305                 310                 315                 320

Leu Ser Thr Phe Leu Glu Asp Leu Ala Leu Val Arg Pro Thr Gln Leu
                325                 330                 335

Asn Phe Val Pro Arg Ile Trp Asp Met Leu Phe Gln Glu Tyr Gln Ser
            340                 345                 350

```
Arg Leu Asp Asn Arg Arg Ala Glu Gly Ser Glu Asp Arg Ala Glu Ala
            355                 360                 365
Ala Val Leu Glu Glu Val Arg Thr Gln Leu Leu Gly Gly Arg Phe Val
    370                 375                 380
Ser Ala Leu Thr Gly Ser Ala Pro Ile Ser Ala Glu Met Lys Ser Trp
385                 390                 395                 400
Val Glu Asp Leu Leu Asp Met His Leu Leu Glu Gly Tyr Gly Ser Thr
                405                 410                 415
Glu Ala Gly Ala Val Phe Ile Asp Gly Gln Ile Gln Arg Pro Pro Val
            420                 425                 430
Ile Asp Tyr Lys Leu Val Asp Val Pro Asp Leu Gly Tyr Phe Ala Thr
        435                 440                 445
Asp Arg Pro Tyr Pro Arg Gly Glu Leu Leu Val Lys Ser Glu Gln Met
    450                 455                 460
Phe Pro Gly Tyr Tyr Lys Arg Pro Glu Ile Thr Ala Glu Met Phe Asp
465                 470                 475                 480
Glu Asp Gly Tyr Tyr Arg Thr Gly Asp Ile Val Ala Glu Leu Gly Pro
                485                 490                 495
Asp His Leu Glu Tyr Leu Asp Arg Arg Asn Asn Val Leu Lys Leu Ser
            500                 505                 510
Gln Gly Glu Phe Val Thr Val Ser Lys Leu Glu Ala Val Phe Gly Asp
        515                 520                 525
Ser Pro Leu Val Arg Gln Ile Tyr Val Tyr Gly Asn Ser Ala Arg Ser
    530                 535                 540
Tyr Leu Leu Ala Val Val Pro Thr Glu Glu Ala Leu Ser Arg Trp
545                 550                 555                 560
Asp Gly Asp Glu Leu Lys Ser Arg Ile Ser Asp Ser Leu Gln Asp Ala
                565                 570                 575
Ala Arg Ala Ala Gly Leu Gln Ser Tyr Glu Ile Pro Arg Asp Phe Leu
            580                 585                 590
Val Glu Thr Thr Pro Phe Thr Leu Glu Asn Gly Leu Leu Thr Gly Ile
        595                 600                 605
Arg Lys Leu Ala Arg Pro Lys Leu Lys Ala His Tyr Gly Glu Arg Leu
    610                 615                 620
Glu Gln Leu Tyr Thr Asp Leu Ala Glu Gly Gln Ala Asn Glu Leu Arg
625                 630                 635                 640
Glu Leu Arg Arg Asn Gly Ala Asp Arg Pro Val Val Glu Thr Val Ser
                645                 650                 655
Arg Ala Ala Val Ala Leu Leu Gly Ala Ser Val Thr Asp Leu Arg Ser
            660                 665                 670
Asp Ala His Phe Thr Asp Leu Gly Gly Asp Ser Leu Ser Ala Leu Ser
        675                 680                 685
Phe Ser Asn Leu Leu His Glu Ile Phe Asp Val Asp Val Pro Val Gly
    690                 695                 700
Val Ile Val Ser Pro Ala Thr Asp Leu Ala Gly Val Ala Ala Tyr Ile
705                 710                 715                 720
Glu Gly Glu Leu Arg Gly Ser Lys Arg Pro Thr Tyr Ala Ser Val His
                725                 730                 735
Gly Arg Asp Ala Thr Glu Val Arg Ala Arg Asp Leu Ala Leu Gly Lys
            740                 745                 750
Phe Ile Asp Ala Lys Thr Leu Ser Ala Ala Pro Gly Leu Pro Arg Ser
        755                 760                 765
```

-continued

```
Gly Thr Glu Ile Arg Thr Val Leu Leu Thr Gly Ala Thr Gly Phe Leu
770                 775                 780

Gly Arg Tyr Leu Ala Leu Glu Trp Leu Glu Arg Met Asp Leu Val Asp
785                 790                 795                 800

Gly Lys Val Ile Cys Leu Val Arg Ala Arg Ser Asp Asp Glu Ala Arg
                805                 810                 815

Ala Arg Leu Asp Ala Thr Phe Asp Thr Gly Asp Ala Thr Leu Leu Glu
            820                 825                 830

His Tyr Arg Ala Leu Ala Ala Asp His Leu Glu Val Ile Ala Gly Asp
        835                 840                 845

Lys Gly Glu Ala Asp Leu Gly Leu Asp His Asp Thr Trp Gln Arg Leu
    850                 855                 860

Ala Asp Thr Val Asp Leu Ile Val Asp Pro Ala Ala Leu Val Asn His
865                 870                 875                 880

Val Leu Pro Tyr Ser Gln Met Phe Gly Pro Asn Ala Leu Gly Thr Ala
                885                 890                 895

Glu Leu Ile Arg Ile Ala Leu Thr Thr Thr Ile Lys Pro Tyr Val Tyr
            900                 905                 910

Val Ser Thr Ile Gly Val Gly Gln Gly Ile Ser Pro Glu Ala Phe Val
        915                 920                 925

Glu Asp Ala Asp Ile Arg Glu Ile Ser Ala Thr Arg Arg Val Asp Asp
    930                 935                 940

Ser Tyr Ala Asn Gly Tyr Gly Asn Ser Lys Trp Ala Gly Glu Val Leu
945                 950                 955                 960

Leu Arg Glu Ala His Asp Trp Cys Gly Leu Pro Val Ser Val Phe Arg
                965                 970                 975

Cys Asp Met Ile Leu Ala Asp Thr Thr Tyr Ser Gly Gln Leu Asn Leu
            980                 985                 990

Pro Asp Met Phe Thr Arg Leu Met Leu Ser Leu Val Ala Thr Gly Ile
        995                 1000                1005

Ala Pro Gly Ser Phe Tyr Glu Leu Asp Ala Asp Gly Asn Arg Gln Arg
    1010                1015                1020

Ala His Tyr Asp Gly Leu Pro Val Glu Phe Ile Ala Glu Ala Ile Ser
1025                1030                1035                1040

Thr Ile Gly Ser Gln Val Thr Asp Gly Phe Glu Thr Phe His Val Met
                1045                1050                1055

Asn Pro Tyr Asp Asp Gly Ile Gly Leu Asp Glu Tyr Val Asp Trp Leu
            1060                1065                1070

Ile Glu Ala Gly Tyr Pro Val His Arg Val Asp Asp Tyr Ala Thr Trp
        1075                1080                1085

Leu Ser Arg Phe Glu Thr Ala Leu Arg Ala Leu Pro Glu Arg Gln Arg
    1090                1095                1100

Gln Ala Ser Leu Leu Pro Leu Leu His Asn Tyr Gln Gln Pro Ser Pro
1105                1110                1115                1120

Pro Val Cys Gly Ala Met Ala Pro Thr Asp Arg Phe Arg Ala Ala Val
                1125                1130                1135

Gln Asp Ala Lys Ile Gly Pro Asp Lys Asp Ile Pro His Val Thr Ala
            1140                1145                1150

Asp Val Ile Val Lys Tyr Ile Ser Asn Leu Gln Met Leu Gly Leu Leu
        1155                1160                1165
```

```
<210> SEQ ID NO 19
<211> LENGTH: 466
<212> TYPE: PRT
<213> ORGANISM: Escherichia coli

<400> SEQUENCE: 19

Met Asp Lys Lys Gln Val Thr Asp Leu Arg Ser Glu Leu Leu Asp Ser
1               5                   10                  15

Arg Phe Gly Ala Lys Ser Ile Ser Thr Ile Ala Glu Ser Lys Arg Phe
            20                  25                  30

Pro Leu His Glu Met Arg Asp Asp Val Ala Phe Gln Ile Ile Asn Asp
        35                  40                  45

Glu Leu Tyr Leu Asp Gly Asn Ala Arg Gln Asn Leu Ala Thr Phe Cys
    50                  55                  60

Gln Thr Trp Asp Asp Glu Asn Val His Lys Leu Met Asp Leu Ser Ile
65                  70                  75                  80

Asn Lys Asn Trp Ile Asp Lys Glu Gly Tyr Pro Gln Ser Ala Ala Ile
                85                  90                  95

Asp Leu Arg Cys Val Asn Met Val Ala Asp Leu Trp His Ala Pro Ala
            100                 105                 110

Pro Lys Asn Gly Gln Ala Val Gly Thr Asn Thr Ile Gly Ser Ser Glu
        115                 120                 125

Ala Cys Met Leu Gly Gly Met Ala Met Lys Trp Arg Trp Arg Lys Arg
    130                 135                 140

Met Glu Ala Ala Gly Lys Pro Thr Asp Lys Pro Asn Leu Val Cys Gly
145                 150                 155                 160

Pro Val Gln Ile Cys Trp His Lys Phe Ala Arg Tyr Trp Asp Val Glu
                165                 170                 175

Leu Arg Glu Ile Pro Met Arg Pro Gly Gln Leu Phe Met Asp Pro Lys
            180                 185                 190

Arg Met Ile Glu Ala Cys Asp Glu Asn Thr Ile Gly Val Val Pro Thr
        195                 200                 205

Phe Gly Val Thr Tyr Thr Gly Asn Tyr Glu Phe Pro Gln Pro Leu His
    210                 215                 220

Asp Ala Leu Asp Lys Phe Gln Ala Asp Thr Gly Ile Asp Ile Asp Met
225                 230                 235                 240

His Ile Asp Ala Ala Ser Gly Gly Phe Leu Ala Pro Phe Val Ala Pro
                245                 250                 255

Asp Ile Val Trp Asp Phe Arg Leu Pro Arg Val Lys Ser Ile Ser Ala
            260                 265                 270

Ser Gly His Lys Phe Gly Leu Ala Pro Leu Gly Cys Gly Trp Val Ile
        275                 280                 285

Trp Arg Asp Glu Glu Ala Leu Pro Gln Glu Leu Val Phe Asn Val Asp
    290                 295                 300

Tyr Leu Gly Gly Gln Ile Gly Thr Phe Ala Ile Asn Phe Ser Arg Pro
305                 310                 315                 320

Ala Gly Gln Val Ile Ala Gln Tyr Tyr Glu Phe Leu Arg Leu Gly Arg
                325                 330                 335

Glu Gly Tyr Thr Lys Val Gln Asn Ala Ser Tyr Gln Val Ala Ala Tyr
            340                 345                 350

Leu Ala Asp Glu Ile Ala Lys Leu Gly Pro Tyr Glu Phe Ile Cys Thr
        355                 360                 365

Gly Arg Pro Asp Glu Gly Ile Pro Ala Val Cys Phe Lys Leu Lys Asp
    370                 375                 380
```

```
Gly Glu Asp Pro Gly Tyr Thr Leu Tyr Asp Leu Ser Glu Arg Leu Arg
385                 390                 395                 400

Leu Arg Gly Trp Gln Val Pro Ala Phe Thr Leu Gly Gly Glu Ala Thr
            405                 410                 415

Asp Ile Val Val Met Arg Ile Met Cys Arg Arg Gly Phe Glu Met Asp
        420                 425                 430

Phe Ala Glu Leu Leu Leu Glu Asp Tyr Lys Ala Ser Leu Lys Tyr Leu
        435                 440                 445

Ser Asp His Pro Lys Leu Gln Gly Ile Ala Gln Gln Asn Ser Phe Lys
    450                 455                 460

His Thr
465
```